(12) United States Patent
DeMeritt

(10) Patent No.: US 11,865,290 B2
(45) Date of Patent: Jan. 9, 2024

(54) IMPLANTABLE VASCULAR ACCESS PORT WITH DUAL, HIGH-FLOW TRANS-CHAMBER AND LOW-FLOW, ACCESS, AND NEEDLE LOCK FOR HIGH-FLOW

(71) Applicant: John S. DeMeritt, Saddle River, NJ (US)

(72) Inventor: John S. DeMeritt, Saddle River, NJ (US)

( * ) Notice: Subject to any disclaimer, the term of this patent is extended or adjusted under 35 U.S.C. 154(b) by 290 days.

(21) Appl. No.: 17/161,134

(22) Filed: Jan. 28, 2021

(65) Prior Publication Data
US 2021/0213267 A1 Jul. 15, 2021

Related U.S. Application Data

(63) Continuation of application No. 16/825,884, filed on Mar. 20, 2020, now Pat. No. 10,960,196.
(Continued)

(51) Int. Cl.
*A61M 39/02* (2006.01)
(52) U.S. Cl.
CPC . *A61M 39/0208* (2013.01); *A61M 2039/0211* (2013.01); *A61M 2039/0232* (2013.01);
(Continued)
(58) Field of Classification Search
CPC ........ A61M 39/0208; A61M 2039/022; A61M 2039/0226; A61M 2039/0229;
(Continued)

(56) References Cited

U.S. PATENT DOCUMENTS 6,036,682 A * 3/2000 Lange ............... A61M 25/0108
604/264
6,086,555 A 7/2000 Eliasen et al.
(Continued)

OTHER PUBLICATIONS

Baskin, Jacquelyn L. et al. "Management of occlusion and thrombosis associated with long-term indwelling central venous catheters", Lancet, 2009, 374 (9684): p. 159.
(Continued)

*Primary Examiner* — Deanna K Hall
(74) *Attorney, Agent, or Firm* — Neil D. Gershon

(57) ABSTRACT

An implantable vascular access port has a main port body with one or more hollow internal chambers formed therein each with a floor at the base of the internal chamber. The port body has an outlet aperture formed in a sidewall there of the internal chamber. One or more parallel, lateral, or angled-access apertures, relative to the port floor and associated septa are located opposite the outlet aperture in the main port body in a sidewall there of (parallel or lateral or angled-access aperture or septum), with at least a one perpendicular-access aperture and septum located opposite the floor of the internal chamber(s). The port chamber in the area of the outlet aperture has an at least partially conical shape directionally aligned with the parallel or lateral or angled-access aperture and septum, with said outlet aperture in contiguity a reversible outlet tube or port body needle locking mechanism.

20 Claims, 37 Drawing Sheets

Related U.S. Application Data

(60) Provisional application No. 62/927,465, filed on Oct. 29, 2019, provisional application No. 62/889,155, filed on Aug. 20, 2019, provisional application No. 62/885,380, filed on Aug. 12, 2019, provisional application No. 62/823,103, filed on Mar. 25, 2019.

(52) U.S. Cl.
CPC ............... *A61M 2039/0235* (2013.01); *A61M 2039/0238* (2013.01)

(58) Field of Classification Search
CPC ...... A61M 2039/0232; A61M 39/0247; A61M 39/0282; A61M 2039/0261; A61M 2025/0035; A61M 5/14276
See application file for complete search history.

(56) References Cited

U.S. PATENT DOCUMENTS

| | | | |
|---|---|---|---|
| 9,358,378 | B2 | 6/2016 | Hanson et al. |
| 2003/0229323 | A1 | 12/2003 | Haarala et al. |
| 2005/0085778 | A1 | 4/2005 | Parks |
| 2006/0178648 | A1 | 8/2006 | Barron et al. |
| 2007/0219510 | A1* | 9/2007 | Zinn ................. A61M 39/0208 604/288.01 |
| 2007/0233017 | A1* | 10/2007 | Zinn ................. A61M 39/0208 604/288.01 |
| 2008/0319398 | A1 | 12/2008 | Bizup |
| 2009/0099526 | A1 | 4/2009 | Powley et al. |
| 2012/0123536 | A1 | 5/2012 | Kronowitz |
| 2014/0207086 | A1 | 7/2014 | Stats et al. |
| 2014/0207116 | A1 | 7/2014 | Adler et al. |
| 2014/0236105 | A1 | 8/2014 | Hanson et al. |
| 2019/0232035 | A1 | 8/2019 | Fedor et al. |
| 2020/0306520 | A1 | 10/2020 | DeMeritt |

OTHER PUBLICATIONS

Bindraban, N.R. et al. "Lasso technique for retrieving a broken, dislocated port-a-cath fragment", Neth Heart J., 2009, 17(2): pp. 75-76.

PCT Search Report PCT/US2022/044260 (dated Jan. 13, 2023).

* cited by examiner

FIG. 22        PRIOR ART

FIG. 25　　　　　　　　　　　　　　　　　　　　PRIOR ART

IMPLANTABLE VASCULAR ACCESS PORT WITH DUAL, HIGH-FLOW TRANS-CHAMBER AND LOW-FLOW, ACCESS, AND NEEDLE LOCK FOR HIGH-FLOW

CROSS-REFERENCE TO RELATED APPLICATION

This application is a continuation-in-part of application Ser. No. 16/825,884 filed Mar. 20, 2020, now U.S. Pat. No. 10,960,196.

BACKGROUND OF THE INVENTION

This invention relates to medical devices implantable subcutaneously in a patient to facilitate access by medical personnel to the vascular system of the patient.

Subcutaneous vascular access ports are implantable medical devices, which allow for the repeated access to a patients central venous system over time in order to inject various medicines and draw blood for various laboratory tests. Vascular ports are particularly useful in cancer patients in order to administer chemotherapy over prolonged periods of time often under the conditions of poor venous access. Vascular access ports can also be used to inject iodinated contrast material for diagnostic computerized axial tomography (CAT) scans which are often performed in cancer patients. Subcutaneous vascular access ports are designed to facilitate the reliable and rapid access to the central venous system over time by medical professionals. The subcutaneous location is advantageous since the overlying soft tissues act as a barrier to infection when not in use, i.e. when not accessed with a specialized needle. Single lumen and double lumen ports exist respectively for the administration of a single medication and two medications simultaneously.

A typical subcutaneous access port is constructed of a main port body consisting of a hollow largely cylindrical access chamber with a solid impenetrable floor, which is farthest away from the skin, and a more superficial penetrable flexible septum or diaphragm that is close to the skin surface, allowing for repeated needle access to the hollow chamber at different points in time. The impenetrable port body including the sides and floor are often constructed of a metal alloy or plastic material with varying degrees of radiopacity. The penetrable septum is usually formed from a resilient deformable material such as a silicone elastomer and is radiolucent. This enables fluoroscopically guided access when the port cannot be readily accessed with palpation alone. The standard port access needle is a hollow beveled needle called a Huber needle, which is manufactured in various lengths and gauges, designed not to core or remove portions of the silicone septum. The bevel or cutting edge of a Huber needle is almost perpendicular to the needle shaft resulting in parting of the silicone without making a hole. Huber needles typically range in length from 0.5 inches to 1.5 inches in length and 22 to 19 gauge in diameter. The standard cylindrical access chamber typically has a rigid tubular outlet aperture or conduit on one sidewall, which can then be connected to a more flexible catheter, which is then usually inserted into the central veins of a patient, such as the internal jugular vein or the subclavian vein. The flexible catheter material can be cut to the appropriate length for an individual patient and is typically made of either silicone rubber or polyurethane. The catheter can then be inserted into the desired vein by a removable larger plastic sheath system; typically a peel-away sheath made by various manufactures, which contains perforations, which can be split, removing the sheath in two halves, after successful catheter introduction. The port and the attached catheter, in continuity with the central venous system, thereby allows for reliable central venous access over time. Palpating the port body and inserting a needle through the skin and subsequently through the septum into the chamber, until the needle tip hits the back wall establishes venous access, an attempt can then be made to aspirate blood. The ability to freely aspirate blood from the port coupled with the ability to readily inject a saline or other similar solution into the port with minimal resistance is considered satisfactory clinical proof of the establishment of satisfactory vascular access.

A generic example of an access port is shown in sagittal cross section in FIG. 1 and coronal cross section in FIG. 2. This generic known port device 20 includes a main port body 22, which approximates a frusto-conical shape, having a hollow chamber 24, which is essentially cylindrical in shape. The chamber 24 has a flat impenetrable floor or bottom surface 26 and a flexible penetrable and deformable septum 28, exemplarily of silicone elastomer, which is designed to receive a non-coring hollow access needle or Huber needle to establish vascular access. The septum 28 includes a thick central portion 21 and a thinner edge portion or flange 23 for placement in a circumferential channel or groove 25, in order to anchor the septum in place in the main port body 22. The access port 20 shown in FIGS. 1 and 2 is has an outlet aperture 30 on the inside of the port chamber which leads to an attached hollow outlet tube 32, subsequently attaching to a proximal end 34 of an attached intravascular catheter 36, thus allowing for continuity of flow between the port chamber 24, outlet aperture 30, outlet tube 32, and ultimately the proximal end 34 of the attached intravascular catheter 36. The outlet aperture 30 is formed in a sidewall of the main port chamber 24 within the port body 22, at some distance above the floor 26. The generic port is implanted in the subcutaneous tissues of the upper chest wall and then the proximal end 34 of the catheter 36 is then attached to the outlet tube 32 prior to inserting the distal end of the catheter 36 into one of the central veins such as the internal jugular vein or subclavian vein as shown in FIG. 22.

Although vascular ports, as shown implanted in FIG. 22, are effective devices they can malfunction over time sometimes requiring surgical revision or replacement. Problems that can occur include catheter thrombosis, fibrin sheath formation surrounding the intravascular portion of the catheter, and delayed catheter tip migration into an undesirable location. A fibrin sheath is a biological film or coating, which can form around the intravascular portion of the catheter including the tip, restricting or completely blocking flow (FIG. 23). Clot dissolving drugs such as tissue plasminogen activator (TPA) are initially tried to dissolve intracatheter clot and or a surrounding fibrin sheath. If clot-dissolving drugs are ineffective for reestablishing patency when intracatheter clot is present, surgical revision is required. If clot-dissolving drugs such as TPA cannot dissolve or eliminate a surrounding fibrin sheath, mechanical removal of the sheath can be attempted via an endovascular striping procedure with a loop snare (FIG. 24) or alternatively surgical revision of the port can be performed. Endovascular stripping typically entails puncturing the femoral vein in the groin area with placement of an intravascular sheath, diagnostic catheter, subsequently placing a loop snare through the diagnostic catheter and then around the tip of the fibrin sheath covered port catheter under fluoroscopy (FIG. 24). After snaring the port catheter, traction is applied to strip off the overlying attached fibrin sheath or biofilm. This procedure is often effective in removing the fibrin sheath but can result in fracturing the catheter with a resultant intravascular foreign body, which can then migrate to the right heart and or pulmonary circulation (FIG. 25). Similarly, if the catheter tip migrates or flips into a undesirable location such as the internal jugular vein, the tip can be snared from below, after gaining venous access via the femoral vein, and be repositioned or pulled down into the superior vena cava or right atrium (FIG. 26). It may be clinically desirable to have simpler, safer, simpler, and more efficacious methods for maintaining secondary patency and functionality of vascular access ports.

If the catheter (tunneled or non-tunneled) exits the skin, unlike a port, which is wholly contained under the skin, additional established methods are available to remedy the aforementioned problems. These largely center on the ability to place a wire through the proximal hub of the catheter. Wire advancement and manipulation through the catheter lumen can be used to dislodge intraluminal clot or disrupt an overlying fibrin sheath, often reestablishing patency of the catheter. Small wire brushes typically used for obtaining cytology samples from the mucosal surfaces of the bile ducts or ureters have also been used for the purpose of reestablishing catheter patency in lieu of a simple wire manipulation. If the wire or brush manipulations are unsuccessful, the catheters can be exchanged over a wire for a new catheter. In addition, balloon disruption of the intravascular fibrin sheath, after removal of the dysfunctional catheter over a wire (typically accomplished through a valved vascular sheath) can also be performed prior to placement of the new catheter, to ensure there is no remaining fibrin sheath adherent to the vessel wall.

During port placement, difficulty can occur with the formation of a redundant loop of catheter in the soft tissues, which can be difficult to straighten out or reduce. This typically occurs in the subcutaneous tissues near the venous entrance site after initial intravascular catheter placement, via a lubricious plastic tube or peel-away sheath, which is advanced into the vein and then removed. The redundant catheter loop results in kinking of the catheter and resultant device malfunction. The redundant loop can at times be difficult to remedy, requiring extensive soft tissue manipulation or surgical revision. It may be clinically desirable to have more reliable and efficacious methods for initial catheter placement and ways of fixing such catheter placement complications.

Port removal can on occasion result in inadvertent cutting or separation of the catheter from the port body with a resultant intravascular foreign body, and the catheter is often difficult to identify and palpate during surgical removal, making removal of the port and the attached catheter difficult, particularly if there is abundant surrounding scar tissue or the catheter is old, degraded, and fragile. During this process the catheter can be inadvertently cut or become disconnected with consequent creation of a loose intravascular foreign body. Surgical port revision or replacement can also be a lengthy process, first the old port and catheter must be removed and then a new port must be placed in a stepwise fashion similar to initial placement. A port design to better address the aforementioned issues may be desirable.

Standard port design does not allow for high flow applications like apheresis or dialysis, most available devices are not able to achieve the necessary flow rates. It may be desirable to have a vascular access port which maintains easy or routine needle access for low flow applications like medication administration and blood draws while at the same time allowing for high flow applications such as apheresis or dialysis. The C.R. BARD PowerFlow port (US Patent Application Publication No. 2014/0207086) allows for high flow applications such as apheresis but is difficult to access requiring specialized nursing training, limiting its clinical utility for routine low flow intravenous access in particular. The design necessitates a number of unique steps to access the port, dissimilar from the methodology to access traditional ports, preventing routine use by lesser-trained nursing personal. Additionally, a plastic deformable angiocatheter is advanced at an angle through a rigid access channel in the device, which can potentially kink or crimp, reducing flow rates and preventing reliable vascular access. These design features significantly limit its effectiveness at addressing the aforementioned clinical problems.

US Patent Application Publication No. 2005/0085778 describes a port apparatus 38 (FIGS. 3 and 4 herein) that provides a suboptimal solution to some of the aforementioned problems by theoretically enabling placement of a guide wire 40 through a directionally aimed curved port chamber 42, similar in shape to a bubble pipe bowl or old-fashioned ear trumpet, utilizing a specialized curved needle (WYR-GYD needle) 44 with a pencil point tip and a side hole 46 located near its distal end, approximating a right angle. After penetrating the port septum 48 at a specific orientation, the curved WYR-GYD needle 44 in combination with the saucerized port chamber 42 direct the wire 40 toward the exiting catheter 50 (FIG. 4). The design requires utilization of a specialized curved WYR-GYD non-standard needle 44 to access the port 38 at a specific orientation, increasing access difficultly over current devices, particularly without the aide of fluoroscopy or special training. These requirements may significantly limit the devices utility for routine clinical work by healthcare professionals over current devices. The stocking of specialized curved WYR-GYD needles 44 for routine clinical access for a single specific device is also impractical. The saucerized or sloping port chamber 42 may also make it difficult to access the port 38 with a standard straight or 90 degree Huber needle since the depth varies from one side of the port to the other, making it difficult to advance the needle to the needed depth for reliable vascular access in a consistent manner. There is no other means of accessing the port for routine clinical work. Even if the port is successfully accessed with the special non-standard curved WYR-GYD needle 44, the wire 40 is advanced at a 90-degree angle, a distinct mechanical disadvantage with associated increased resistance, thereby limiting wire advancement, manipulation, and steerability. In addition to limiting wire manipulation the 90-degree orientation of the wire, limits the ability to perform other interventions such as exchange of the device over a wire in order to facilitate surgical revision. Additionally, the design does not allow for high flow applications such as apheresis or dialysis. These design features significantly limit its effectiveness at addressing the aforementioned clinical problems.

OBJECTS OF THE INVENTION

It is an object of the present invention to provide an improved vascular access device and/or an associated surgical method, which addresses the afore-mentioned problems.

It is a more specific object of the present invention to provide an improved vascular access port and/or an associated surgical method that enables both routine low-flow vascular access and special high-flow vascular access.

These and other objects of the present invention will be apparent from the drawings and descriptions hereof. Although every object of the invention is considered to be attained by at least one embodiment of the invention, there is not necessarily any single embodiment that achieves all of the objects of the invention.

SUMMARY OF THE INVENTION

The present invention provides an improved single lumen vascular access port and/or an associated surgical method, where the port contains at least two different needle access points or apertures, at least one of which is a standard superficial penetrable flexible septum or diaphragm that is located close to the skin surface for routine clinical access (perpendicular- or vertical-or top-access aperture) to be entered at or near 90 degrees relative to an internal-chamber floor surface, and at least a second separate parallel-access or lateral access aperture with a penetrable septum (to be entered parallel to or at an acute angle preferably less than about 40° relative to the port chamber floor) to facilitate the ergonomic advancement through the port chamber (then into the outlet tube and an attached intravascular catheter) of various intravascular wires, brushes, devices or tools for maintaining secondary port patency by removing or dislodging intraluminal clot and or an adherent fibrin sheath attached to the intravascular catheter. The lateral access aperture may have a steeper angle relative to the port floor, up to about 70°, in order to improve aperture palpation and identification along with the ergonomic needle advancement into the lateral access aperture, particularly important for the reliable execution of the high flow applications of apheresis and dialysis as contemplated herein. The outlet tube is similarly angled to maintain a collinear relationship with the lateral access aperture such that an access needle advanced through said lateral access aperture can readily traverse the port chamber to enter the outlet aperture and outlet tube in a straight-line pathway (lateral or straight-line access aperture). In addition, the angled more inferiorly positioned outlet stem lowers the overall center of gravity of the port body and limits tipping or tilting of the implanted device which is accentuated by drag created by the attached catheter to said outlet stem.

The present invention provides an improved single lumen vascular access port and/or an associated surgical method, where the port contains two different needle access points or apertures, one of which is a standard superficial perpendicular- or top-access aperture with a penetrable flexible septum that is located close to the skin surface for routine clinical access for low-flow applications (needle placed at least substantially perpendicular to the upper and lower walls of the port device as well as the adjacent overlying skin), and a second, separate lateral access aperture or straight-line-access aperture for high-flow applications and other interventions (needle placement or insertion straight across the internal chamber of the port device to an outlet aperture in the internal chamber, parallel to or at an acute angle—preferably a small or shallow angle—relative to the port chamber floor and lower port wall) with a penetrable septum to enable fluoroscopic repositioning of a previously placed undesirably migrated intravascular port catheter tip position by advancement of a needle and subsequently a steerable wire through the lateral sidewall or straight-line-access aperture and subsequently the catheter under fluoroscopy.

The present invention provides an improved single lumen vascular access port and/or an associated surgical method, where the port contains two different needle access points or apertures, one of which is a standard superficial penetrable flexible septum or diaphragm that is located close to the skin surface for routine clinical access (perpendicular- or top-access aperture for low-flow applications), and a second separate lateral access aperture or straight-line-access aperture with a penetrable septum to enhance the safety of port removal over a wire preventing inadvertent cutting or dislodgement of the port catheter with resultant intravascular foreign body creation.

The present invention contemplates an improved single lumen vascular access port and/or an associated surgical method, where the port contains two different needle access points or apertures, one of which is a standard superficial penetrable flexible septum or diaphragm that is located close to the skin surface for routine clinical access (perpendicular- or top-access aperture for low-flow-rate applications), and a second separate lateral access aperture or straight-line-access aperture with a penetrable septum to enable an initial wire directed port catheter placement, helping to both steer the catheter to a given vascular location and improving catheter pushability during deployment, or to help remedy immediate or delayed port catheter placement complications such as a redundant and/or kinked often extravascular subcutaneous catheter loop.

The present invention provides an improved single lumen vascular access port body design and/or an associated surgical method, where the port body contains two different needle access points or apertures, one of which is a standard superficial penetrable flexible septum or diaphragm that is located close to the skin surface for routine clinical access for low-flow applications (top- or perpendicular-access aperture), and a second separate lateral access aperture or straight-line-access aperture with a penetrable septum to enable over-the-wire port exchange for a malfunctioning port or to exchange it for different tunnel intravascular access apparatus such as a Hickman catheter or plasmapheresis catheter.

The present invention provides an improved vascular access port and/or an associated surgical method to accommodate various wires or endovascular devices so they can be used to their best mechanical advantage or working angle to help maintain secondary port patency or facilitate port exchange (at or near 180 degrees) via the straight-line-access aperture.

Pursuant to a feature of the present invention, in traversing the straight-line access a needle crosses the internal chamber of the port device along a linear path or direction to traverse an output aperture on an opposite of the chamber. The straight line may be angled at an acute angle relative to the vertical or normal (and necessarily at an acute angle to the skin surface and the horizontal or upper and lower walls or floor of the port device) so that the linear path of needle insertion inclines downwardly from the lateral access aperture to the outlet aperture and contiguous outlet tube. The collinear orientation of the lateral access aperture and outlet tube facilitates trans-chamber needle entrance into the outlet aperture and outlet tube or alternatively into a port body channel contiguous with the outlet aperture and the outlet tube. The lateral access aperture may have an angle relative to the port floor or lower wall of up to approximately 70 degrees in order to improve the ergonomics of reliable lateral access aperture identification and access needle placement. The outlet aperture and contiguous outlet tube being positioned at a lower end of the port body militates against tipping or pivoting of the port device in response to catheter drag on the outlet tube. The outlet tube being parallel to the angled straight-line access needle path may be similarly angled relative to the vertical and acutely angled relative to the floor of the port chamber, be it a single or a double lumen version of the devices described herein.

Preferably, the outlet aperture communicates with an outlet tube or stem that, at least on an upstream side contiguous with the outlet aperture and the internal chamber, is co-linear with the linear path or direction of access of the needle from the lateral sidewall or straight-line-access aperture to the chamber outlet aperture. At the upstream side, the outlet tube (or in a contiguous adjacent channel in the port body communicating with the internal chamber) is provided internally (within its lumen) with a male element (such as a rib, a nub, a lug, a tooth, etc.) or a female element (typically a groove or a recess) that mates with a corresponding female or male element on the access needle to temporarily lock or fix the needle to the port body. The coupling or locking element(s) may be located in the outlet tube itself or upstream within a port chamber channel, opposite the lateral access aperture, in contiguity with the outlet tube or stem. The straight-line access needle, once locked in place, eliminates turbulence and therefore limitations to high flow applications inherent to utilizing the top or perpendicular access aperture for this purpose. A straight tube or conduit has lower frictional losses or turbulence relative to a capacious chamber or angled conduit. The use of a rigid needle for this purpose reduces the risk of kinking inherent in utilizing deformable thin walled plastics (angiocatheter) for access, particularly if advanced at an angle. The interlocking needle or snap lock mechanism facilitates needle stability and creates a tight seal enabling high-flow procedures (such as apheresis or dialysis), preventing backflow. At least one of the two male and female components of the snap lock mechanism may be composed of an elastomeric material such as plastic. A number of options are available when attempting to utilize a port for high flow access procedures such as apheresis or dialysis: two separate single lumen ports placed with one serving as the venous access and the other for the venous return; single lumen port placement, serving as the venous access and using peripheral intravenous cannulation for the venous return; or placement of a dual lumen port with both venous access and return capabilities. The interlocking needle mechanism also provides stability for other contemplated methods and procedures described herein such as wire advancement through the attached intravascular catheter facilitating port placement, port catheter repositioning, maintenance of secondary patency, port removal, and over the wire port exchange.

The present invention provides an improved vascular access port body shape, port chamber shape, and outlet aperture configuration to best guide the placement of various wires, devices, or tools, via the aforementioned lateral sidewall or straight-line-access aperture or apertures through the port chamber, into the port chamber outlet aperture, and subsequently the attached exiting intravascular catheter.

The present invention provides an improved vascular access port and/or an associated surgical method to facilitate fibrin sheath striping (with an intravascular loop snare) over a needle and subsequently a wire placed through the straight-line-access port aperture to decrease the likelihood of intravascular catheter fragmentation and intravascular foreign body creation, thereby restoring or maintaining port catheter patency in a more effective and safe manner.

The present invention provides an improved vascular access port and/or an associated surgical method wherein a second port aperture or penetrable septum allows for an alternative skin puncture site, for the administration of medications, if one of the apertures is less desirable for routine clinical use (hematoma or local skin site wound or irritation for example), or for the simultaneous administration of a second miscible or compatible medication.

The present invention provides an improved double lumen vascular access port and/or an associated surgical method, where the port contains a total of four different needle access points or apertures, specifically two juxtaposed perpendicular-access adjoining apertures for routine clinical use and two adjoining straight-line-access apertures for maintaining secondary patency enabling all of the aforementioned properties, functions, and methods of the single lumen device. The paths of straight-line access may be angled in towards one another, to provide space at the outside for manipulating two needles simultaneously, if necessary. Also the paths of straight-line access may be angled downwardly to place the access apertures closer to the skin surface to thereby facilitate aperture locating and needle deployment. Such a double lumen vascular access port may be used in carrying out high flow applications such as dialysis with both inlet and outlet needles in addition to apheresis.

A single lumen access port pursuant to the present invention contains at least two different needle access points or apertures, at least one of which is a standard superficial penetrable flexible septum or diaphragm that is located close to the skin surface for routine clinical access (perpendicular- or vertical- or top-access aperture), and a second separate straight-line-access aperture or lateral access aperture with a penetrable septum (to be entered parallel to or at an acute angle relative to the port chamber floor) to facilitate the placement of various intravascular wires, devices or tools in order to help maintain secondary port patency, facilitate initial port placement, improve the safety of port removal, enable over-the-wire port exchange, and high-flow access (apheresis and dialysis). Physicians will primarily utilize the secondary, straight-line-access or working aperture for the aforementioned purposes under fluoroscopic guidance, while nurses may primarily use the perpendicular-access aperture for routine clinical use (generally, applications with low flow rates) without fluoroscopy, the latter in an identical manner to ports currently in the market place. Specialized nurses, such as apheresis or dialysis nurse may also be trained to access the lateral or straight-line access aperture for high flow applications such as apheresis or dialysis. The lateral or straight-line access aperture, which is located typically on the sidewall of the port body opposite the exiting outlet tube and catheter, allows for the advancement of various devices including but not limited to a wire at the optimal working angle (at or near 180 degrees) to enter the exiting intravascular catheter. While a lateral access port is typically disposed in a sidewall of a port body, the word "lateral" denotes the port as being "to the side" of a routine-maintenance access port in a top or upper wall of a vascular access port body. The shallow angle lateral or straight-line access aperture provides the ideal angle of approach for advancing a needle and subsequently a wire or other devices in order to engage or enter the exiting outlet tube and subsequently the intravascular catheter, located on the opposite end or side of the port body in order to perform various intravascular procedures with the goal of restoring or improving vascular port patency and function. The lateral or straight-line access aperture (which may be disposed in a parallel or angled plane, relative to the lower wall or floor of the port device) provides the ideal angle of approach for wire advancement, manipulation and steerability both before and after entering the exiting catheter and ultimately within the vascular system. The goal of the design is to not substantively alter the technique or equipment required for routine clinical port access by nurses or other healthcare personnel relative to current devices. Therefore there is no need for new training or new equipment for routine access purposes.

The port body shape may be configured to optimally accommodate the lateral or straight-line access aperture(s) and guide the placement of initially a needle and subsequently various wires, devices, or tools, via the aforementioned straight-line-access aperture or apertures through the port body into the exiting outlet tube and ultimately the intravascular catheter. For instance, the port body may be wider opposite the exiting catheter in order to accommodate the placement of one or more straight-line-access apertures. One version of the port may therefore assume a horseshoe shape with a more tapered or conical end located on the exiting catheter side and an opposite wider end incorporating the straight-line-access aperture or apertures. An overall rounded port chamber may passively help guide the needle toward said conical end. Rounding of the edges of the port body along the wider horseshoe-shaped end may reduce friction for easier port placement, removal, or exchange. Alternatively the port body may assume on an outer side more of a smooth elongated, oblong, or teardrop shape in order to reduce friction during port removal or exchange after scar tissue has developed, while placing traction on the port with a clamp. A more conical or tapered inner contour of the port chamber opposite the straight-line-access working aperture or apertures facilitates or helps guide the entrance of the needle into the exiting outlet tube and ultimately a wire into the intravascular catheter and subsequently into the vascular system. Alternatively the port body and or chamber may be configured in a more conventional cylindrical shape, frusto-conical shape, or preferably an ellipsoid or spheroid shape (true sphere or oblate sphere) since this latter design fosters circular motion and mixing of the injected fluids, minimizing dead space within the chamber. Acute edges and corners result in sudden directional changes in fluid flow through the port chamber, creating dead zones, cell shearing, platelet activation and clotting. Fluoroscopic guidance may assist placement of an access needle into the rounded or semicircular straight-line-access port aperture or diaphragm and subsequently direct the needle into the outlet tube while maintaining the most ergonomic shape for minimizing dead space and activation of the clotting cascade within the port chamber. Palpable features, either a concavity or an elevation incorporated into the straight-line-access or lateral access aperture, facilitates needle access without fluoroscopic guidance. For example, a skin covered frusto-conical feature (palpable depression, concavity, or inwardly tapering recess) helps guide the needle toward a smaller deeper inner septum, at its junction with the port chamber wall, in alignment with the outlet aperture on the opposite port chamber wall.

Different outer port body shapes and inner chamber sizes and shapes may confer different advantages. For example, the outer port body can be frusto-conical, elliptic frusto-conical, ellipsoidal ovoid, torpedo shaped, or teardrop shaped but contain a smaller inner cylindrical, frusto-conical, elliptic frusto-conical, spheroid or ellipsoid port chamber (constituting similar or differing shapes of the respective port body and chamber) which allows room for a frusto-conical, elliptic frusto-conical, frusto-pyramidal or other shaped skin covered palpable depression or inwardly tapering recess, leading to a smaller inner septum, serving to guide or align the access needle with the outlet aperture and outlet tube. The wider outer component is easier to palpate and enter while the smaller inner portion more effectively guides or aligns the access needle to the outlet aperture on the opposite side of the chamber. For example, an outer frusto-conical port body shape with a flat dome optimizes palpation for low flow vertical access while a spheroid (true sphere or oblate sphere) or ellipsoid inner chamber optimizes flow dynamics within the chamber, limiting eddy currents and thereby minimizing intra-chamber thrombus formation. Differing geometric shapes and sizes of the respective port body and chamber may also enhance palpable lateral access aperture features such as allowing room for the incorporation of the inwardly tapering recess or palpable depression, leading to a smaller inner septum, serving to guide or align the access needle with the outlet aperture and outlet tube.

The straight-line-access needle may be a non-coring straight Huber needle. In that case, however, the almost perpendicular orientation of the cutting edge while allowing for the needle to separate or part the silicone likely results in some deflection of a wire placed through the needle. Using a Seldinger needle may obviate this potential mechanical disadvantage, this being a straight beveled needle containing a beveled solid stylet that projects out from the end of the needle, simultaneously preventing coring of the silicone diaphragm.

In one embodiment of the invention, a port body or a portion thereof in accordance with the invention is at least partially radiopaque while the respective perpendicular-access and straight-line-access apertures, along with the outlet aperture, are radiolucent thereby facilitating fluoroscopically guided needle placement through either aperture but may be particularly useful for the straight-line-access aperture or apertures, in preparation for various vascular interventions with the primary goal of maintaining secondary port patency or for performing high flow procedures such as plasmapheresis or dialysis. For example only the sidewalls of the port body may be radiopaque or partially radiopaque while both the perpendicular-access aperture and the straight-line access aperture may be radiolucent along with the outlet aperture. The straight-line-access and or perpendicular-access apertures may have enhanced radiopaque edges to facilitate fluoroscopic needle placement. Alternatively, the port body may be largely radiolucent with complete or partial radiopaque edges or rims added to the otherwise radiolucent straight-line-access aperture, perpendicular-access aperture, and outlet aperture to facilitate fluoroscopic needle placement as well. This is an important port body design feature since accessing the straight-line-access aperture(s) may be more difficult than the standard perpendicular-access aperture(s) by palpation alone and once accessed any procedure to remedy malfunction of the vascular access port may invariably be guided by fluoroscopy, typically performed by a physician such as a radiologist.

The perpendicular-access aperture, whether in current clinical vascular access devices or the device described herein, is optimized for needle access by palpation alone and is typically performed by a nurse; however, fluoroscopy can be also utilized for difficult clinical scenarios either for confirmation of correct needle position or fluoroscopically guided direct needle access. The straight-line-access aperture only need be occasionally accessed for the primary purpose of high flow applications such as apheresis or dialysis, addressing vascular port malfunction, catheter repositioning, port removal or port exchange. However, the straight-line-access aperture may also be used for routine clinical use, if the perpendicular-access aperture or septum is inaccessible due to overlying cutaneous or subcutaneous pathology, or if simultaneous administration of miscible or compatible medications is desirable. The straight-line-access aperture may be accessed by palpation of various features described herein or by fluoroscopy as needed, if difficultly is encountered by a specialized apheresis nurse for example, or if a physician is performing one of a number or fluoroscopically guided interventions described herein.

These devices used to maintain port patency and optimal function include but are not limited to steerable wires, microbrushes, and microballons and are typically placed under fluoroscopic guidance by a physician such as a radiologist. The devices used to remedy catheter malfunction have been previously described for accessible vascular access devices such as tunneled Hickman catheters but the novel straight-line-access aperture and associated methods described herein enable their effective use in the setting of an otherwise inaccessible subcutaneous vascular access port. The unique aforementioned second, straight-line-access aperture or apertures and port body and port outlet design facilitates the placement and usage of such devices. These devices may be placed through a larger 18 gauge non-coring Huber or stylet-containing Seldinger needle is then typically used to access the second perpendicular-access port for routine clinical purposes (22 to 19 gauge) such as the administration of drugs. Utilization of the straight-line-access aperture and larger gauge and possibly longer non-coring Huber or stylet-containing Seldinger needle may only be needed on occasion to address vascular port malfunction or perform a high flow procedure such as apheresis or dialysis. Slidable wire advancement through the straight-line-access aperture via an 18 gauge Huber or Seldinger needle may be used to recanalize an occluded port catheter lumen and or disrupt a fibrin sheath surrounding the end of the port catheter in lieu of or in combination with TPA. A steerable wire may also be utilized to reposition a malpositioned catheter tip, which can migrate into an undesirable position such as the internal jugular vein for example. The ideal position for the catheter tip is generally considered to be the superior vena cava or the right atrium. Wire advancement into the inferior vena cava after placement through the straight-line-access aperture and catheter allows for safer fibrin sheath stripping relative to current methods. Femoral vein puncture allows for placement of an angiographic catheter and subsequently a snare around the more superiorly located wire and contiguous port catheter from an inferior approach under fluoroscopy. The snare can then tightened around port catheter and traction can then be applied such that the fibrin sheath or biofilm can be removed. The wire allows for safer and easier capture of the port catheter by securing the longer wire in the inferior vena cava away from the right atrium. More importantly the support of the wire lessens the likelihood and consequences of inadvertent fracturing of the port catheter. If the catheter were to inadvertently fracture from the fibrin sheath striping procedure, the loose piece may still be located on the wire and may be removed from the femoral access via the snare. Fibrin sheath striping without the use of a concomitant wire can result in a loose intravascular foreign body, which can then migrate to the heart or pulmonary circulation. A silicon or latex microballoon may also be advanced through the 18 gauge Huber or Seldinger needle with subsequent inflation just distal to the port catheter tip in order to disrupt a surrounding fibrin sheath or biofilm.

The ability to advance a needle and subsequently a wire through the straight-line-access aperture(s) and the port's internal chamber can allow for more reliable initial wire-directed catheter placement or to help remedy immediate or delayed subcutaneous port-catheter placement complications such as a redundant and or kinked catheter loop in the extravascular soft tissues.

A separate second, lateral or straight-line access aperture with a penetrable septum enhances the safety of port removal over a wire preventing inadvertent cutting or dislodgement of the port catheter with resultant intravascular foreign body creation. Identification and safe removal of the catheter can at times be difficult secondary to abundant adherent surrounding scar tissue. The placement of a needle and then a wire through the straight-line-access port and catheter enhances the operator's ability to palpate and safely dissect around the catheter in order to remove it, simultaneously lessening the likelihood of inadvertently transecting the catheter and resulting in an intravascular foreign body. If transection of the catheter were to occur, albeit unlikely because of the traversing wire, the fragment may be retrievable with an intravascular snare since the wire may be securing it.

A separate lateral or straight-line access aperture (to be entered parallel to or at a acute angle relative to the port chamber floor) with a penetrable septum enables over-the-wire port exchange for a malfunctioning port thereby increasing the speed and efficiency of replacing a malfunctioning port. Typically, port revision requires stepwise removal of the malfunctioning port and then stepwise replacement with a new port. Placement of a needle and subsequently a wire through the straight-line-access aperture opposite the working end of the port catheter may enable exchange of a malfunctioning port over a wire after freeing the existing port from surrounding scar tissue with blunt dissection by one or more incisions. A peel away sheath may initially be placed over the wire, facilitating placement of the new port and attached catheter by reducing friction. The initial peel-away sheath placement also tends to allow time for sizing of the length of the new port catheter relative to the length of the old one prior to its placement into the venous system, over the wire and through the peel away sheath.

A double lumen vascular access port in accordance with the present invention contains a total of four different needle access points or apertures, specifically two juxtaposed perpendicular-access apertures for routine clinical use and two adjoining or adjacent straight-line-access apertures for remedying port catheter malfunction. A midline vertical or perpendicular septum is provided to divide the internal chamber of the port body into respective port body chambers. A palpable ridge or alternatively a depression may be located between two juxtaposed port septa or diaphragms to facilitate needle placement into the respective port body chambers by palpation. The two adjacent straight-line-access apertures, located on the side of the double lumen port body opposite the exiting catheter, allow for the advancement of various devices including but not limited to two wires at preferably a shallow angle (acute angle) or the optimal working angle, namely a straight angle (180 degrees) to enter respective halves of the exiting intravascular catheter which contains a midline septum characteristic of double lumen Portacath design. The straight-line-access apertures provide the ideal angle of approach for advancing needles into the respective semicircular or semicylindrical outlet apertures, and subsequently wires or other devices in order to engage or enter the exiting respective halves of the intravascular catheter, located on the port body opposite the straight-line-access apertures in order to perform various intravascular procedures with the goal of restoring or improving vascular port patency or to perform high flow vascular procedures such as plasmapheresis or dialysis. The more conical or tapered shapes of the internal surfaces of the respective port body chambers, separated by a midline septum, opposite the respective straight-line-access working apertures, facilitate or help guide the entrance of the two respective straight-line access needles or alternatively wires into the respective outlet apertures, subsequently gaining access to the two halves of the exiting catheter and the vascular system, under fluoroscopy, for performance of the various methods described herein. The straight-line-access apertures, aligned with the respective outlet apertures, provide the ideal angle of approach for needle and or wire advancement, along with wire manipulation and steerability both before and after entering the exiting catheter and ultimately within the vascular system.

A special needle design consisting of a semicircular (or semi-cylindrical) cannula and a semicircular (or semi-cylindrical) yet pointed stylet may be provided in order to directly engage the semicircular outlet aperture, to enable temporary locking of the cannula to the port body and outlet tube particularly for high-flow procedures. High-flow applications such as apheresis and dialysis require direct needle engagement, coupled with a reversible locking mechanism (no back flow), into the respective halves of the semicircular outlet tubes, necessitating the use of corresponding semicircular cannula and semicircular pointed inner stylet. A traditional cylindrical cannula with pointed stylet (Seldinger needle) may be used to direct a wire into a semicircular outlet aperture (s) without directly seating or locking the needle to the outlet aperture, in any low-flow applications such as maintenance of secondary port patency. Alternatively, to enable use of conventional cylindrical needle assemblies with a double lumen vascular access port in accordance with the present invention, the vascular access port may be provided with (1) dual outlet tubes having cylindrical lumens, (2) a dual-flow outlet tube with a proximal end portion having two cylindrical lumens and a distal end portion having semi-cylindrical lumens, and (3) a thickened port body wall having two cylindrical lumens communicating with semi-cylindrical lumens in the outlet tube.

The port body shape may be configured to optimally accommodate the straight-line-access apertures and guide the placement of initially a needle and subsequently various wires, devices, or tools, via the aforementioned straight-line-access aperture or apertures through the port body into the exiting outlet tube and ultimately the intravascular catheter. For instance, the port body may be wider opposite the exiting catheter in order to accommodate the placement of one or more straight-line access apertures. One version of the port may therefore assume a horseshoe shape with a more tapered or conical end located on the exiting catheter side and an opposite wider end incorporating the straight-line-access aperture or apertures. An overall rounded port chamber may passively help guide the needle toward said conical end. Rounding of the edges of the port body along the wider horseshoe-shaped end may reduce friction for easier port placement, removal, or exchange. Alternatively the port body may assume on an outer side an elongated, oval, or teardrop shape in order to reduce friction during port removal or exchange after scar tissue has developed, with traction being placed on the port by means of a clamp. A conical or tapered inner contour of the port chamber wall opposite the straight-line-access working aperture or apertures facilitates or helps guide the entrance of the needle or wire into the exiting outlet tube and ultimately a wire into the intravascular catheter and subsequently into the vascular system.

Alternatively, the body of a dual-chamber vascular access port may be configured in a more conventional manner with two cylindrical or preferably oval or round spheroid chambers (true spheres or oblate spheres) separated by a palpable ridgeline since this design fosters circular motion and mixing of the injected fluids minimizing dead space within the chamber. Acute edges and corners result in sudden directional changes in fluid flow through the port chamber, creating dead zones, cell shearing, platelet activation and clotting. Fluoroscopic guidance alone enables placement of an access needle into the rounded or semicircular straight-line-access port aperture or diaphragm and subsequently into outlet aperture and outlet tube after traversing the port chamber, then threading a wire into the exiting catheter while maintaining the most ergonomic shape for minimizing dead space and activation of the clotting cascade within the port chamber. The present design does not substantively alter the technique or equipment required for routine clinical dual lumen port access by nurses or other healthcare personnel relative to current devices. Therefore there is no need for new training or new equipment for routine perpendicular-access purposes.

In another embodiment of the invention, the double lumen port body or a portion thereof in accordance with the invention is at least partially radiopaque while the respective perpendicular-access and straight-line-access apertures, along with the outlet apertures, are radiolucent thereby facilitating fluoroscopically guided needle placement through either aperture but particularly with straight-line-access aperture or apertures, in preparation for various vascular interventions with the primary goal of maintaining secondary port patency or for performing high flow procedures such as plasmapheresis or dialysis. For example only the sidewalls of the port body may be radiopaque or partially radiopaque while both the perpendicular-access apertures and the straight-line access apertures may be radiolucent along with the respective outlet apertures. Or the straight-line-access apertures, perpendicular-access apertures, or outlet apertures, may have enhanced radiopaque edges to facilitate fluoroscopic needle placement. Alternatively, the double lumen port body may be largely radiolucent with complete or partial radiopaque edges or rims provided for the otherwise radiolucent straight-line-access apertures, perpendicular-access apertures, or outlet apertures, to facilitate fluoroscopic needle placement. This is an important port body design feature since accessing the straight-line-access aperture(s) may be more difficult in some cases than the standard perpendicular-access aperture(s) when using palpation alone and once accessed any procedure to remedy malfunction of the vascular access port may invariably be guided by fluoroscopy, typically performed by a physician such as a radiologist.

Accordingly, an implantable vascular access port may be provided with varying degrees of radio-opacity or radio-translucency to facilitate access under fluoroscopic guidance. Where (i) a major portion of the port body has a first predetermined degree of radio-opacity, (ii) the lateral-access and outlet apertures exhibit a second predetermined degree of radio-opacity, and (iii) the port body has edge regions extending about and defining the lateral-access and outlet apertures, the edge regions having a third predetermined degree of radio-opacity, then at least one of the second and the third predetermined degrees of radio-opacity differs substantially from the first predetermined degree of radio-opacity. Optionally, the vertical-access aperture may also be distinguished by the second predetermined degree of radio-opacity or by an edge region of the third predetermined degree of radio-opacity. Radio-opacity may vary between essentially zero (radio-translucence) and essentially 100% (completely radio-opaque). The degrees of radio-opacity are understood as qualitative in that each degree of radio-opacity can lie within a numerical or percentage range but where the degrees differ for enhancing visualization, the respective ranges of radio-opacity do not overlap. Thus the various physical features are fluoroscopically distinguishable. It is to be understood that the radio-opacity of a lateral access aperture or a top (vertical) access aperture is the same as, and determined by, the radio-opacity of the associated septum.

In summary a double lumen access port in accordance with the present invention contains a total of four different needle access points or apertures, specifically two juxtaposed perpendicular-access apertures for routine clinical use and two adjoining straight-line-access apertures for high flow applications such as plasmapheresis or dialysis as well as maintaining secondary patency enabling all of the aforementioned properties, functions, and methods of the single lumen device.

In a high-flow vascular access method in accordance with the present invention, exemplarily for apheresis or dialysis, one attaches a catheter to a hollow outlet tube of a vascular access port, and extending or deploys the catheter in a central venous system of the patient. One inserts a distal end portion of a non-coring needle assembly along a straight-line path through a lateral access septum and aperture, across an internal chamber of the access port, and through an outlet aperture into the hollow outlet tube. One releasably locks a cannula of the non-coring needle assembly at least indirectly to the hollow outlet tube and removes a stylet needle from the non-coring needle assembly after inserting of the distal end portion of the non-coring needle assembly through the lateral access septum. Thereafter one guides blood at a substantial flow rate from the central venous system of the patient through the catheter, the hollow outlet tube, and the cannula. One conducts an apheresis or dialysis procedure on the blood flowing from the central venous system of the patient through the catheter, the hollow outlet tube, and the cannula and thereafter returns the blood to the vascular system of the patient.

The blood may be returned to the patient's vascular system by directing the blood via a peripheral or central needle cannulation or a separate implanted vascular access port. Alternatively, the vascular access port through which blood is withdrawn from the patient may be a dual lumen port with both venous access and return capabilities. In the latter case, the port body of the dual lumen port preferably has (i) at least two internal chambers, (ii) at least two outlet apertures each in communication with a respective one of the at least two internal chambers, (iii) at least two lateral access apertures each defining a respective straight-line-access path or direction to a respective one of the at least two outlet apertures, (iv) at least two top access apertures each formed in the upper wall and defining a respective perpendicular- or vertical-access path or direction substantially perpendicular to the upper wall and the lower or floor wall, (v) at least two first septum coverings closing respective ones of the at least two lateral access apertures, (vi) at least two second septum coverings closing respective ones of the at least one top access apertures, and (vii) at least hollow outlet tube passageways in fluid communication with respective ones of the at least two internal chambers and respective ones of the at least two outlet apertures.

A special needle design consisting of a semicircular (or semi-cylindrical) cannula and a semicircular (or semi-cylindrical) yet pointed stylet may be provided in order to directly engage the semicircular outlet aperture, to enable temporary locking of the cannula to the port body and outlet tube particularly for high-flow procedures. Again, high-flow applications such as apheresis and dialysis require direct needle engagement, coupled with a reversible locking mechanism (no back flow), into the respective halves of conventionally semicircular outlet tubes. To enable use of conventional cylindrical needle assemblies with a double lumen vascular access port, the vascular access port may be provided with (1) dual outlet tubes having cylindrical lumens, (2) a dual-flow outlet tube with a proximal end portion having two cylindrical lumens and a distal end portion having semi-cylindrical lumens, and (3) a thickened port body wall having two cylindrical lumens communicating with semi-cylindrical lumens in the outlet tube. Alternatively, a semi-cylindrical stylet-cannula needle may be used for releasably lockable engagement of the needle cannula with a semicircular outlet-tube lumen.

DETAILED DESCRIPTION

Figure 1:
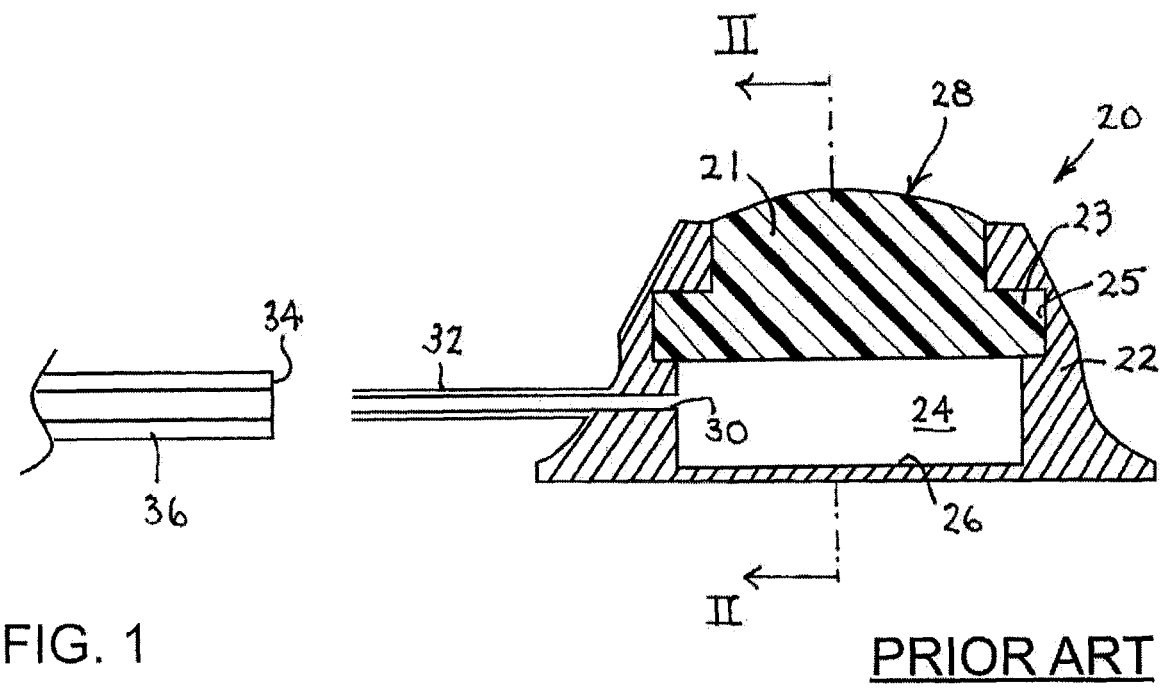
FIG. 1 is a sagittal cross-section view of an access port apparatus according to a prior art design.

As used herein the terms "perpendicular-access" and "straight-line-access" refer to respective angles of placement or insertion of a needle through a skin surface into a vascular access port implanted beneath that skin surface. The term "perpendicular-access" signifies a direction of needle placement or insertion that is substantially, or at least mostly, perpendicular to a floor surface of an internal chamber of the access port as well as the skin overlying the perpendicular-access septum of the port (in contradistinction to the skin covering sidewalls of the port which may be sloped or angled). A perpendicular-access aperture in a port body as described herein is covered by a penetrable flexible septum located close to the skin surface for routine clinical access. Concomitantly, a perpendicular-access aperture is located in an upper surface of an implantable vascular port, next to the skin surface, and may be termed a "top access aperture."

Ideally, a perpendicular-access needle insertion line or direction is oriented 90° relative to the floor surface of a port body internal chamber or the lower wall of the port body. However, in practice the needle insertion direction may deviate from 90° by an angle of 10° to 20° from the exact perpendicularity.

Concomitantly the term "straight-line access" signifies a direction of needle placement or insertion that is at least partially parallel to the floor or lower wall of the implanted vascular access port, or inclined with respect to that floor or lower wall preferably at an angle of less than about 40° but possibly up to about 70°. The port sidewall, as well as the skin covering the port sidewall, may be sloped, or angled relative to the floor of the port body. A straight-line-access aperture is configured for placement or penetration of a needle preferably in parallel with, or in near parallel relation to, the (preferably flat) port floor. However, a straight-line access path, exemplarily for high-flow-rate access applications such as apheresis and dialysis, may be inclined by an angle of up to about 70° relative to the lower wall of the port body. The straight-line access path is collinear with the outlet tube on the opposite side of the port body to facilitate trans-chamber needle engagement in the outlet tube. The outlet tube or the port body is provided with a reversible needle locking mechanism for the performance of the high flow procedures such as apheresis and dialysis as well as stable needle positioning for the performance of other methods described herein.

A vascular access "port body" is contemplated herein to denote a housing or casing made of a material resistant to penetration by a medical needle. The body of a vascular access port is provided with openings or apertures through which a needle may be inserted. A "lateral access aperture" or "straight-line access aperture" is used herein to denote an opening so positioned in a port body as to enable a straight-line access to the outlet tube on the opposite side of the port chamber. While a lateral access port is typically disposed in a sidewall of a port body, the word "lateral" as used herein denotes an access port or aperture as being "to the side" of a routine-maintenance access port in a top or upper wall of a vascular access port body. Accordingly a lateral access port may be located in the upper wall of a vascular access port body, laterally of a main or routine access aperture. However, it is contemplated that a lateral access port, to effectively facilitate certain applications, such as high-flow venous access for dialysis and apheresis defines a straight-line access path oriented between 0 and about 70 degrees from the horizontal lower wall of the port body and concomitantly the floor surface of the pertinent internal chamber, collinear with the outlet tube on the opposite side of he port chamber.

A "lateral access aperture" or "straight-line access aperture" in a port body as described herein is covered by a penetrable flexible septum located close to the skin surface for enabling fluoroscopic repositioning of a previously placed, undesirably migrated intravascular port and/or an associated catheter tip by advancement of a needle through the lateral sidewall- or straight-line-access aperture, then through said port body, into the outlet stem, and subsequently advancing a steerable wire through the needle into an attached catheter under fluoroscopy.

The term "outwardly tapering chamber extension" is used herein to denote a recess or ancillary cavity within a port body that communicates on an inner side with a main internal port chamber and that forms an outlet aperture communicating with an outlet tube configured to extend into a vein of a patient upon implantation or deployment of the associated vascular access port into a patient. The outlet aperture may be defined as the entirety of the recess or ancillary cavity between the internal chamber proper and the outlet tube or may be limited, in the alternative, to one plane, such as the upstream end or the downstream end of the recess or cavity. In the present disclosure, it is the last alternative that is generally contemplated.

The term "inwardly tapering recess" is used herein to denote a depression, concavity, or recess extending through a port body from an outer surface thereof to an internal cavity of the port body. The depression, concavity, or recess has a transverse dimension (width, diameter) that is less on the inner side than the outer side. The depression, concavity, or recess may be hemispherical, ovoid, elliptical, hyperbolic, etc., and have a concomitantly circular cross-section or may be pyramidal with a polygonal cross-section. Other tapering geometries may be utilized as well. The inwardly tapering recess within the port body typically comprises the lateral access aperture, provided at an inner end with a self-sealing septum or membrane for needle penetration at its junction with the inner chamber wall.

The word "needle" and the term "needle assembly" as used herein with reference to high-flow vascular access applications such as apheresis and dialysis denotes a non-coring access needle assembly comprising an outer cannula and a sharp inner stylet traversing a longitudinal lumen of the cannula. The cannula and corresponding pointed inner stylet can be either cylindrical or semi-cylindrical (with a D-shaped transverse cross-section) depending on the shape of the lumen of the corresponding outlet tube. A semi-cylindrical cannula and stylet shape is required for one double lumen port described herein (see, e.g., FIG. 15) while a cylindrical needle may be utilized for the various single lumen versions and another double lumen embodiment with outwardly angled lateral access apertures (see FIG. 44). The stylet and cannula are preferably made of a metal or alloy material. The cannula is formed proximate a distal end with an annular groove or one or more beads, optionally annular, for cooperating in a reversible snap-lock fit with a resilient bead or groove projecting from an inner surface of an outlet tube or of a tubular passageway inside the wall of a port body of an implantable vascular access port as described herein. The stylet is used to puncture a self-sealing membrane or septum and is removed from the cannula once the cannula is releasably locked to an outlet tube or port body passageway.

A port body of a vascular access port as described herein is preferably made for the most part of an at least partially radio-opaque material. Ideally the material is not completely opaque so as to enable visualization of the internal chamber and a needle's progress through the chamber toward the outlet aperture during a vascular access procedure. The port body may have small portions, for instance, along edge regions surrounding the lateral access, top access, and outlet apertures, which have a perceptibly different radio-opacity than the main portion of the port body to facilitate visual detection of the apertures and septa during access procedures. Typically, but not necessarily, the septa are made of a radiolucent material. In another version the port body of a vascular access port as described herein is preferably made for the most part of a radiolucent material so as to enable visualization of a needle's progress through the chamber toward the outlet aperture during a vascular access procedure. The edges surrounding the lateral access, top access, and outlet apertures, of said radiolucent port body are at least partially radiopaque. Typically again, but not necessarily, the septa are made of a radiolucent material.

An implantable vascular port apparatus or device 52 as depicted in FIGS. 5-11 includes a main port body 56 having an internal chamber 54 formed therein. The main port body 56 may have various shapes including but not limited to frusto-conical, elliptic frusto-conical, teardrop shaped, torpedo shaped, horseshoe shaped, and ovoid. The port body 56 and port chamber 54 may be of similar or differing shapes respectively. Possible chamber shapes include but are not limited to cylindrical, frusto-conical, elliptic frusto-conical, ellipsoidal, and spheroidal. FIGS. 5-11 depict an elliptic frusto-conical port body 56 and port chamber 54. The main port body 56 has two penetrable septa 58 and 60 extending across and closing respective apertures 158 and 160: a perpendicular- or top-access septum 58 in aperture 158 similar to conventional ports as well as a novel straight-line- or lateral sidewall-access septum 60 in aperture 160 primary for the performance of various interventions to facilitate initial port placement, port catheter repositioning, maintenance of secondary port patency, port removal, high-flow applications, and port exchange. The radiolucent septa 58 and 60 are formed from a resiliently deformable material such as silicone elastomer. The perpendicular- or top-access and straight-line- or lateral sidewall-access septa 58 and 60 each include a respective thickened central portion 41a and 41b as shown in FIGS. 6-9 and a thinner edge portion or flange 43a and 43a for placement in a respective circumferential channel or groove 45a and 45b, to anchor the septa in place in the main port body 56. The main port body 56 is formed from a biocompatible material, such as titanium alloy or other biocompatible corrosion-resistant metal, or from a biocompatible plastic. A titanium liner may be used along a floor or bottom surface 62 of the port chamber 54 when plastic is utilized for the port body 56.

In one version of an implantable vascular access port, the port body 56 and port chamber 54 are wider on the side containing the straight-line-access septum 60 in order to accommodate it and facilitate needle placement from various angles of approach, in contradistinction to an opposite side of port body 56 containing a hollow outlet tube 64, which may be more narrow or tapered. A sufficiently wide straight-line-access port aperture may also be formed in a standard frusto-conical port body without the need for widening the side of the port containing the straight-line-access aperture.

The straight-line- or lateral sidewall-access aperture 160 may be of various shapes and sizes assuming a round, oval, or rectangular configuration for example; if the port body and chamber assumes a frusto-conical configuration the straight-line-access aperture is slanted or curved. A wider straight-line-access aperture may allow for easier needle placement from different needle skin puncture locations and angles of approach. In another version the straight-line-access aperture 160 may be narrower and therefore less dependent on port body shape, allowing for precise alignment of the straight-line-access septum 60 with a port chamber outlet aperture 66. A narrower straight-line-access aperture 160 may be more difficult to target or enter but can be precisely aligned with the exiting port chamber outlet aperture 66, facilitating placement of a straight-line-access needle 72 and subsequently a slidable wire 74 through it, into the outlet aperture 66 and an attached catheter 70.

In one version the port body is relatively radiopaque while the respective silicone covered top access and lateral sidewall apertures are radiolucent. The edges of the at least partially radiopaque port body 56 surrounding a more narrow precisely aligned radiolucent straight-line- or lateral sidewall-access aperture 160 may be made even more radiopaque than the port body in order to better guide placement of the access needle through the straight-line-access septum 60 under direct fluoroscopic guidance; this modification may be of value regardless of aperture size. The disadvantage of accessing a small straight-line-access aperture 160 may therefore be overcome with the use of accentuated radiopaque port body markers along it edges, thereby enabling fluoroscopic needle placement while at the same time exploiting the advantage of more precise alignment of the straight-line-access aperture 160 with the port chamber outlet aperture 66. Outlet aperture 66 is configured to be radiolucent similarly to the respective access apertures to facilitate fluoroscopic cannulation with a needle or wire; similarly the outlet aperture 66 may have accentuated, at least partially radiopaque, rims or edges for needle guidance. In another version the port body is radiolucent with radiopaque edges or rims along the similarly radiolucent top and lateral sidewall access apertures along with the outlet aperture, thereby similarly guiding needle placement under fluoroscopy into or through any of the aforementioned apertures. The port chamber outlet aperture 66 may be surrounded by an inner surface of the internal chamber 54 having a straight conical or funnel-like shape and defining an outwardly tapering chamber extension (as opposed to a curved funnel) to help facilitate the placement of a slidable wire 74 through a straight access needle 72 placed through the straight-line-access septum 60, to facilitate entrance of the wire 74 into the hollow outlet tube 64 and subsequently the proximal catheter 70 (FIGS. 8-11). Alternatively the needle may directly engage a channel in the port body 56 adjacent to the outlet aperture 66 or the outlet stem 64 prior to wire advancement.

Figure 7:
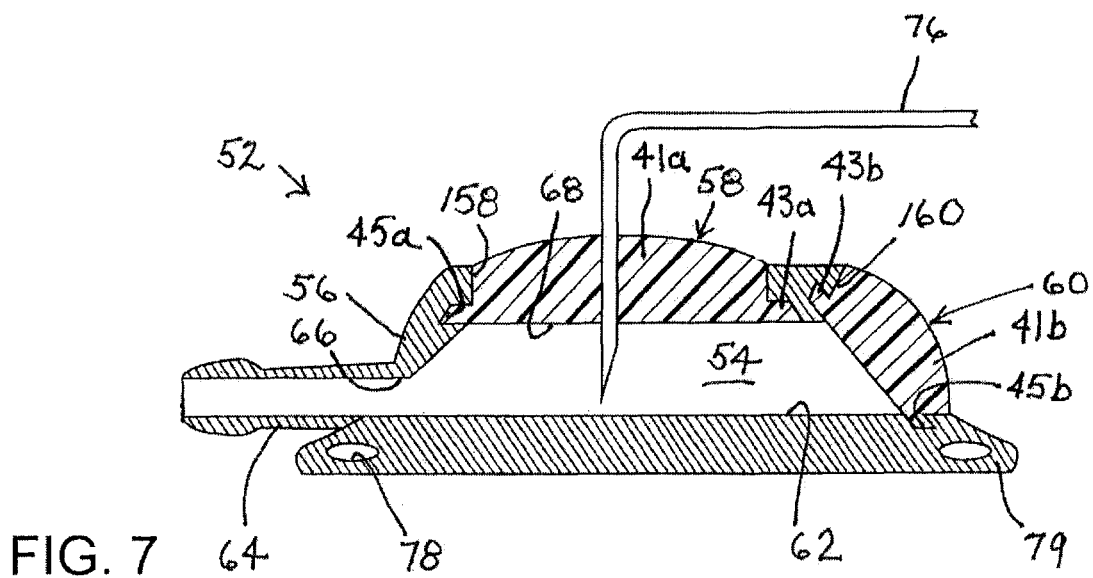
FIG. 7 is a midline sagittal cross-section view of the access port apparatus of FIG. 5, with a standard curved Huber needle inserted through a perpendicular-access port septum and associated aperture.
Figure 8:
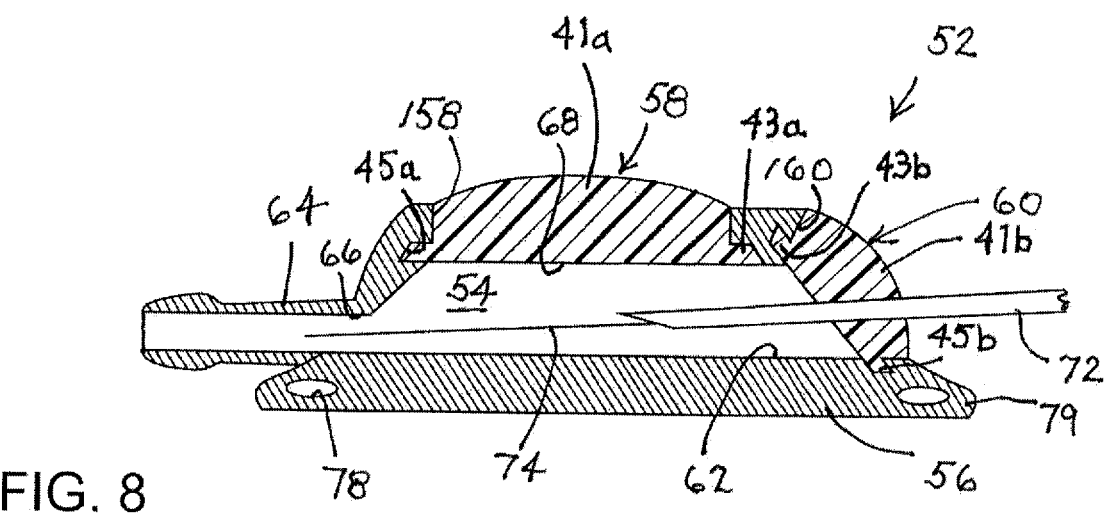
FIG. 8 is a midline sagittal cross-section view of the access port apparatus of FIG. 5, with a straight Huber needle or Seldinger needle inserted through a straight-line-access septum and associated aperture, also showing a guide wire being slidably inserted through the needle toward the opening of a tubular catheter attachment site, which protrudes from the port body.
Figure 9:
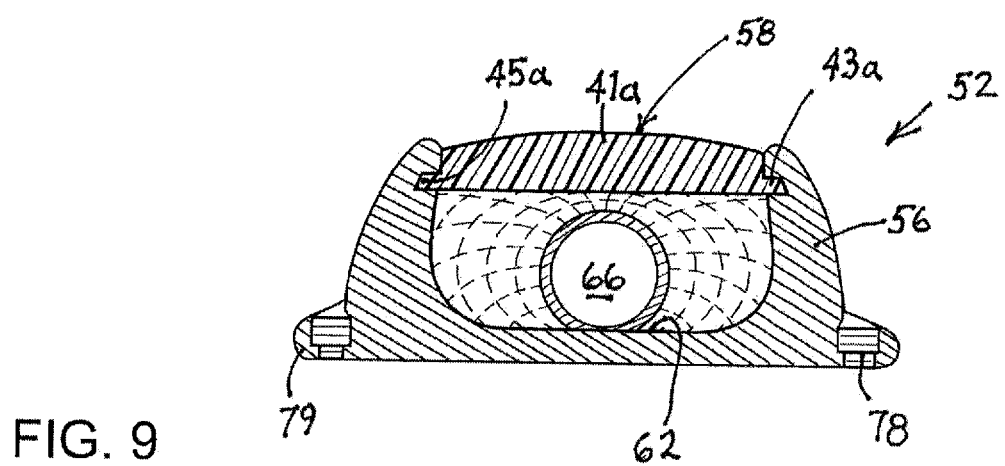
FIG. 9 is a coronal cross-sectional view of the access apparatus in FIG. 5, taken along the line IX-IX therein, along a vertical plane, which is orthogonal to that of FIG. 6, and showing the directed conical shape of the port chamber toward the opening of the tubular catheter attachment site.
Figure 10:
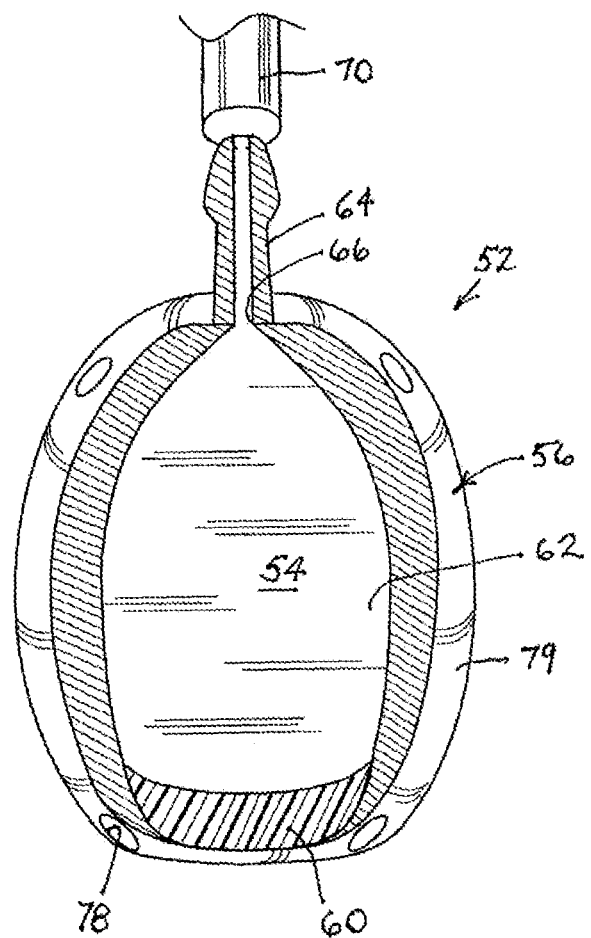
FIG. 10 is a horizontal cross-sectional view of the access apparatus in FIG. 6, taken along the line X-X therein, along a horizontal plane, which is orthogonal to that of FIG. 6.
Figure 11:
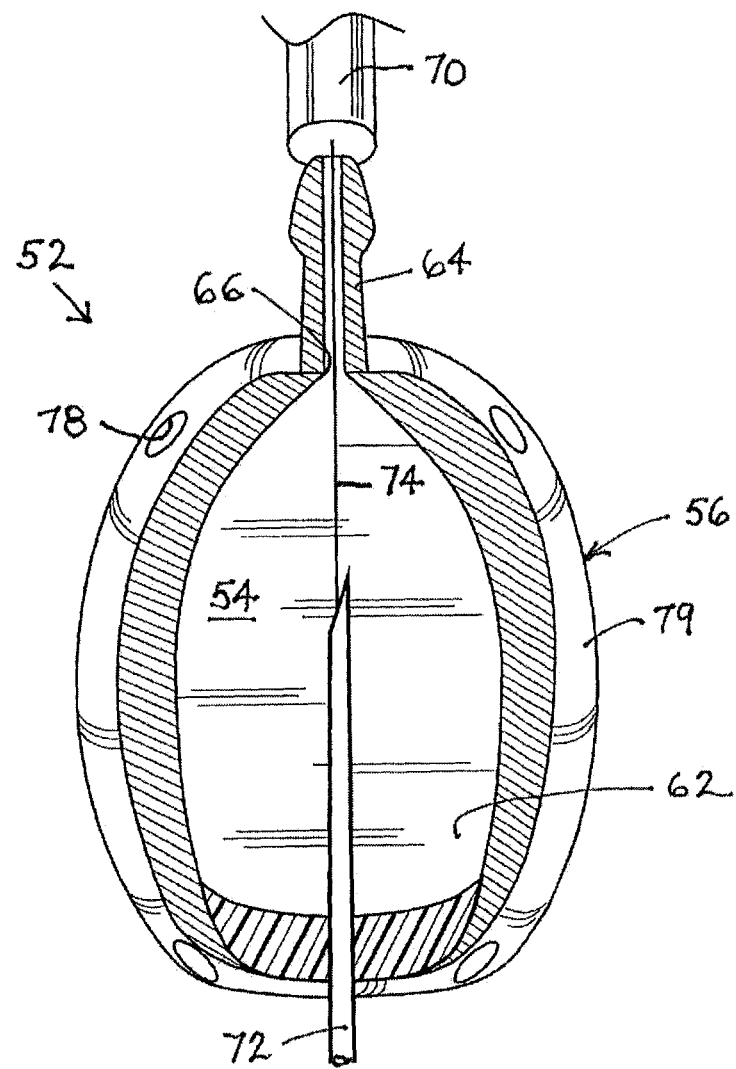
FIG. 11 is a horizontal cross-sectional view similar to that of FIG. 10, also showing a straight Huber needle or Seldinger needle inserted through a horizontal port septum or aperture with a guide wire being slidably inserted through the needle into an outlet stem or tube and attached single lumen catheter.

The straight conical outlet aperture or outwardly tapering chamber extension 66 shown in FIGS. 6-9 is located flush with the floor or bottom surface 62 of the internal chamber 54 of port body 56. Alternatively the straight conical chamber outlet aperture 66 may be centered at a midpoint between a top or upper surface 68 and the floor or bottom surface 62 of the port chamber 54 or anywhere in between, its precise location being preferably aligned with the location of the straight-line- or lateral sidewall-access aperture 160. The perpendicular-access aperture 158 for routine clinical use is shown in FIG. 7 with a curved Huber access needle in place for injecting medicines, into the internal port chamber 54, the medicines then passing through the port chamber outlet aperture 66, the hollow outlet tube 64, and finally the proximal catheter 70. The main port body 56 may have one or more round or oval eyelets 78 formed along its margins, particularly along a peripheral or circumferentially extending foot 79, to allow suturing of the port apparatus 52 to the underlying soft tissues within a surgically created subcutaneous pocket. These eyelets 78 may or may not be filled with silicone elastomeric material.

Figure 12:
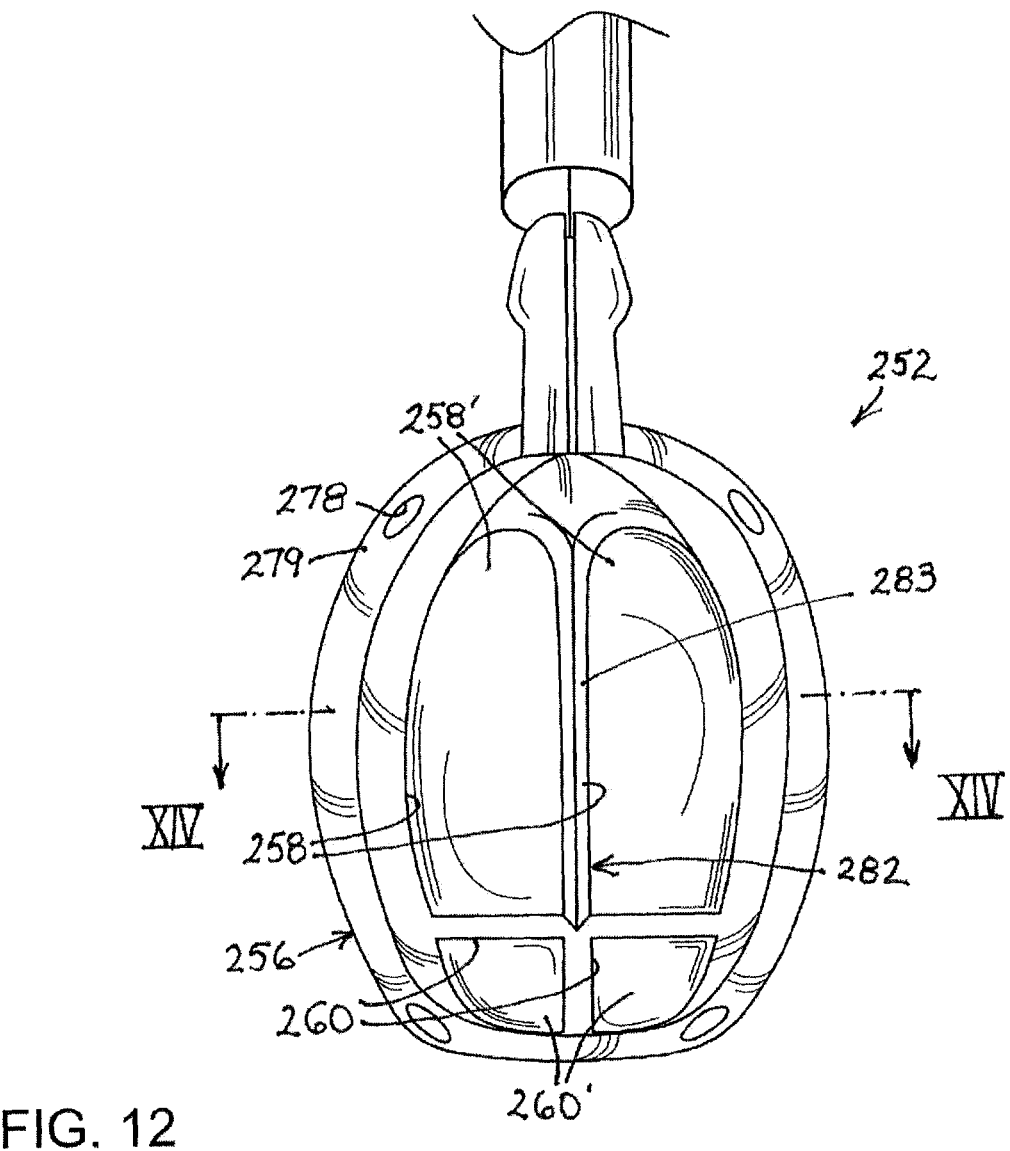
FIG. 12 is a top view of a double lumen access port apparatus according to a selected illustrative embodiment of the present invention with two perpendicular-access septa and two straight-line-access septa or apertures with an overall oval or elliptic frusto-conical shape to the port body.
Figure 13:
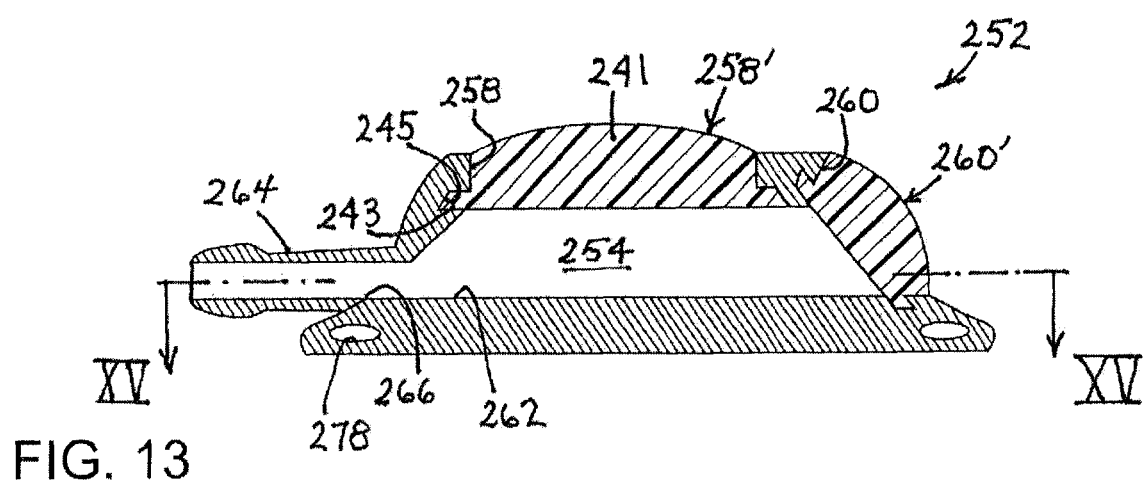
FIG. 13 is a sagittal cross-section view of the access port apparatus of FIG. 12, taken along line XIII-XIII in FIG. 15.
Figure 14:
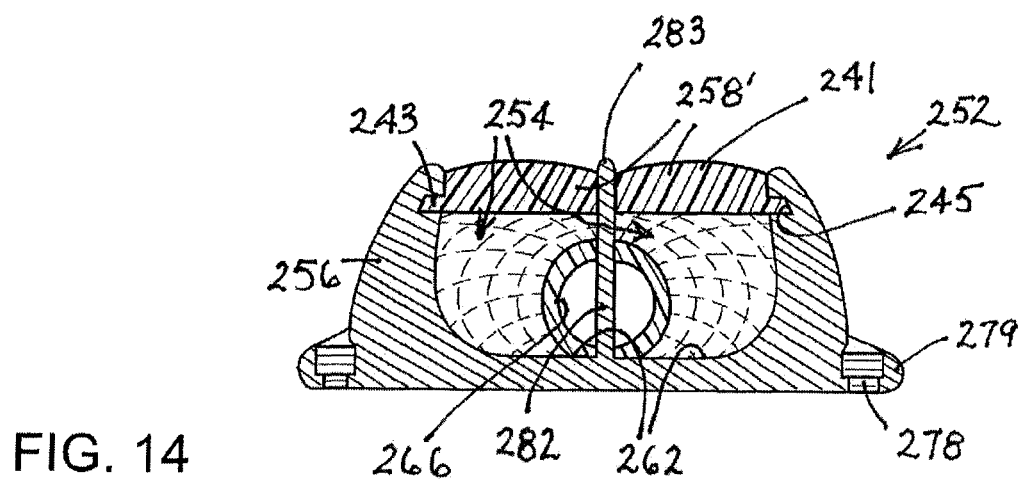
FIG. 14 is a coronal cross-sectional view of the access apparatus of FIGS. 12 and 13, taken along the line XIV-XIV in FIG. 12, along a vertical plane, which is orthogonal to the drawing plane of FIG. 13, and showing a directed conical shape of the port chamber toward the two semicircular openings of the double lumen tubular catheter attachment site.

In a double lumen implantable vascular access port 252 (FIGS. 12-16) two internal port chambers 254 are separated by a midline divider or partition 282 and exhibit respective perpendicular- or top-access apertures 258 and respective straight-line-access or lateral sidewall apertures 260. The port 252 includes a main port body 256 that is elliptic frusto-conical in configuration in one version and has four penetrable septa, namely two perpendicular-access septa 258' over respective apertures 258, similar to conventional double ports, as well as two straight-line-access or lateral sidewall septa 260' over respective apertures 260, primarily for the performance of various interventions to facilitate port placement, port repositioning, maintenance of secondary port patency, port removal, and port exchange. The septa (258' and 260') are formed from a resiliently deformable material such as silicone elastomer. The construction of the respective perpendicular- and straight-line-access septa (258' and 260') may include a thickened central portion 241 as shown in FIGS. 13 and 14 and a thinner edge portion 243 for placement in a circumferential channel or groove 245, to anchor the septa in place in the main port body 256. The main port body 256 is formed from a biocompatible material, such as titanium alloy or other biocompatible corrosion-resistant metal, or from a biocompatible plastic. A titanium liner (not separately depicted) may be used along floors or bottom surfaces 262 of the port chambers 254 when plastic is utilized for the port body 256.

The straight-line-access apertures 260 may be of various shapes and sizes assuming a round, oval, or rectangular configuration for example; if the port body 256 and chambers 254 assume an elliptic frusto-conical configuration, external and internal body surfaces not separately labeled have a surface curvature along multiple dimensions. Where straight-line-access apertures 260 and associated septa 260' are provided with a larger width (parallel to the floor or bottom surfaces 262), easier needle placement from different angles of approach is possible. In another version of the double lumen implantable vascular access port 252, the straight-line-access apertures 260 may be narrower and therefore relatively independent of port body shape, allowing for more precise alignment of the straight-line-access apertures 260 with respective port chamber outlet apertures 266. Narrower parallel-access apertures 260 are more difficult to target or enter but may be precisely aligned in the horizontal and or vertical planes with the exiting port chamber semicircular outlet apertures 266, facilitating placement of straight-line-access needles 272 and subsequently slidable wires 274 into the semicircular outlet apertures 266, and into the respective sides of an attached double lumen catheter 284, having a midline divider or partition 253. Alternatively the needles 272 may directly engage the outlet apertures 266 prior to wire advancement. A special needle design consisting of a semicircular or D shaped cannula and a semicircular yet pointed stylet may be required in order to directly engage the semicircular outlet aperture 266. A traditional rounded cannula with pointed stylet (Seldinger needle) may likely be adequate to direct a wire into the outlet aperture (s) without directly seating the needle into the semicircular outlet aperture. High flow applications such as apheresis and dialysis require direct needle engagement, coupled with a reversible locking mechanism (no back flow), into the respective halves of the semicircular outlet tubes, necessitating the use of corresponding semicircular cannula and semicircular pointed inner stylet.

The edges (not separately designated) of the radiopaque port body 256 surrounding more narrow precisely aligned straight-line radiolucent access apertures 260 may be made more radiopaque than the port body 256 in order to better enable placement of the access needles 272 through the straight-line-access septa 260' under direct fluoroscopic guidance, this modification being of value regardless of aperture size. The disadvantage of accessing a small straight-line-access aperture 260 may therefore be overcome with the use of accentuated radiopaque port body markers along the otherwise radiolucent aperture edges, thereby enabling fluoroscopic needle placement while at the same time exploiting the advantage of precise alignment of the straight-line-access apertures 260 with the port chamber outlet apertures 266. The radiopaque midline divider or partition 282 of the double lumen port apparatus 252 helps guide access needles 272 during placement through the two respective straight-line-access apertures 260 by fluoroscopy as well as by a palpable subcutaneous ridge 283 formed by the upper edge of the midline divider/partition 282 (FIGS. 12, 15, and 16).

Figure 15:
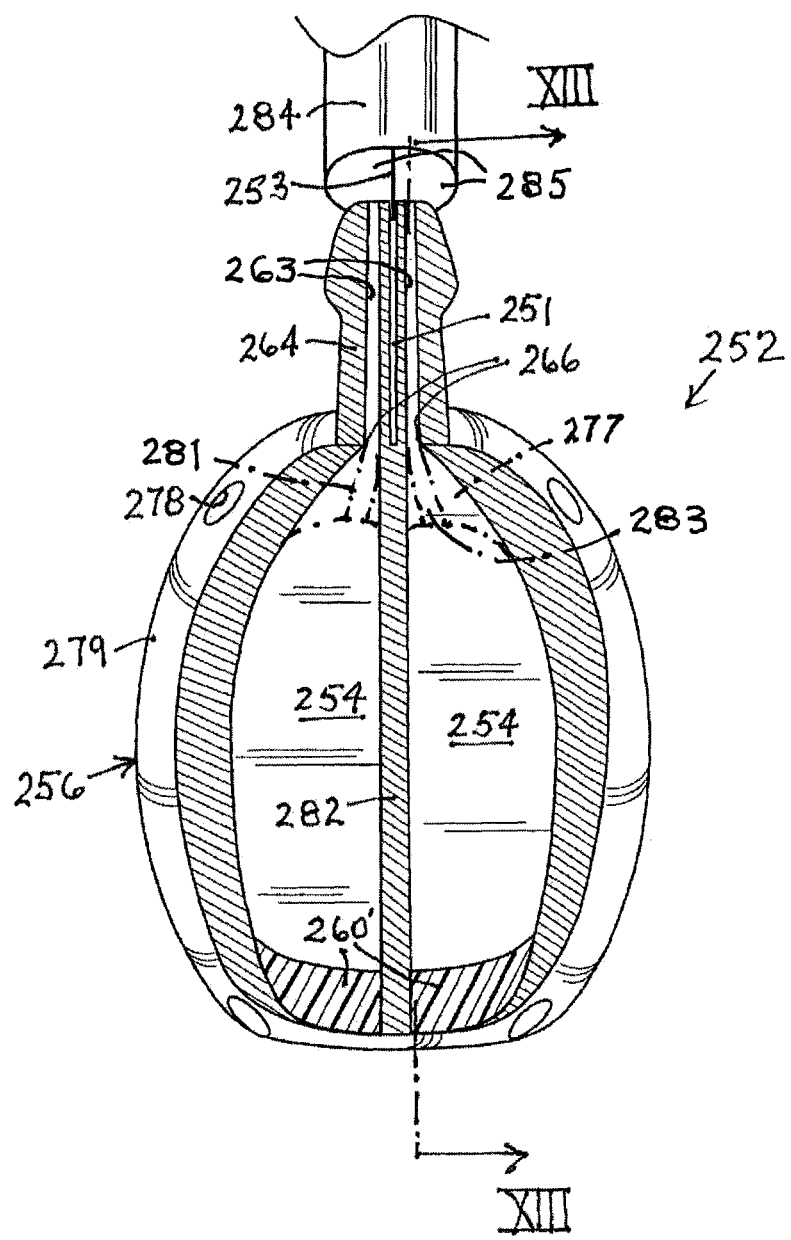
FIG. 15 is a horizontal cross-sectional view of the access apparatus of FIGS. 12-14, taken along the line XV-XV in FIG. 13, along a horizontal plane, which is orthogonal to the drawing plane of FIG. 13, also showing an attached double lumen catheter.
Figure 16:
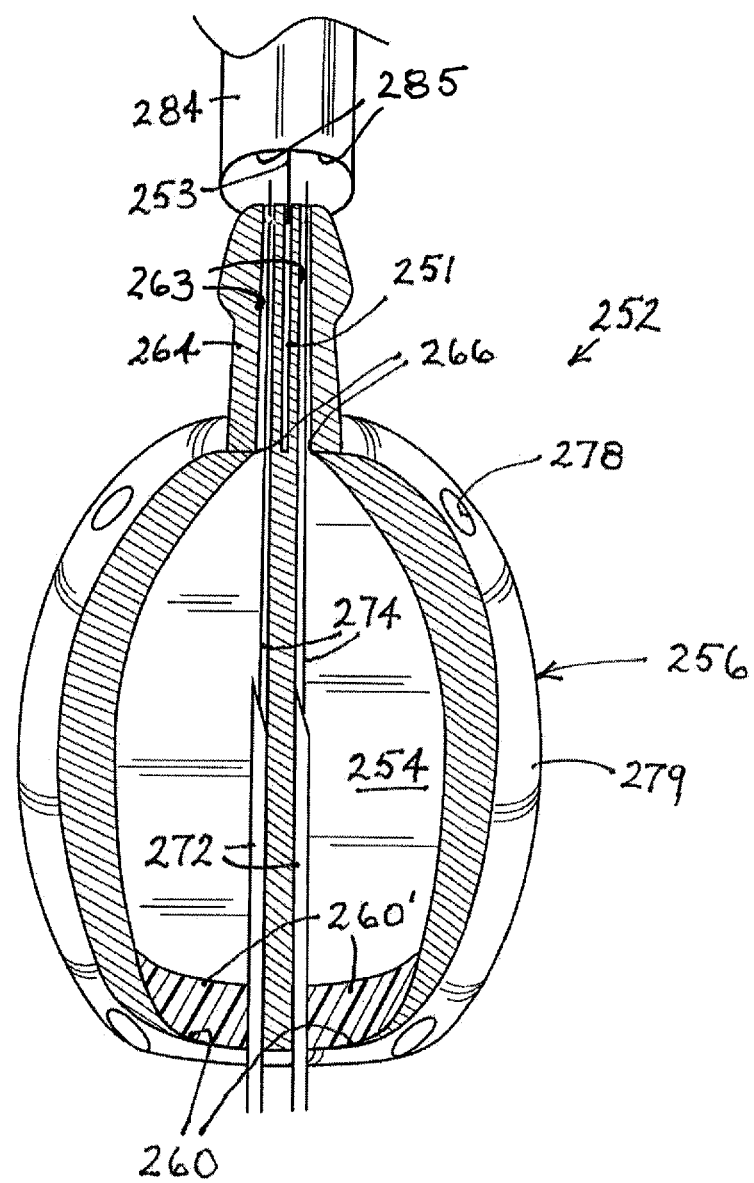
FIG. 16 is a horizontal cross-sectional view similar to that of FIG. 15, also showing two straight Huber needles or Seldinger needles inserted through two separate straight-line-access port septa or apertures with guide wires being slidably inserted through the respective needles into the two halves of a double lumen catheter.

Insertions or deployments of the straight-line-access needles 272 adjacent to respective sides of the midline divider 282 simultaneously align the straight-line-access needles with the respective semicircular outlet apertures 266 (FIGS. 15 and 16). A special needle design (not shown) consisting of a semi-cylindrical cannula and semi-cylindrical pointed stylet may be used to directly engage the semicircular outlet aperture, to enable temporary locking of the cannula to the port body and outlet tube particularly for high-flow procedures. High-flow applications such as apheresis and dialysis require direct needle engagement, coupled with a reversible locking mechanism (no back flow), into the respective halves of the semicircular outlet tubes, necessitating the use of corresponding semicircular cannula and semicircular pointed inner stylet.

Figure 44:
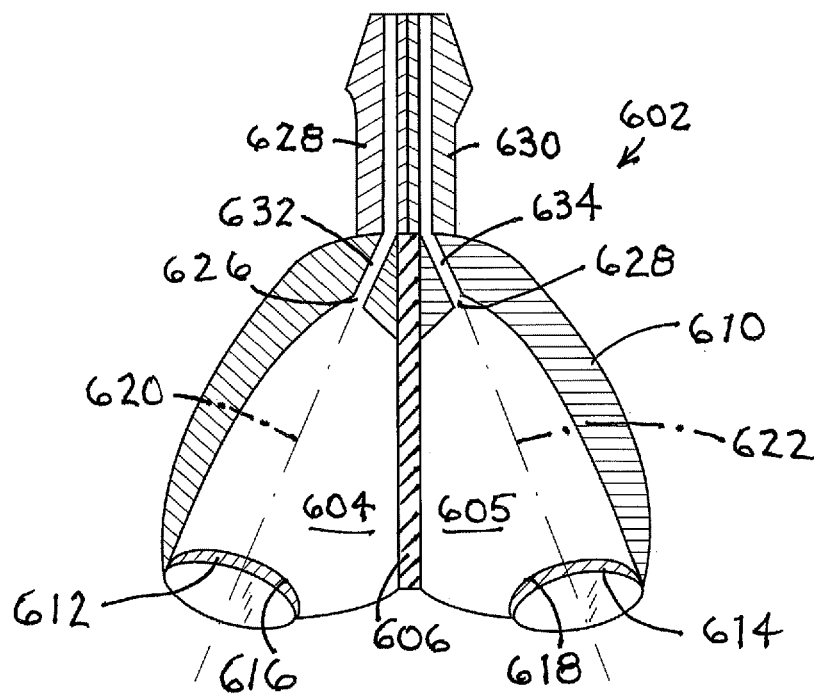
FIG. 44 is a schematic horizontal cross-sectional view of another implantable dual-chamber vascular access port in accordance with the present invention.

Alternatively, to enable use of conventional cylindrical needle assemblies with a double lumen vascular access port in accordance with the present invention, the vascular access port may be provided with (1) dual outlet tubes having cylindrical lumens, as discussed hereinafter with reference to FIG. 47, (2) a dual-flow outlet tube with a proximal end portion having two cylindrical lumens and a distal end portion having semi-cylindrical lumens, as described below with reference to FIG. 48, and (3) a thickened port body wall 277 (FIG. 15) having two cylindrical lumens 281 and 283 communicating with semi-cylindrical lumens 263 in outlet tube 264. Cylindrical lumens 281 and 283 are provided with annular snap-lock beads, as discussed herein, for releasably retaining stylet-needle cannulas particularly for high-flow procedures. Cylindrical lumens 281 and 283 may have proximal portions that extend parallel to partition 282 to facilitate the receiving of needle assemblies. Alternatively, straight-line or lateral access apertures 260 may be disposed at greater distances from partition 282, as shown in FIG. 44, to enable proper co-linear insertion of needles into lumens 281 and 283.

Port chamber outlet apertures 266 may be radiolucent in an otherwise at least partially radiopaque port body to facilitate needle or wire cannulation. Alternatively the outlet apertures 266 may be provided with radiopaque edges in an otherwise radiolucent port body in order to facilitate cannulation with a needle or wire. The port chamber outlet apertures 266 may be provided with respective straight conical or funnel-like guiding surfaces (defining outwardly tapering chamber extensions) on the respective downstream sides of internal chambers 254 (half or partial funnel in double lumen version on either side of the midline divider 282) to help facilitate the placement of slidable wires 274 through straight access needles (either cylindrical or semi-cylindrical) 272 placed through the straight-line-access septa 260', to facilitate entrance of the wires 274 or needles of semicircular cross-sections 272 into respective lumens 263 of a double lumen hollow outlet tube 264 and subsequently into respective halves 285 of a proximal double lumen catheter 284, compartmentalized by the midline catheter divider 253. (FIG. 16). The straight conical outlet apertures or outwardly tapering chamber extension 266 (half or partial funnel in double lumen version on either side of the midline divider/partition 282) shown in FIGS. 13 and 14 are located flush with the floors 262 of the port chambers 254. Alternatively the straight conical chamber outlet apertures 266 may be centered at a midpoint between top or upper surfaces 268 and the floor or bottom surfaces 262 of the port chambers 254 or anywhere in between, the precise locations being preferably aligned with the locations of the straight-line-access apertures 260. The respective perpendicular-access apertures 258 for routine clinical use are accessed with a curved Huber needle (shown in FIG. 7 for a single lumen port) for injecting medicines, which may then enter the port chambers 254, then the port chamber outlet apertures 266, subsequently entering the respective side of the double lumen hollow outlet tube 264, and finally the respective halves of the proximal double lumen catheter 284, separated by the midline divider/partition 253. The double lumen outlet tube 264 contains a midline groove 251, which accepts the midline divider 253 of the double lumen catheter 284 (FIGS. 12, 15, and 16). The main port body 256 may have one or more round or oval eyelets 278 formed at spaced locations in an outwardly and circumferentially extending foot 279 to allow suturing of the double lumen implantable vascular access port 252 to the underlying soft tissues within a surgically created subcutaneous pocket. These eyelets 278 may or may not be filled with silicone elastomeric material.

Figure 17:
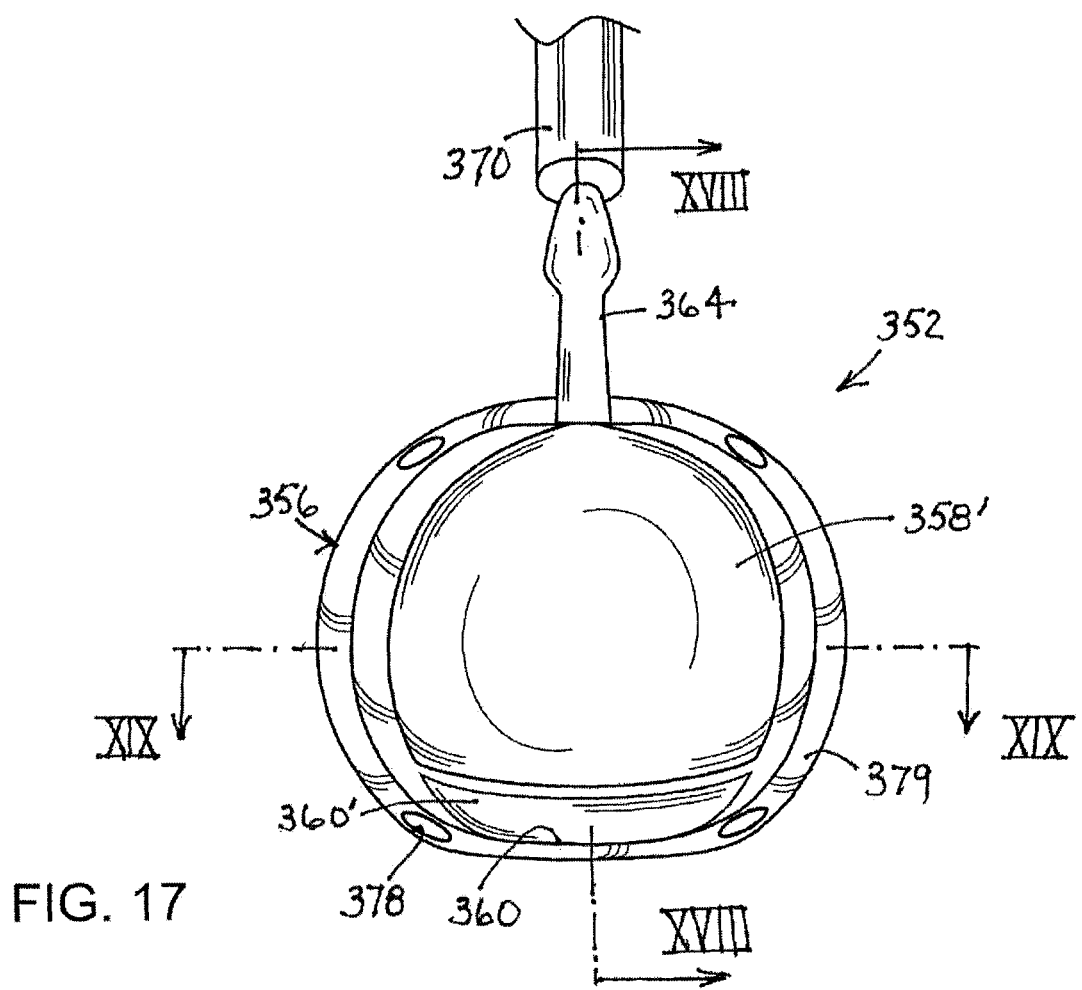
FIG. 17 is a top view of an access port apparatus according to a selected illustrative embodiment of the present invention with one perpendicular-access septum and one straight-line-access septum with an overall frusto-conical shape to the port body.
Figure 18:
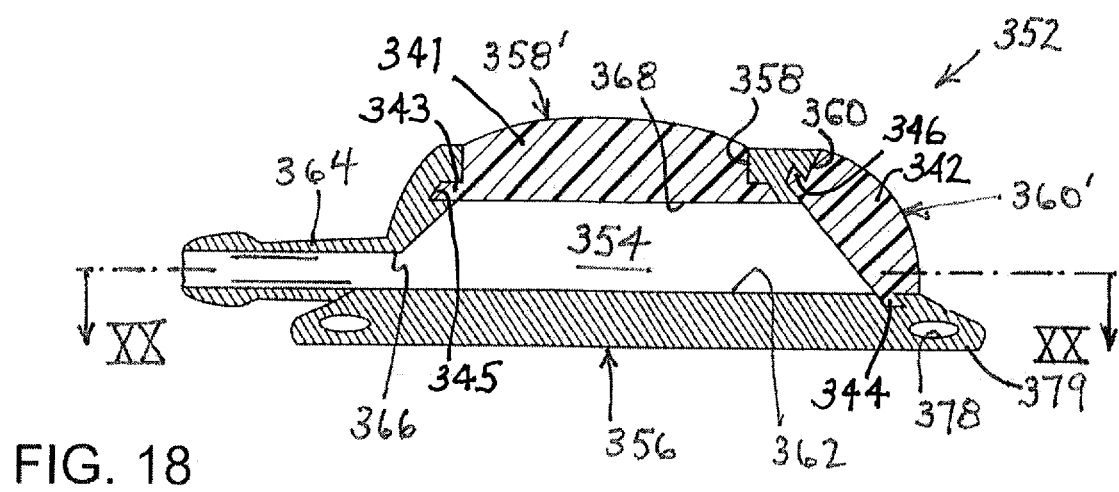
FIG. 18 is a midline sagittal cross-section view of the access port apparatus of FIG. 17, taken along the line XVIII-XVIII therein.
Figure 19:
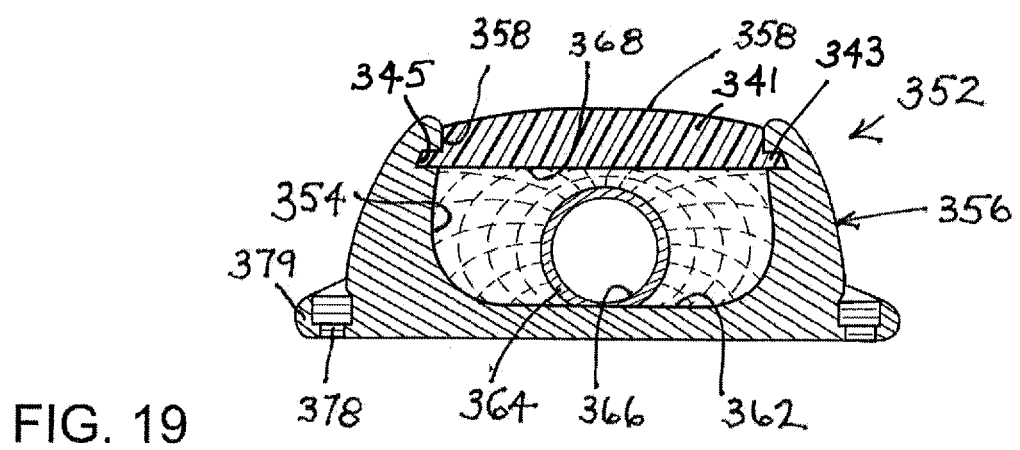
FIG. 19 is a coronal cross-sectional view of the access apparatus in FIG. 17, taken along the line XIX-XIX therein, along a vertical plane, which is orthogonal to that of FIG. 18, and showing the directed conical shape of the port chamber toward the opening of the tubular catheter attachment site.
Figure 20:
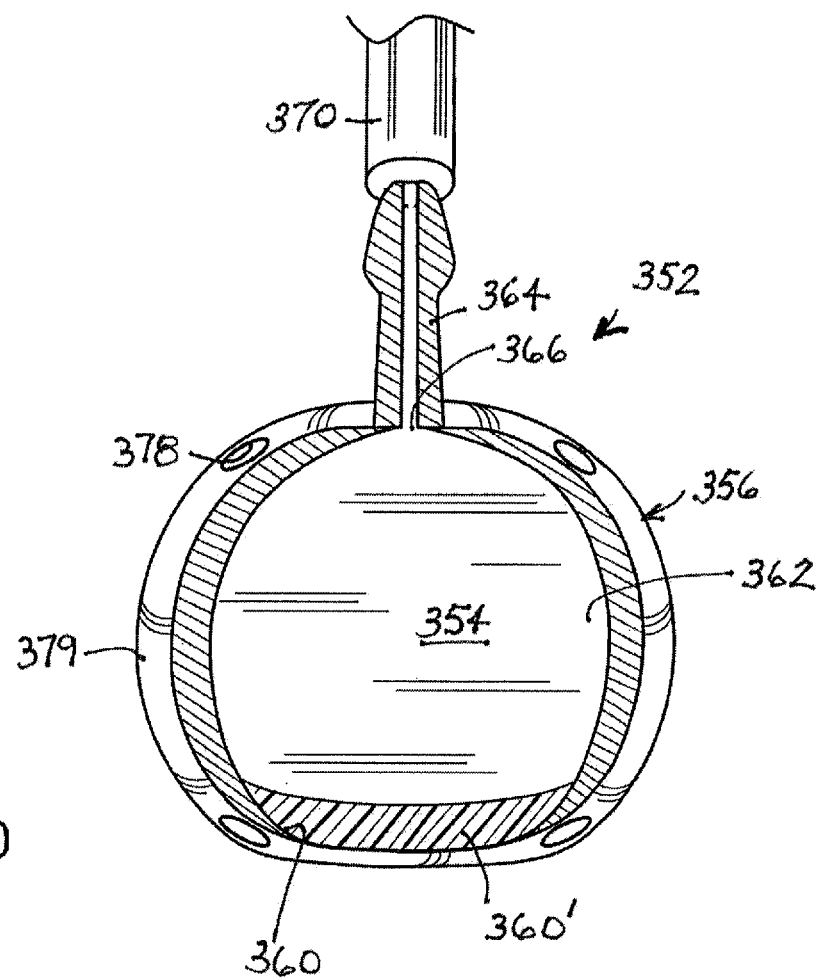
FIG. 20 a horizontal cross-sectional view of the access apparatus in FIG. 18, taken along the line XX-XX therein, along a horizontal plane, which is orthogonal to that of FIG. 18, also showing an attached single lumen catheter.
Figure 21:
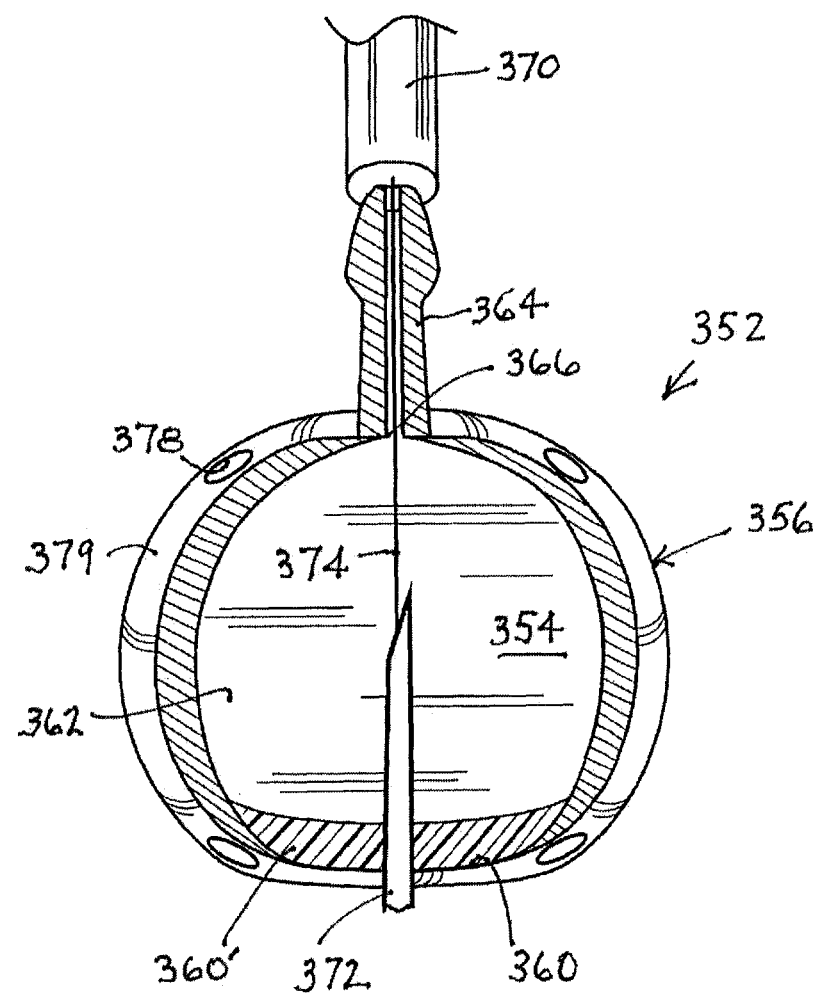
FIG. 21 is a horizontal cross-sectional view similar to that of FIG. 20, also showing a straight Huber needle or Seldinger needle inserted through a straight-line-access port septum or aperture with a guide wire being slidably inserted through the needle into a single lumen catheter.

Another single lumen implantable vascular access port apparatus 352, shown in FIGS. 17-21 includes a main port body 356 having a hollow chamber 354 formed therein. A main port body 356 has two penetrable apertures (358 and 360) including a perpendicular- or top-access aperture 358 and a straight-line- or lateral-access aperture 360 covered or bridged by respective septa 358' and 360'. Perpendicular-access aperture 358 allows conventional port access while novel straight-line-access aperture 360 enables or facilitates performance of various interventions to facilitate initial port placement, port catheter repositioning, maintenance of secondary port patency, port removal, and port exchange. In this implantable vascular access port apparatus 352, the main port body 356 is frusto-conical, the main port chamber 354 is cylindrical, frusto-conical or preferably ellipsoidal, an ellipsoidal or spheroidal port chamber design fosters circular motion and mixing of the injected fluids minimizing dead space within the chamber. Acute edges and corners result in sudden directional changes in fluid flow through the port chamber creating dead zones, cell shearing, platelet activation and clotting. A frusto-conical body 356 may surround a cylindrical, frusto-conical or preferably ellipsoidal port chamber 354 as shown in FIG. 17, however, the port body 356 may assume differing shapes including but not limited to a frusto-conical, elliptic frusto-conical, horseshoe shaped, teardrop shaped, torpedo shaped, or ovoid to reduce friction during port exchange, one of the envisioned methods or procedures made possible by the invention, yet retain the desirable non-turbulent flow characteristics of an ellipsoidal or spheroid (true sphere or oblate sphere) port chamber 354 (not shown). In another version the radiolucent lateral access aperture 360' is constructed of an inwardly tapering recess or palpable depression in the port body, allowing for access needle placement into the straight-line-access septum, which may no longer be located along the periphery of the port body 356, but more centrally abutting the port chamber (not shown). The port chamber 354 and port body 356 therefore may be of similar or differing shapes respectively. The septa (358' and 360') are formed from a resiliently deformable material such as silicone elastomer. The perpendicular- and straight-line-access septa 358' and 360' include thickened central portions 341 and 342 as shown in FIGS. 18 and 19 and thinner edge portions 343 and 344 for placement in circumferential channels or grooves 345 and 346 to anchor the septa 358' and 360' in place in the main port body 356. The main port body 356 is formed from a biocompatible material, such as titanium alloy or other biocompatible corrosion-resistant metal, or from a biocompatible plastic. A titanium liner (not shown) may be used along a floor or bottom 362 of the port chamber 354 when plastic is utilized for the port body 356. The straight-line-access aperture 360 may be of various shapes and sizes assuming a round, oval, or rectangular configuration for example; in a frusto-conical implantable vascular access apparatus 352 the straight-line-access septum 360' is in part curved FIGS. 17 and 20. A wider straight-line-access aperture may allow for easier needle placement from different skin puncture site locations and angles of approach. In another version the straight-line-access port aperture 360 may be narrower and therefore less dependent on port body shape, allowing for precise alignment of the straight-line-access port septum 360' with the port chamber outlet aperture 366. A narrower straight-line-access aperture 360 may be more difficult to target or enter but can be precisely aligned in the horizontal and or vertical planes with the exiting port chamber outlet aperture 366, facilitating placement of a straight-line-access needle 372 and subsequently a slidable wire 374 there through, into the outlet aperture 366, outlet stem 364, and an attached catheter 370 (FIG. 21). The edges of the radiopaque port body 356 surrounding a more narrow precisely aligned straight-line-access aperture 360 may be made even more radiopaque than the port body 354 in order to better enable placement of the access needle into and through the straight-line-access septum 360' under direct fluoroscopic guidance, this modification being beneficial regardless of aperture size. The disadvantage of accessing a small straight-line-access aperture 360 may therefore be overcome with the use of accentuated radiopaque port body markers along the edges of the aperture, thereby enabling fluoroscopic needle placement while at the same time exploiting the advantage of more precise alignment of the straight-line-access aperture 360 with the port chamber outlet aperture 366. The port chamber outlet aperture 366 may be located in a straight conical or funnel-like shape or outwardly tapering chamber extension (as opposed to a curved funnel) of the respective wall of the internal chamber 354 to help facilitate the placement of the slidable wire 374 through the straight access needle 372 as placed through the straight-line-access septum 360', to facilitate entrance of the needle 372 or wire 374 into the hollow outlet tube 364 and subsequently the proximal catheter 370 (FIGS. 19-21). Alternatively, the needle may directly engage a channel in the port body 356 adjacent to the outlet aperture 366 or the outlet stem prior to wire advancement. The straight conical outlet aperture (outwardly tapering chamber extension) 366 shown in FIGS. 19-21 is located flush with the floor or bottom surface 362 of the port chamber 354. Alternatively the straight conical chamber outlet aperture 366 may be centered at the midpoint between a top surface 368 and the floor surface 362 of the port chamber 354 or anywhere in between, its precise location preferably being aligned with the horizon-access aperture 360. The perpendicular-access aperture 358, for routine clinical use, is shown in FIG. 7 with a curved Huber access needle in place for injecting medicines, which may then enter the port chamber 354, then the port chamber outlet aperture 366, subsequently the hollow outlet tube 364, and finally the proximal catheter 370. The main port body 356 may have one or more round or oval eyelets 378 formed along its margins, particularly, along an outwardly and circumferentially extending foot 379, to allow suturing of the port or vascular access apparatus 352 to the underlying soft tissues within a surgically created subcutaneous pocket. These eyelets 378 may or may not be filled with silicone elastomeric material.

Figure 2:
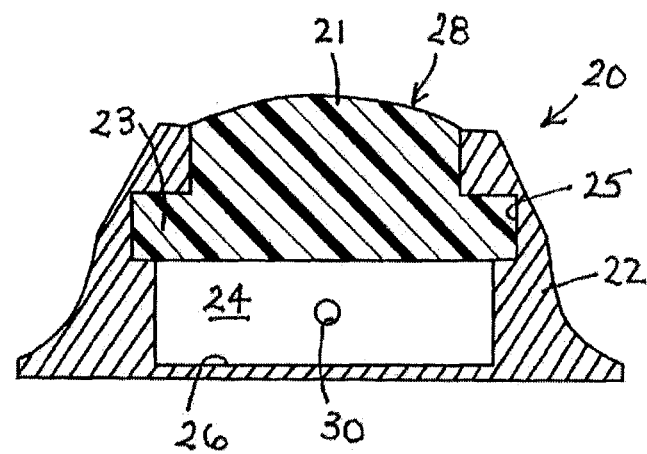
FIG. 2 is coronal cross-sectional view of the access port apparatus of the access port of FIG. 1, taken along the line II-II therein, along a vertical plane, orthogonal to the plane of FIG. 1.
Figure 3:
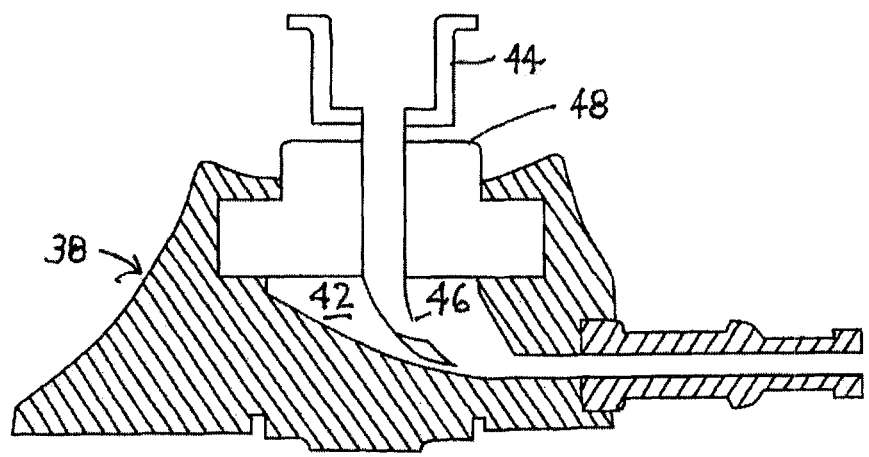
FIG. 3 is a sagittal cross-section view of a saucerized or conical access port chamber apparatus according to a prior art design containing a specialized curved pencil point access needle, which in turn contains a distal side hole along the apex of the curved needle.
Figure 4:
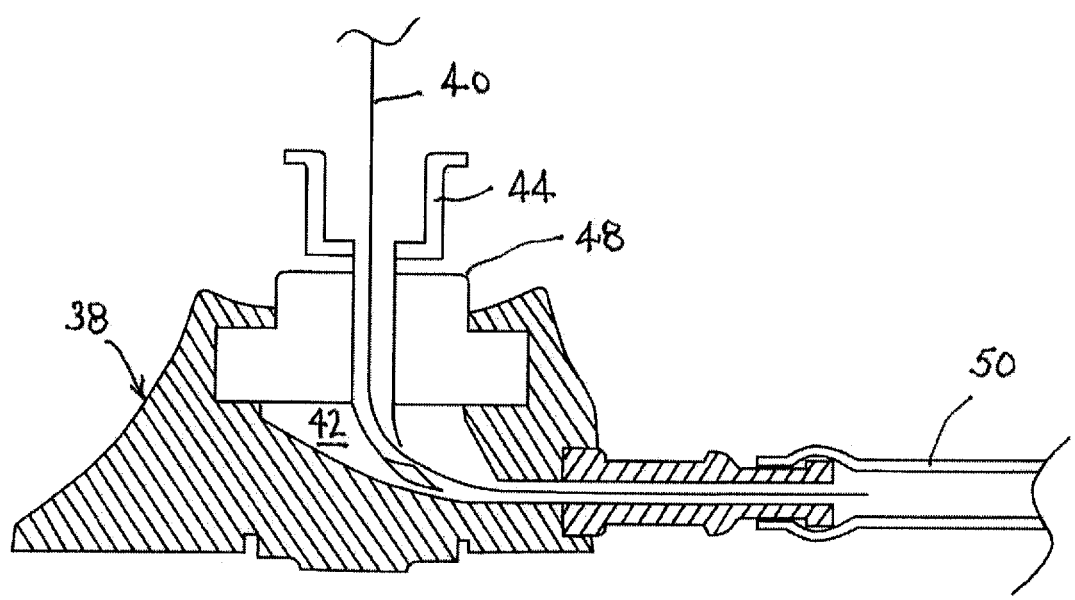
FIG. 4 is a sagittal cross-section view of a prior art design similar to that of FIG. 3, also showing a guide wire being slidably inserted through the needle apparatus and into a catheter.
Figure 5:
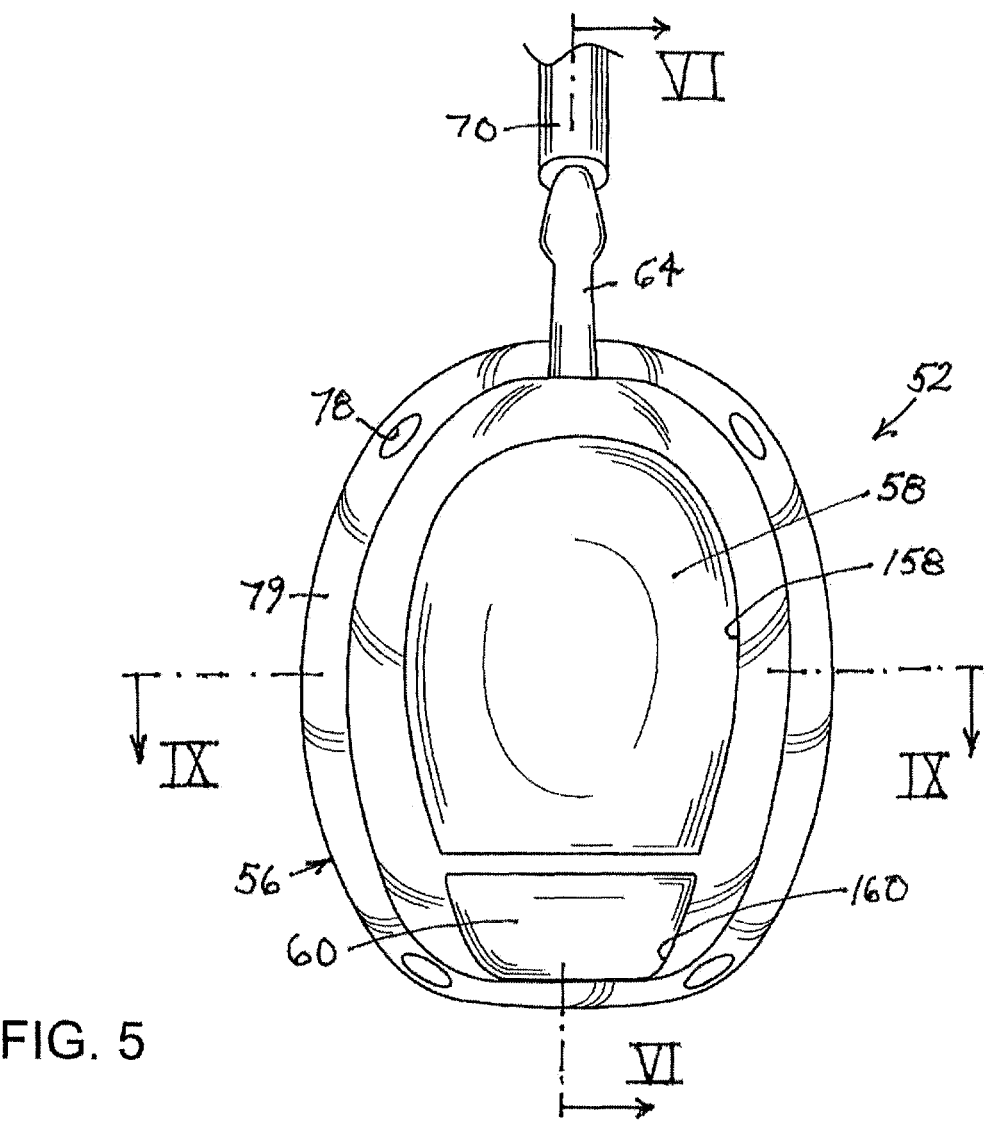
FIG. 5 is a top plan view of an access port apparatus according to a selected illustrative embodiment of the present invention with one perpendicular-access septum and one straight-line-access septum with an overall oval shape to the port body.
Figure 6:
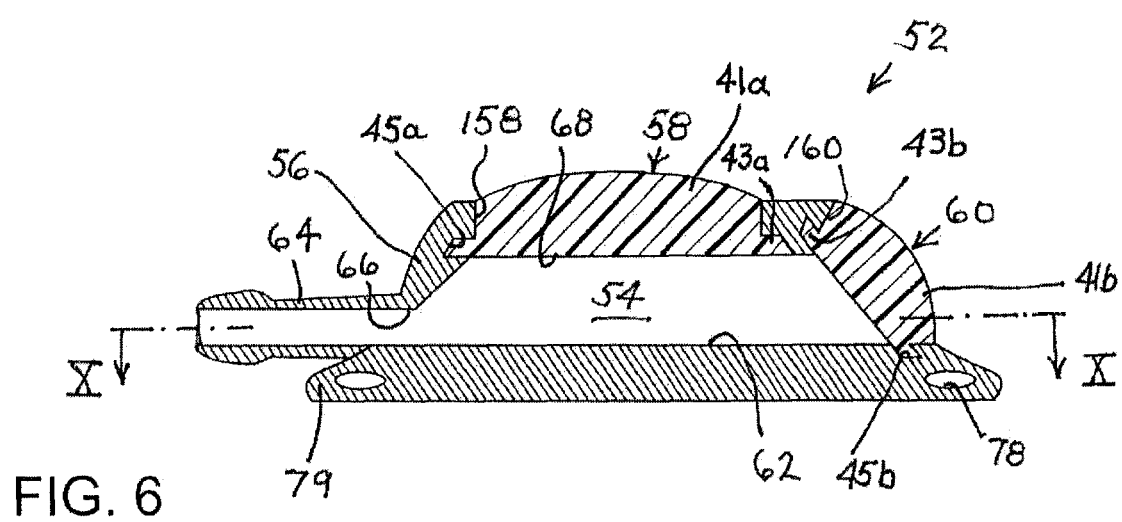
FIG. 6 is a midline sagittal cross-section view of the access port apparatus of FIG. 5, taken along the line VI-VI therein.
Figure 22:
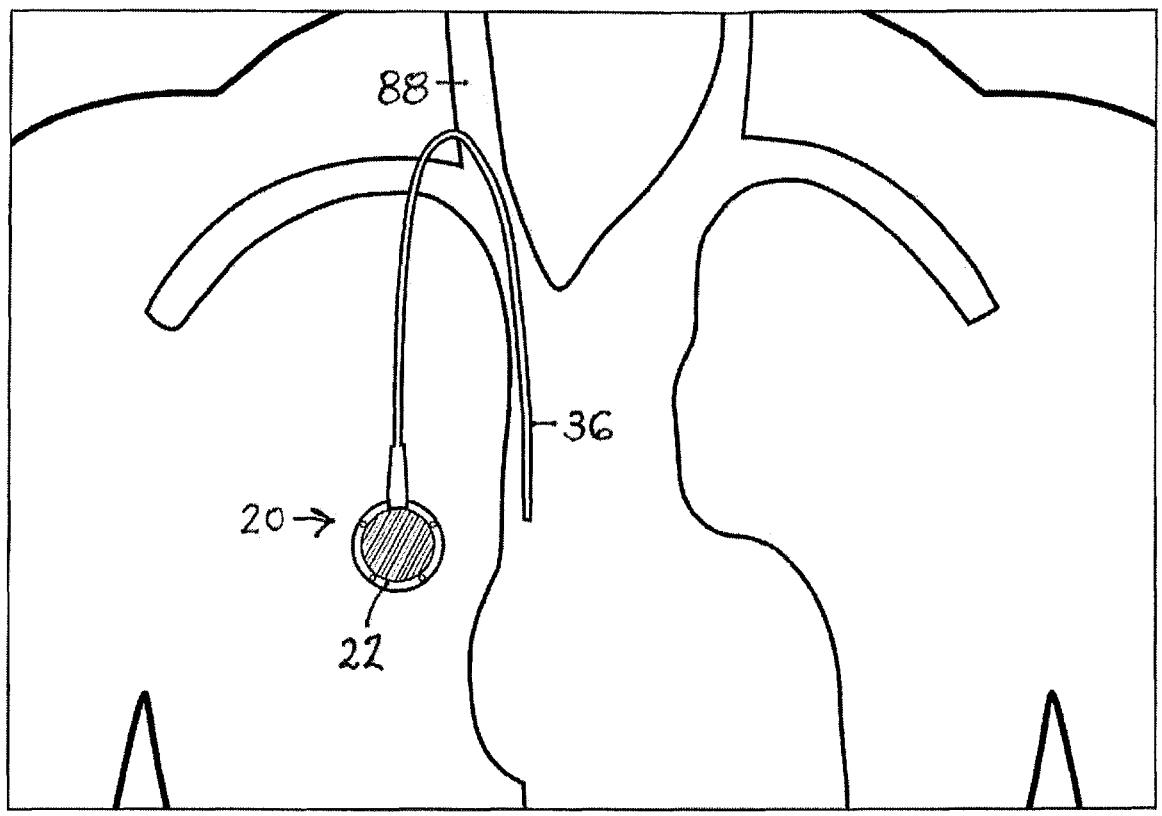
FIG. 22 is a diagram of a generic patient's central venous access system according to a prior art design.
Figure 23:
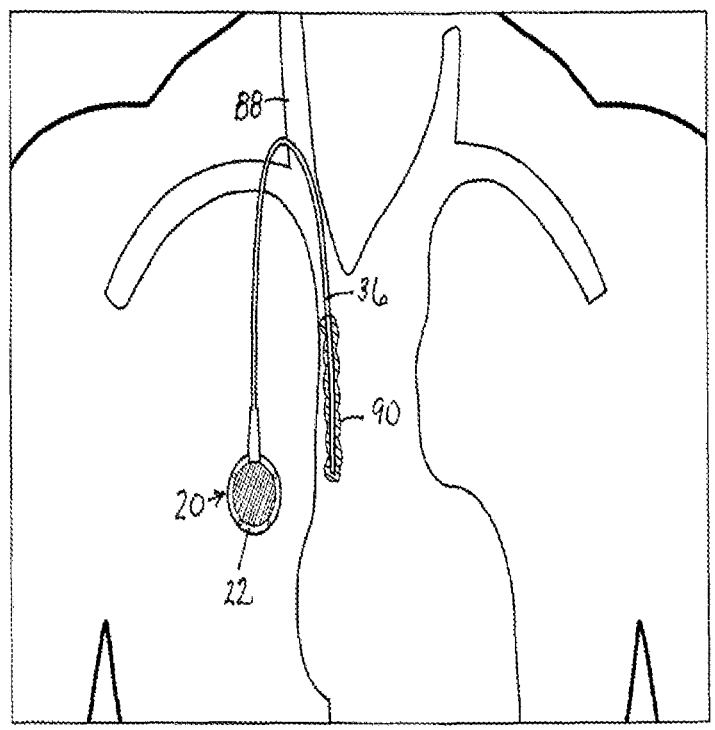
FIG. 23 is a diagram of a generic patient's central venous access system according to a prior art design with a biofilm or fibrin sheath coating the intravascular portion of the catheter tip.
Figure 24:
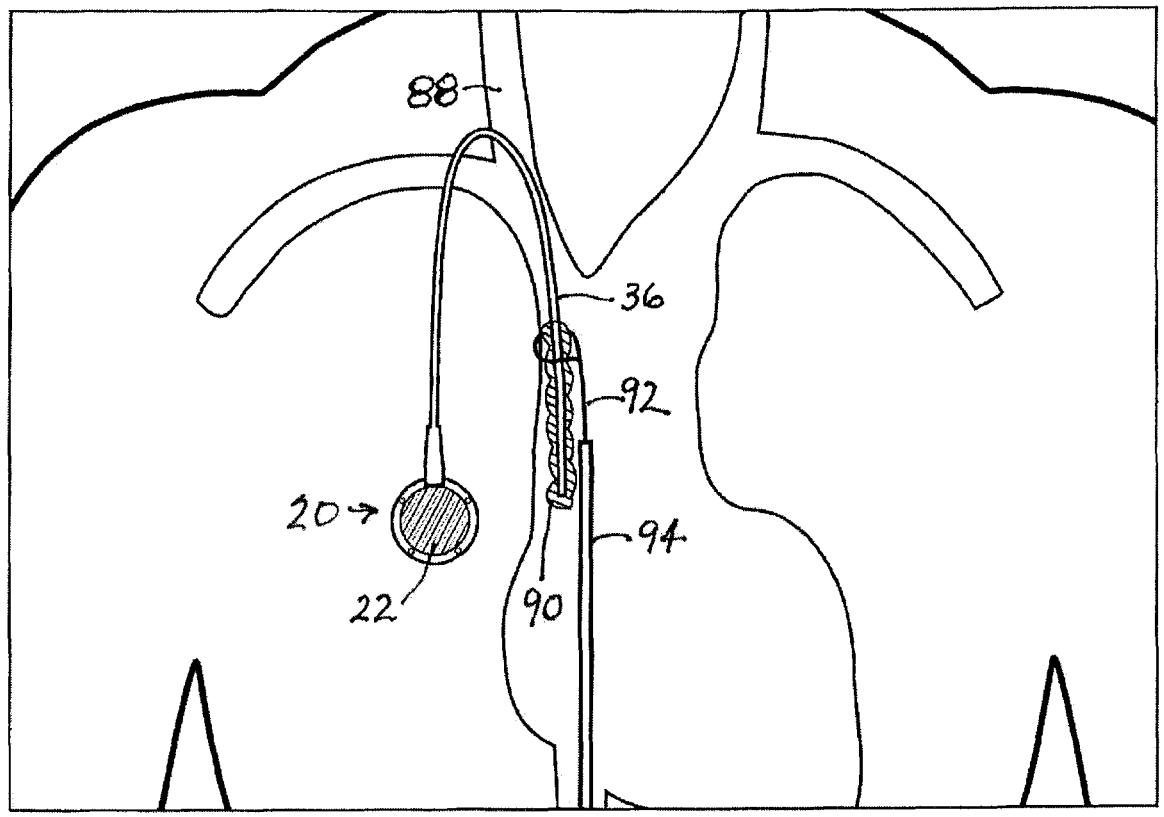
FIG. 24 is a diagram of a generic patient's central venous access system according to a prior art design, similar to FIG. 23, showing positioning of a loop snare over the catheter and fibrin sheath.
Figure 25:
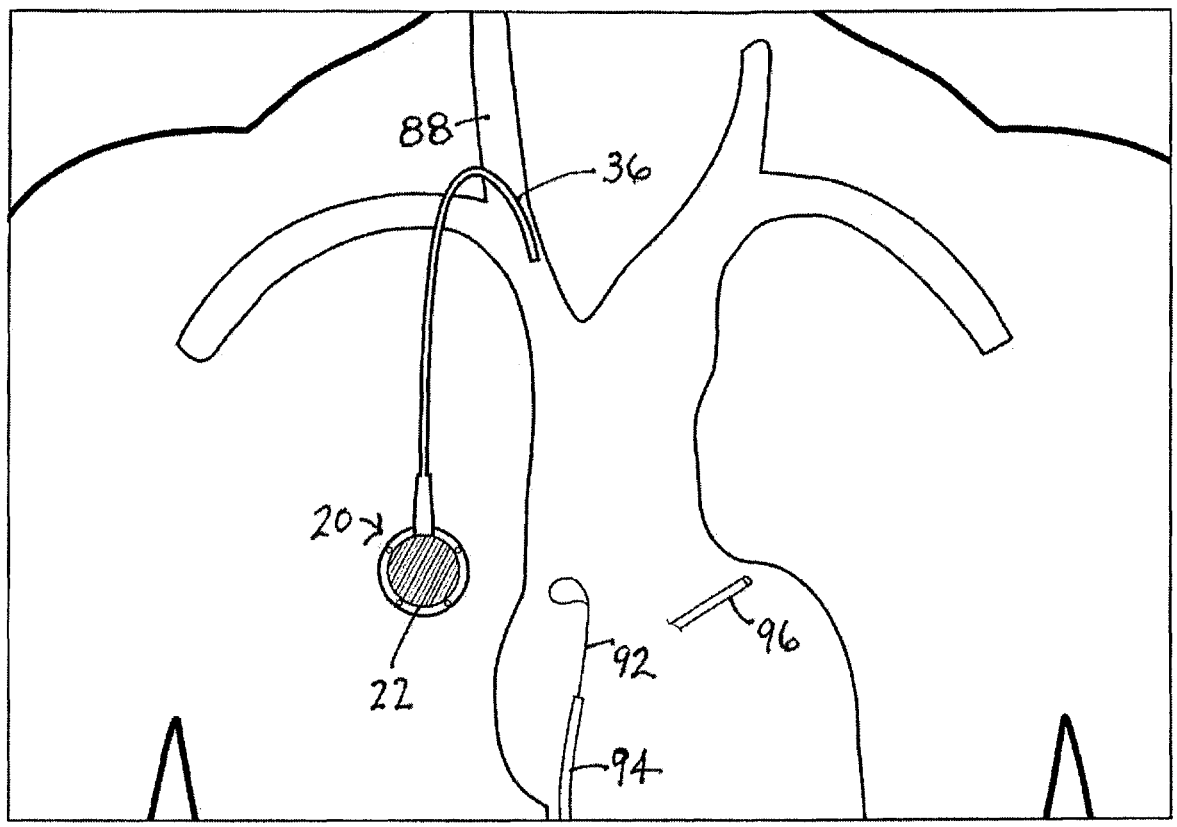
FIG. 25 is a diagram of a generic patient's central venous access system according to a prior art design, similar to FIG. 24, showing the procedure related complication of a free intravascular catheter fragment which may occur without the inventive device described herein.
Figure 26:
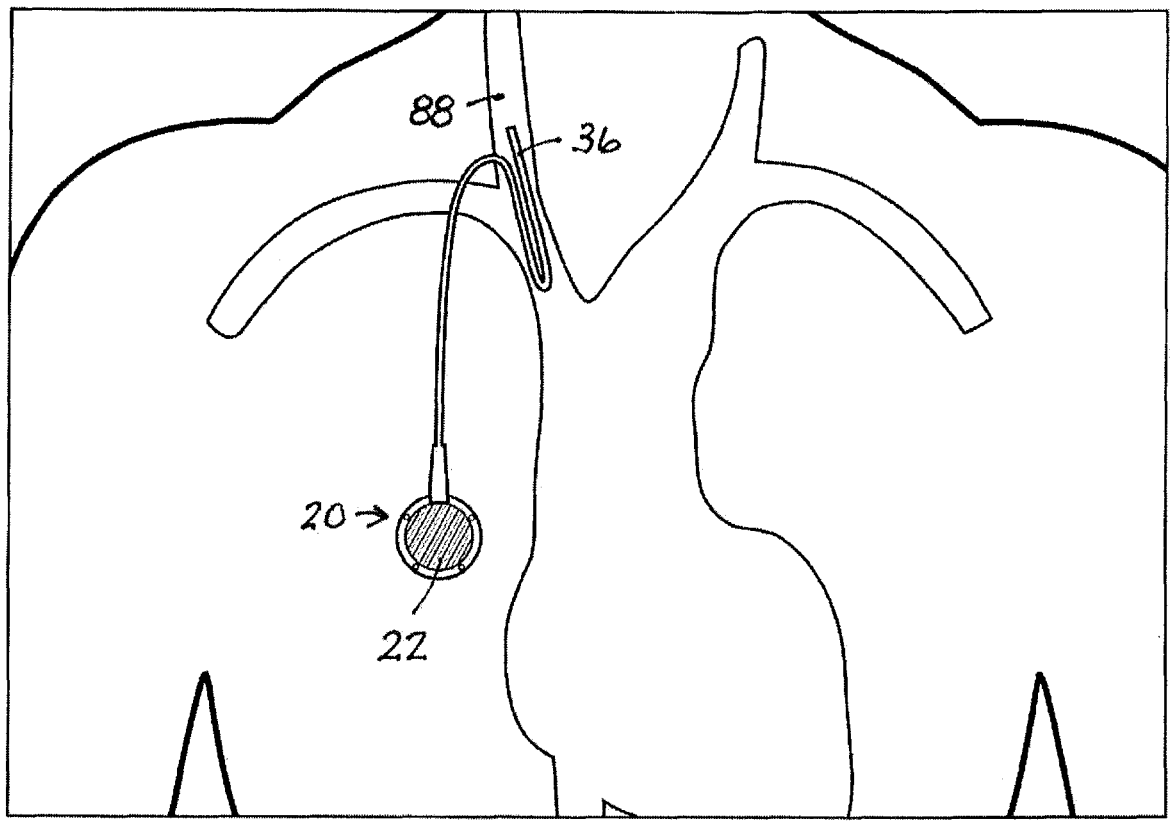
FIG. 26 is a diagram of a generic patient's central venous access system according to a prior art design, showing a flipped or malpositioned catheter.

A generic port apparatus 20 such as that illustrated in FIGS. 1 and 2 is shown in FIG. 22 surgically implanted into the subcutaneous soft tissues of the upper chest wall with the proximal catheter attached to the port body 22, the catheter 36 is shown entering right the internal jugular vein 88, with the distal tip of the catheter 36 positioned in the central venous system, either the superior vena cava (SVC) or the right atrium (RA). FIG. 23, similar to FIG. 22, shows a generic port apparatus 20, with a fibrin sheath 90 or biofilm surrounding the distal intravascular portion of the catheter 36, resulting in catheter malfunction, either complete catheter occlusion or at a minimum an inability to aspirate blood from the catheter, precluding ones ability to confirm appropriate needle position within the port chamber, and thus safe conditions for the instillation of fluids or medicine. FIG. 24, similar to FIG. 23, shows a generic port apparatus 20, with a fibrin sheath 90 or biofilm surrounding the distal intravascular portion of the catheter 36, resulting in catheter malfunction. An intravascular loop snare 92 exiting from a catheter 94 placed from a femoral vein puncture is shown surrounding the port catheter 36 and fibrin sheath 90, immediately prior to tightening the snare in preparation for striping off the fibrin sheath from the catheter, an established procedure in the medical field. FIG. 25, similar to FIG. 24, shows a generic port apparatus 20, after fibrin sheath stripping with a loop snare 92 demonstrating a known complication of such a procedure, which is catheter fragmentation with a resultant intravascular loose body 96. FIG. 26, similar to FIG. 22, shows a generic port apparatus 20, with a catheter 36 having a flipped or migrated aberrant catheter tip in the internal jugular vein, resulting in catheter dysfunction and an undesirable location to inject medicines, also predisposing to venous thrombosis, a known complication of central venous ports. This aberrant catheter position can be remedied by snaring the distal end of the catheter in a similar fashion to that of FIG. 24 for fibrin sheath formation, thereby repositioning the catheter tip in the superior vena cava or right atrium; alternatively the port may be surgically revised.

Figure 27:
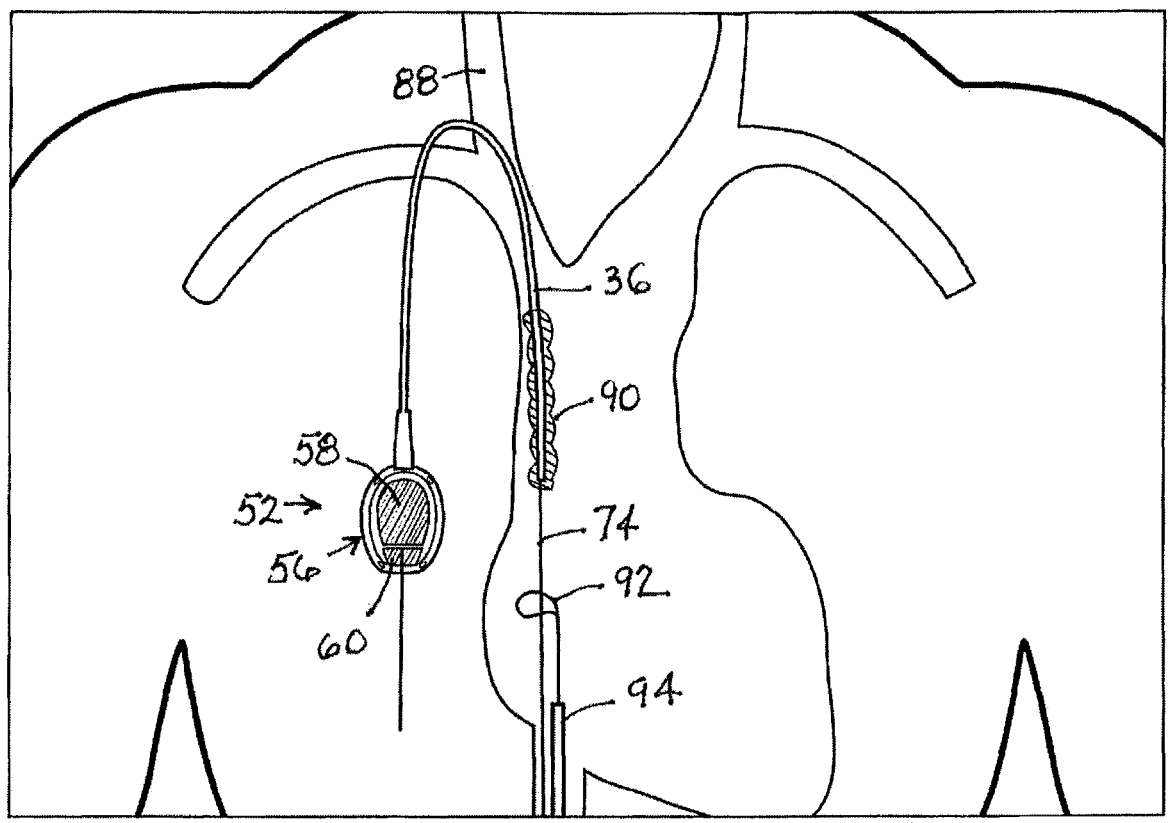
FIG. 27 is a diagram of a central venous access system in accordance with the present invention, demonstrating advancement of a loop snare over a wire, placed through the port horizontal septum, in preparation for fibrin sheath stripping, commensurate with the method described herein.
Figure 28:
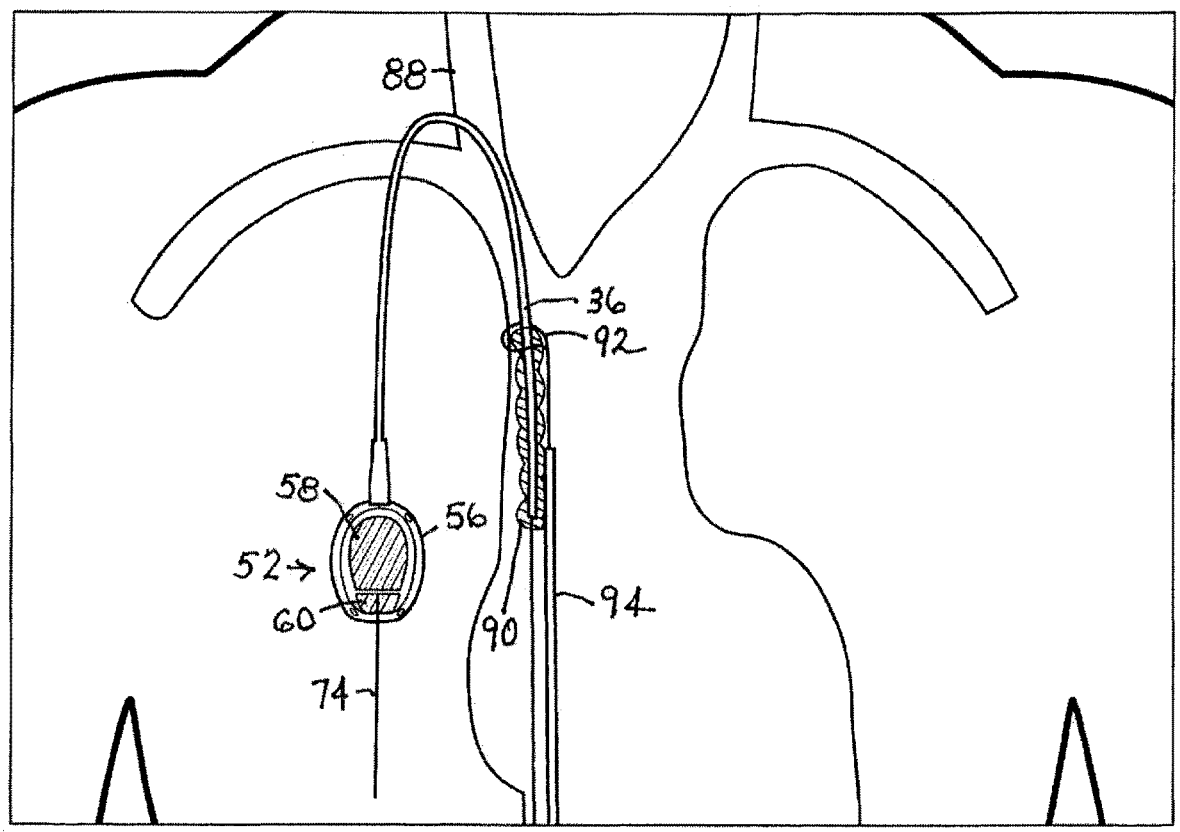
FIG. 28 is a diagram of a central venous access system in accordance with the present invention, similar to FIG. 27, demonstrating further advancement of a loop snare over a wire, placed through the port straight-line-access septum, and subsequently over a catheter coated with a fibrin sheath, ideally positioned to perform fibrin sheath stripping, commensurate with the method described herein.
Figure 29:
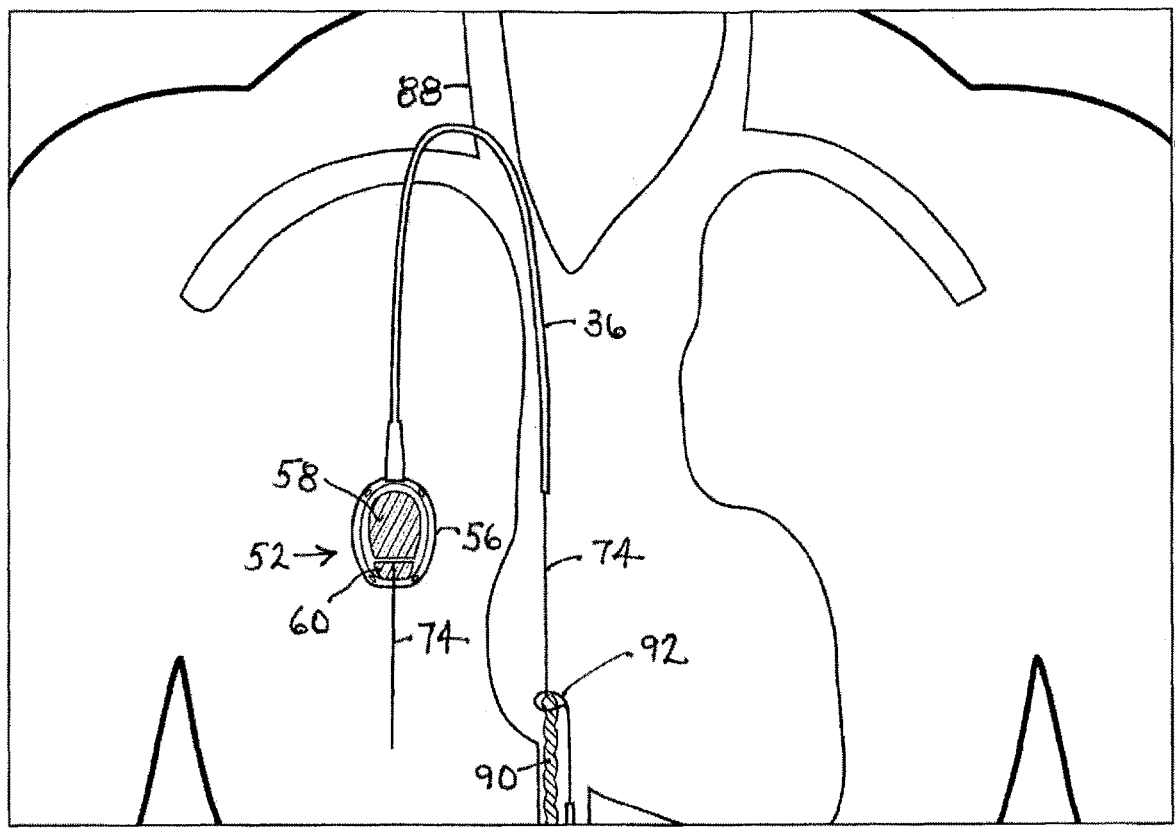
FIG. 29 is a diagram of a central venous access system in accordance with the present invention, similar to FIG. 28, demonstrating loop snare removal of a fibrin sheath over a wire, placed through the straight-line-access port septum, commensurate with the method described herein.
Figure 30:
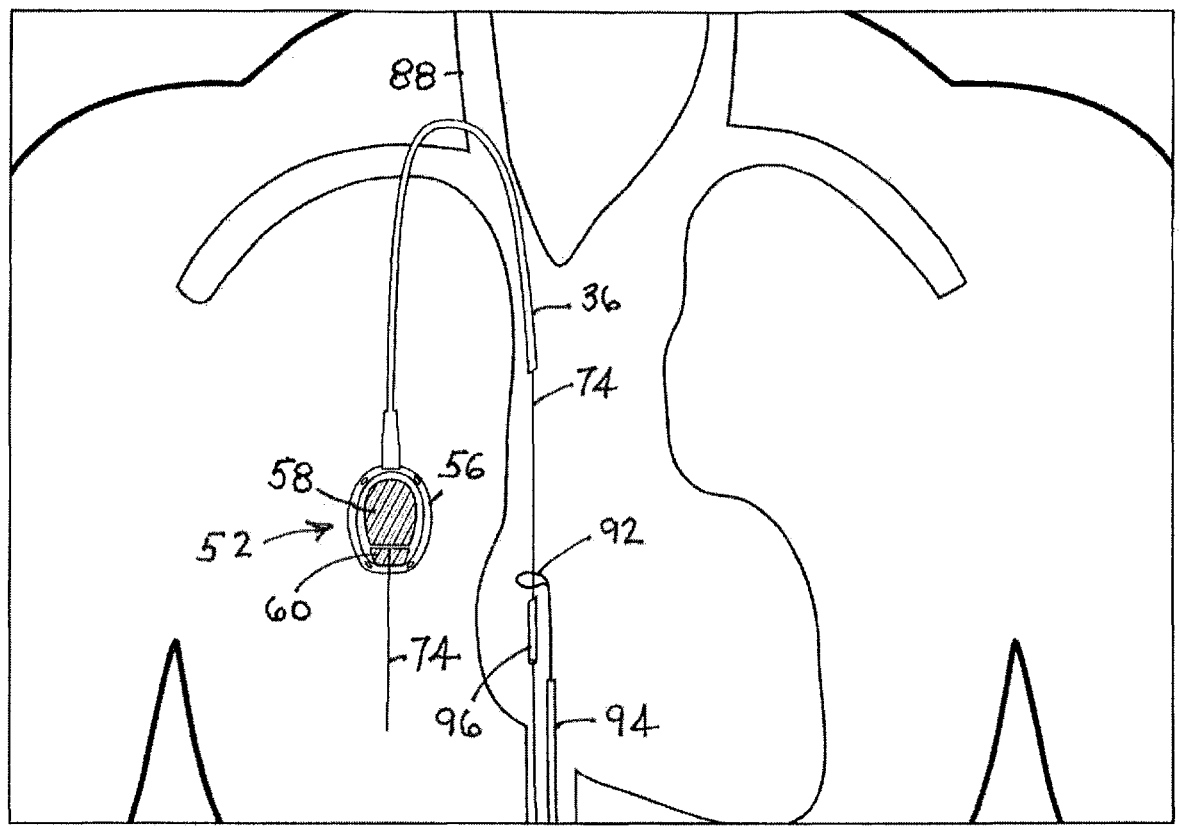
FIG. 30 is a diagram of a central venous access system in accordance with the present invention, similar to FIG. 28, demonstrating how the position of a broken catheter fragment can be removed in a controlled manner, over a wire placed through the straight-line-access port septum, preventing the complication of a free intravascular fragment shown in FIG. 25, commensurate with the method described herein.

FIG. 27 shows an improved fibrin sheath stripping procedure according to the present invention, utilizing the vascular port apparatus 52 described above with reference to FIGS. 5-11. The main port body 56 has two penetrable septa 58 and 60 covering respective apertures 158 and 160, with perpendicular-access septum or aperture 58 similar to that of conventional ports and with straight-line-access septum 60 primarily for the performance of various interventions to facilitate initial port placement, maintenance of secondary port patency, port removal, and port exchange. A slidable wire such as a polytetrafluoroethylene-coated guide wire, sold by the Terumo medical corporation under the trademark "GLIDEWIRE" or other suitable wire is inserted through a straight Huber needle or Seldinger needle via the straight-line-access port aperture 160, through the catheter 36 in order to secure the fibrin sheath 90 and help prevent catheter fragmentation from fibrin sheath stripping. An intravascular loop snare 92 exiting from a catheter 94 placed from a femoral vein puncture is shown surrounding the wire 74 in preparation for striping off the fibrin sheath from the catheter. FIG. 28, similar to FIG. 27, shows the port apparatus 52 in accordance with the present invention, with a fibrin sheath 90 or biofilm surrounding the distal intravascular portion of the catheter 36, resulting in catheter malfunction. An intravascular loop snare 92 exiting from a catheter 94 placed from a femoral vein puncture is shown surrounding the port catheter 36 and fibrin sheath 90, immediately prior to tightening the snare in preparation for striping off the fibrin sheath from the catheter 36. FIG. 29, similar to FIG. 28, shows subsequent safe removal of the fibrin sheath 90, with reduced risk of catheter fragmentation, from the port catheter 36 with the loop snare 92, over the wire 74 placed via the straight-line-access aperture 60. FIG. 30, similar to FIG. 29, shows safe removal of a catheter fragment 96 via a loop snare 92, since the fragment is secured on the wire 74 placed through the straight-line-access aperture 160, a known complication of fibrin sheath stripping, pursuit to the current invention. The catheter fragment 96 can then be safely removed after it is snared on the wire via the femoral vein access site trough a vascular sheath.

Figure 31:
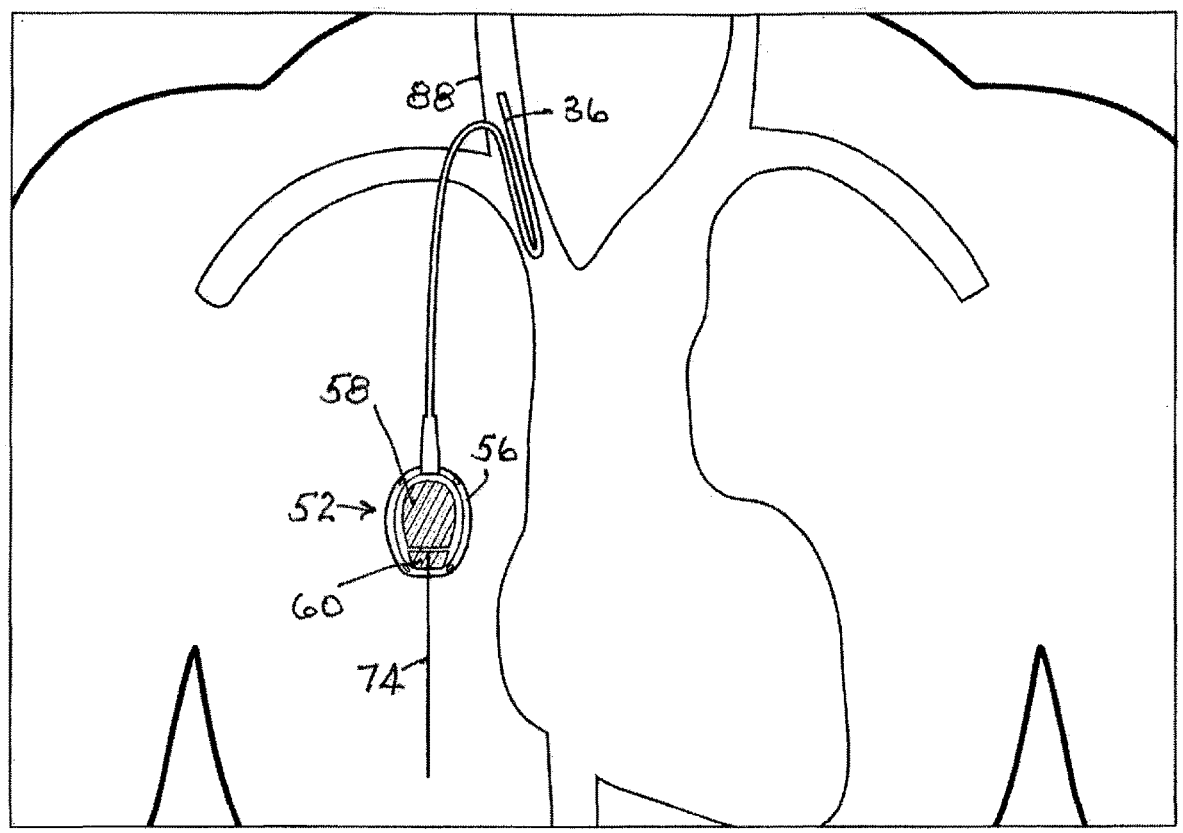
FIG. 31 is a diagram of a central venous access system in accordance with the present invention, showing a flipped catheter tip, and a wire being advanced into the straight-line-access port septum in preparation for catheter repositioning, commensurate with the method described herein.

FIG. 31 shows a port apparatus 52 pursuant to the current invention with a flipped or migrated aberrant catheter tip in the internal jugular vein 88, resulting in catheter dysfunction and an undesirable location to inject medicines, also predisposing to venous thrombosis, a known complication of central venous ports. A wire 74 is shown being placed into the straight-line-access port aperture 60 into the port catheter 36 prior to exiting the distal end of the catheter. The aberrant catheter position can be remedied by advancing a slidable wire 74 through the catheter, thereby repositioning it in the superior vena cava or right atrium, in accordance with the invention described herein as shown in FIG. 32.

Figure 32:
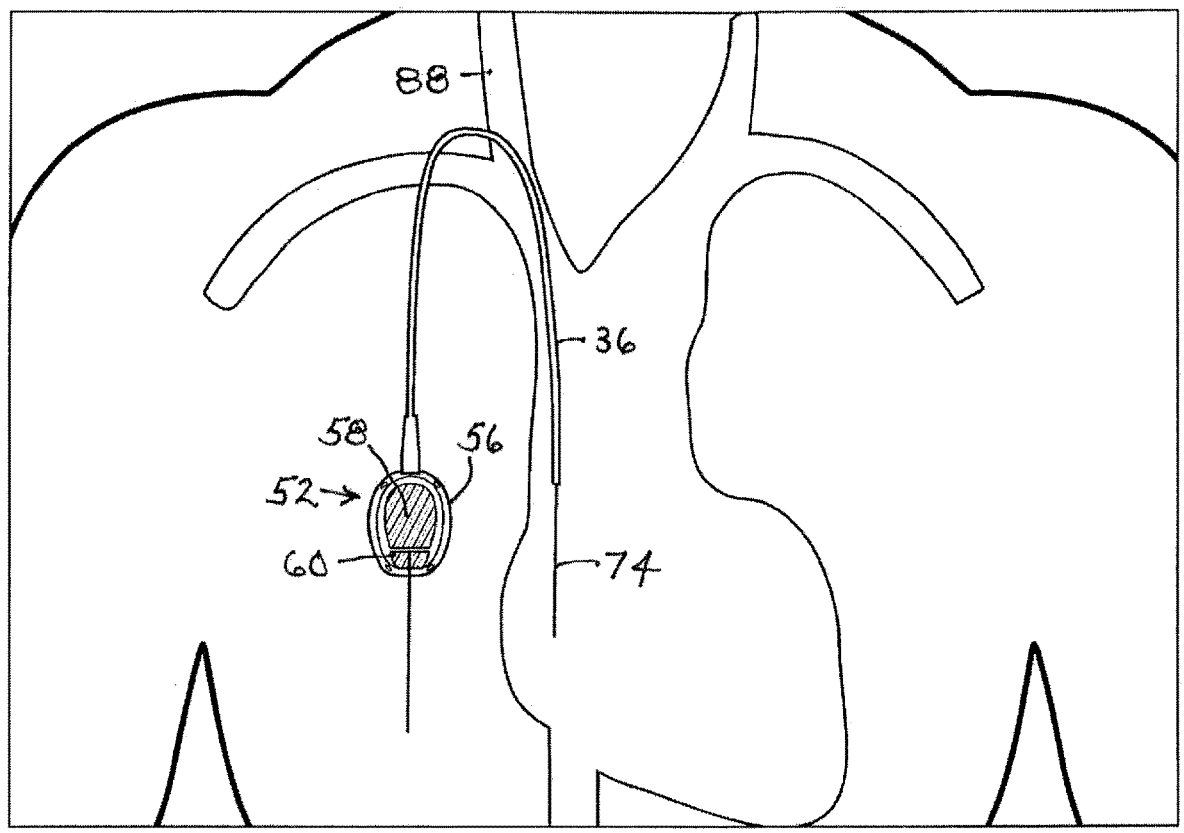
FIG. 32 is a diagram of a central venous access system in accordance with the present invention, similar to FIG. 31, showing a repositioned catheter tip performed utilizing a wire placed through the straight-line-access port septum, with the wire shown exiting from the end of the catheter, commensurate with the method described herein.
Figure 33:
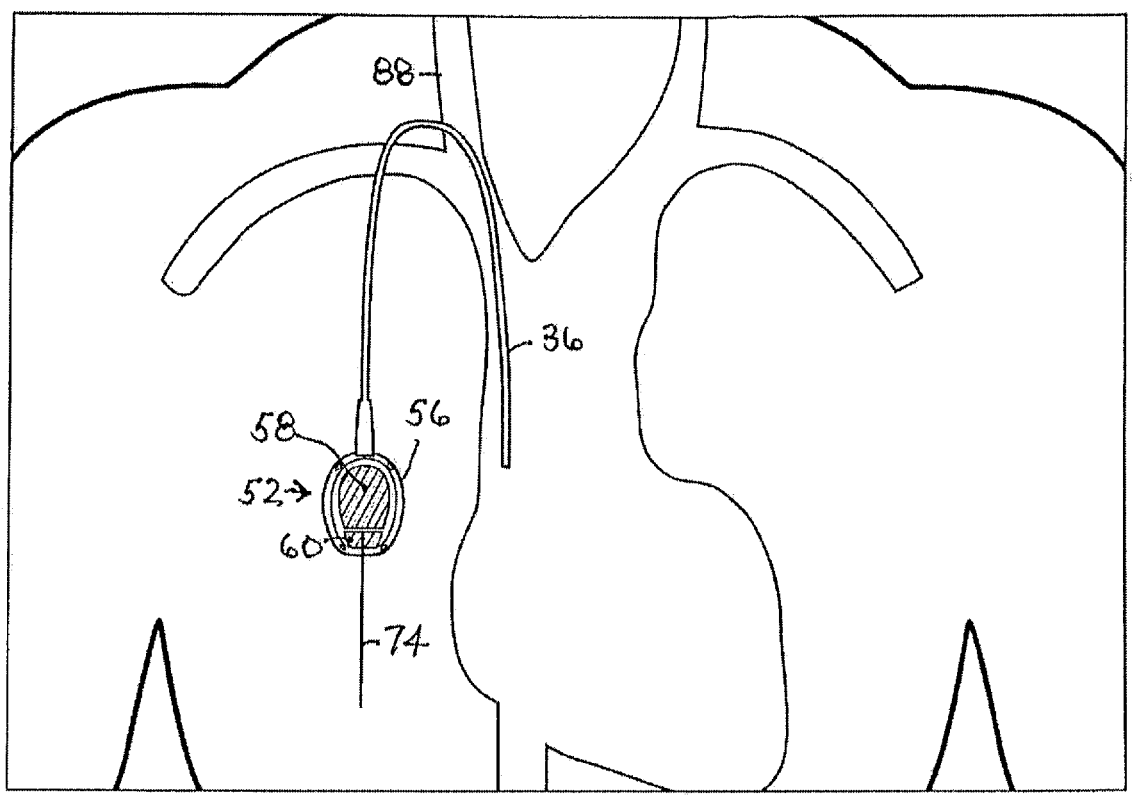
FIG. 33 is a diagram of a central venous access system in accordance with the present invention, similar to FIG. 32, showing a repositioned catheter tip performed utilizing a wire placed through the straight-line-access port septum, with the wire now haven been withdrawn back into the catheter, commensurate with the method described herein.

A wire placed through the straight-line-access aperture and subsequently the catheter as shown in FIG. 32 may be used to dislodge intraluminal blockages or thrombus in order to restore catheter patency. FIG. 33, similar to FIG. 32, shows partial wire withdrawal after catheter recanalization or dislodgement of the intraluminal thrombus from the catheter. FIG. 32 also demonstrates how various tools such as a microbrush or microballon may be advanced through the port apparatus in order to disrupt and dislodge an attached fibrin sheath or thrombus as an alternative procedure and method to that described for FIGS. 27-30.

A wire 74 placed through the straight-line-access aperture 60 and subsequently the catheter 36 as shown in FIG. 32 may facilitate initial catheter 36 placement into the central venous system, particularly if friction or kinking is encountered during catheter 36 advancement through a peel-away sheath, that is typically used in order to advance the catheter into the central venous system. Wire advancement may also be beneficial if a redundant loop of catheter develops in the subcutaneous tissues, after initial catheter 36 placement and peel away sheath removal, with only a small portion of the catheter in the venous system, thereby securing the catheter 36 in the venous system and increasing catheter 36 pushability such that the loop can be eliminated.

FIG. 32 also demonstrate how wire 74 advancement may help prevent inadvertent transection of the catheter during port removal increasing ones ability to palpate the catheter in order to avoid cutting it, also preventing complete transection by its presence within the catheter lumen; in the unlikely event of a complete transection the loose fragment may be secured on the wire allowing fragment 96 retrieval as demonstrated in FIG. 30.

FIG. 32 also demonstrates how placement of a long enough wire through the straight-line-access aperture through the catheter into the central venous system may allow for exchange of a malfunctioning port apparatus 52, after making an incision in the skin and freeing it from any surrounding scar tissue, for a new assembled vascular port apparatus 52 of a similar length over the wire. Exchange of a malfunctioning port apparatus 52 over a wire may require an incision near the straight-line-access aperture incorporating the access needle 72 (FIG. 21) and may be facilitated by peel-away sheath placement into the subcutaneous port pocket and catheter tunnel over the wire, after removal of the original malfunctioning port apparatus 52, thereby reducing friction for placement of the new port apparatus 52. The port apparatus may be exchanged for a like Portacath apparatus 52 or a new tunneled vascular apparatus such as a Hickman catheter or plasmapheresis catheter.

Figure 34:
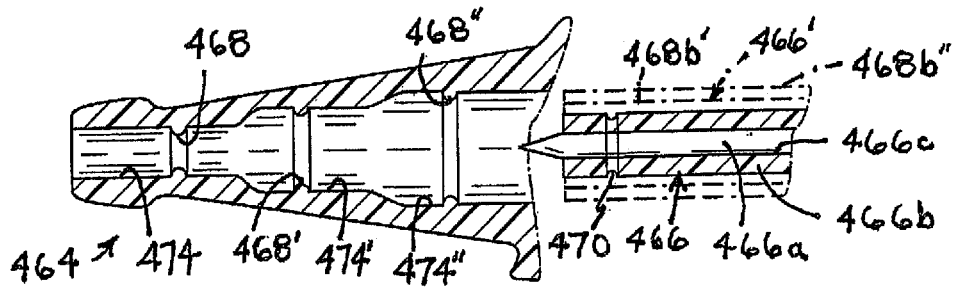
FIG. 34 is a schematic side elevational view of a non-coring needle and cannula assembly and a cross-sectional view of an outlet tube formed with cooperating snap-lock fit formations, utilizable in any of the vascular access ports disclosed herein.

FIG. 34 depicts a large-bore (19 to 14 gauge) non-coring needle assembly 466, either circular or semi-circular in transverse cross-section, for high flow access applications, for instance, for apheresis or dialysis, together with a hollow outlet tube 464 (either round or semicircular in cross-section) that may serve as the hollow outlet tube in any of various single (round outlet tube) or dual access (semicircular or round outlet tube lumen) implantable vascular ports described herein, such as outlet tubes 64, 264, 364, 522, 534, 538, 550, 582, 600. Non-coring access needle assembly (round or semicircular) 466 may comprise a sharp inner stylet 466a with an outer cannula 466b, stylet 466a traversing a longitudinal lumen 466c of the cannula. Outlet port or stem 464 is provided along an inner surface with at least one annular bead or ridge 468 that inserts into an annular groove or indentation 470 in an outer surface 472 of cannula 466b to lock the cannula to the outlet port in high flow applications. Bead 468 and groove 470 form a snap-lock fit that anchors cannula 466b in place and additionally provides tactile resistive and or vibratory feedback to the operator during a deployment or coupling procedure; the operator can sense in part through sound and in part through resistance to further forward motion or retraction, that bead 468 is seated in groove 470. A reversible snap-lock mechanism such as bead 468 and groove 470 may therefore minimize or eliminate the need for fluoroscopic guidance during horizontal or lateral access or straight-line access needle placement (0 to 70 degrees relative to the port floor). Seating of cannula 466b at the desired location within the length of outlet tube 464 is facilitated by the tactile, vibratory, and auditory feedback generated by the snap-fit mechanism. Different size annular beads or ridges (e.g., of different heights) may be staggered along the length of the outlet tube 464, from small (proximal) to big (distal), to accommodate and form a tight fit around more than one size needle diameter, anchoring or engaging a larger gauge needle more proximally in the outlet tube and smaller diameter needles more distally, most applicable in an outlet tube of a uniform or nearly uniform diameter throughout its length. Alternatively, the annular beads or ridges can be of the same size or height but may accommodate different needle diameters because of an overall step-wise tapering of the inner diameter or inner surface of the outlet tube 464 from big (proximal) to small (distal), thereby forming a tight fit around more than one size needle diameter, anchoring or engaging a larger gauge needle more proximally in the outlet tube and smaller diameter needles more distally. Of course, the locations of bead 468 and groove 470 may be reversed: bead 468 may be formed on cannula 466b and groove 470 along an inner surface 474 of tubular outlet port 464. Multiple annular beads 468, 468', 468" may be formed along inner surface 474, spaced from one another, to accommodate stylet needle assemblies 466, 466', 466" with cannulas 468b, 468b', 468" of different diameters or gauges. In that case, inner surface 474 of outlet tube 464 may exhibit longitudinally staggered sections, 474, 474', and 474" of respective diameters increasing in diameter in a proximal direction, that is, from a free end 464a of port 464 toward the respective port chamber. Typically needle stylet 466a is made of stainless steel while cannula 466b and/or outlet tube 466 is made of an at least partially resilient polymeric material, facilitating the snap-lock cooperation and formation of a seal.

Alternatively, multiple mutually spaced annular grooves 470 may be provided along outer surface 470 of cannula 466b. In another variation, needle assembly 466 and inner surface 474 of outlet port 464 may be formed with multiple co-acting pairs of beads and grooves all of the same diametric or radial dimensions but axially spaced from one another along the lengths of the needle assembly and the outlet port. The snap-lock coupling of bead 468 and groove 470 serves to not only maintain the high-flow cannula 466b fixed to the respective vascular port 52, 252, 352, but to facilitate coupling operations and to closely fit the cannula to the inner surface 474 of the respective outlet tube 64, 264, 364 to prevent back flow. The horizontal- or lateral sidewall-access aperture as disclosed herein enables straight-line large bore needle-assembly cannula access to the outlet tube 464, 64, 264 364 and the outlet tubes of all the vascular port devices disclosed herein, for enabling maximal flow rates relative to the perpendicular- or top-access aperture which has greater frictional loss and turbulence related to flow through the capacious chamber with the needle access at 90 degrees.

Any vascular access port described herein may be provided with a reversible snap-lock mechanism such as bead 468 and groove 470. Other kinds of reversible locking mechanisms well known to those skilled in the art may be used in substitution for a bead and groove snap-lock. For instance, any outlet port or stem of a dual-access vascular port disclosed herein may be provided with a screw-type locking mechanism with mating male spiral threads and female spiral grooves in the outlet stem and on the outer surface of a cannula of a non-coring needle assembly. Once the needle assembly cannula is engaged in the outlet port or stem, a user rotates the needle assembly, or at least the cannula thereof, clockwise or counter clockwise to engage and then in the opposite rotational direction to remove the needle assembly, particularly the cannula thereof. Alternatively, one may provide any outlet port or stem of a dual-access vascular port disclosed herein with a friction-fit locking mechanism with the outlet port or stem exhibiting a tapered inner surface of decreasing diameter, where a cannula of a non-coring needle assembly has a similarly tapered distal end. The tapered distal end of the cannula and the correspondingly tapered inner surface of the outlet port or stem together form a cooperating reversible locking mechanism. One of the cannula and the port, preferably the port or stem, is made of a metal while the other is made of a resilient high-friction material such as rubber polymer. The needle assembly cannula is forced into the outlet port or stem and remains stuck therein until a user pulls the needle assembly, particularly the cannula thereof to disengage the male-female friction lock and remove the needle assembly cannula. Other kinds of reversible locking mechanisms with cooperating elements on the outlet port or stem of a dual-mode vascular access port will occur to those skilled in the art. Typically, the cooperating elements include projections (male) and receivers (female) such as one or more radially extending tongues that insert into L-shaped recesses requiring a distal translation and then a rotation to lock and the reverse to unlock.

A number of options are available when utilizing the port device described herein for high flow access procedures such as apheresis or dialysis: two separate single lumen ports with one serving as the venous access and the second for the venous return; single lumen port placement, with the port serving as a venous access and use of peripheral intravenous cannulation for the venous return; or placement of a dual lumen port with both venous access and return capabilities. The snap-lock needle mechanism also facilitates and supports stable advancement of a wire or other endoluminal device through the horizontal or lateral or straight-line access needle for the performance of the various methods and procedures described herein, which facilitate port placement, maintenance of secondary patency including fibrin sheath stripping and microbrush/microballon utilization, port catheter repositioning, port removal, and port exchange, all enabled by the horizontal access aperture.

A snap-lock needle mechanism as contemplated herein may typically include male and female elements as depicted in FIG. 34. The outlet tube may be made of resilient polymeric material that enhances the operability of the snap-lock mechanism. The outlet tube may be further tapered distal to the snap-lock mechanism to accommodate a smaller intravascular catheter (which is fitted over the distal outlet tube tip with a locking collar) as needed.

Figure 35:
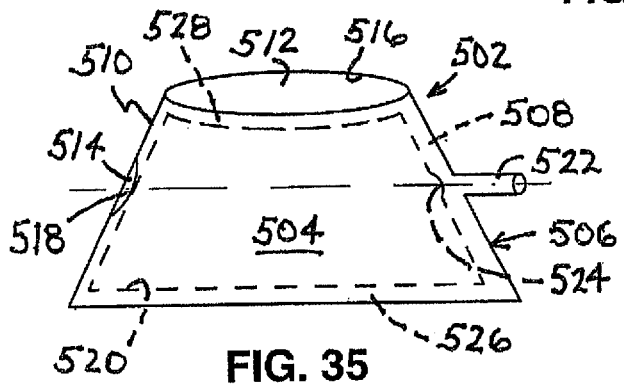
FIG. 35 is a schematic side elevational view of another implantable vascular access port in accordance with the present invention with frusto-conical body and frusto-conical (shown) or cylindrical chamber.

FIG. 35 depicts an implantable vascular port apparatus or device 502, which includes a frusto-conical main port body 506 having a frusto-conical internal chamber 504 formed therein. The main port body 506 has a sidewall 508 with a conical outer surface 510. The port body 506 and port chamber 504 may be of similar or differing shapes and or sizes respectively. FIG. 35 shows a frusto-conical port chamber 504 and frusto-conical outer port body 506. The main port body 506 has two penetrable septa 512 and 514 extending across and closing respective apertures 516 and 518. Aperture 516 is a perpendicular-access aperture similar to that of conventional ports, while aperture 518 constitutes a straight-line-access aperture primarily for high-flow applications and the performance of various interventions to facilitate initial port placement, port catheter repositioning, maintenance of secondary port patency, port removal, and port exchange. The septa 512 and 514 are formed from a resiliently deformable material such as silicone elastomer. The mounting of the septa 512 and 514 to the port body 506 may be as described above. The port body 506 is formed from a biocompatible material, such as titanium alloy or other biocompatible corrosion-resistant metal, or from a biocompatible plastic. A titanium liner may be used along a floor or bottom surface 520 of port chamber 504 when plastic is utilized for the port body 506. Access aperture 518 and an outlet tube 522, with an inner end defining an outlet aperture 524, is located midway between a lower wall or floor 526 and an upper wall 528 of port body 504.

Figure 36:
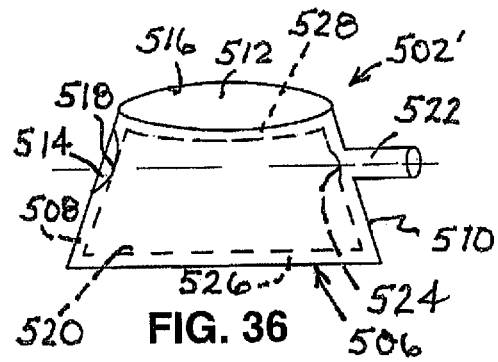
FIG. 36 is a schematic side elevational view of an implantable vascular access port similar to that of FIG. 35, showing an alternative more superior or higher positioning of inlet or lateral aperture and outlet stem.

A vascular access port 502' shown in FIG. 36 is the same as the port 502 of FIG. 35, and the reference numerals designating various component parts are the same. However, in the port of FIG. 35, access aperture 518, outlet aperture 524 and outlet tube 522 are located closer to upper wall 528 than to lower wall or floor 526.

Figure 37:
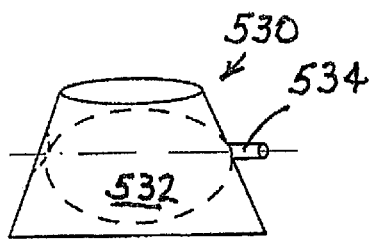
FIG. 37 is partially a schematic side-elevational view of a further implantable vascular access port in accordance with the present invention, showing a frusto-conical port body and an ovoid or ellipsoid chamber.
Figure 38:
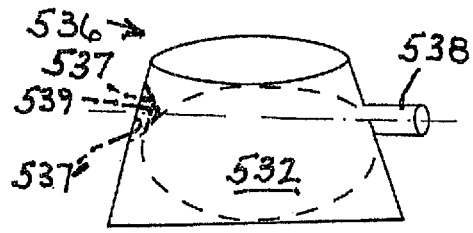
FIG. 38 is a schematic side elevational view of an implantable vascular access port similar to that of FIG. 37, showing a tangential outlet tube relative to an ovoid or ellipsoid port chamber and a conical-skin-covered external inwardly tapering recess or palpable depression, forming the lateral access aperture with inner septum.

A vascular access port 530 depicted in FIG. 37 is similar to the access ports 502 and 502' of FIGS. 35 and 36. Except for the different reference numerals as shown, port 530 exhibits the same structural features as ports 502 and 502'. Instead of a frusto-conical internal chamber 504, port 530 has an ovoid or ellipsoidal internal chamber 532. An outlet tube 534 joins chamber 532 substantially normal to the internal surface of the chamber. In contrast, a modified vascular access port device 536 illustrated in FIG. 38 has an outlet tube 538 that is connected tangentially to the ovoid or ellipsoidal internal port chamber 532, minimizing turbulent flow within the chamber. Port device 536 exhibits another feature that may be incorporated into any of the port devices disclosed herein, namely, a frusto-conical, conical or hemisphere shaped recess (inwardly tapering recess) 537, within the port body comprising the lateral access aperture, provided at an inner end with a self-sealing septum or membrane 539 for needle penetration at its junction with the inner chamber wall. Recess 537 has an edge 537' at an outer end that facilitates tactile detection via palpation of a patient's dermal and underlying tissues (palpable depression). Recess 537 typically has a frusto-conical surface (not separately designated), although other shapes may be used.

Figure 39:
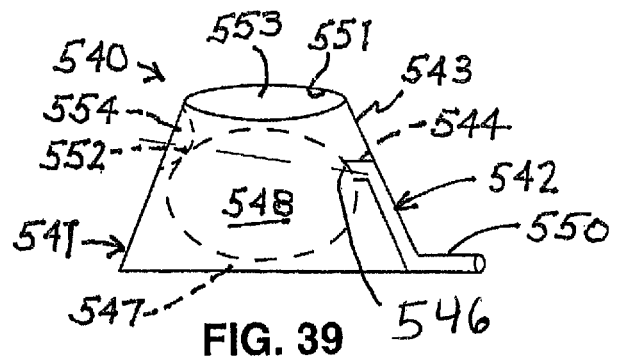
FIG. 39 is a schematic side elevational view of an implantable vascular access port similar to that of FIG. 38, showing a bent or doubly angled outlet tube.

As illustrated in FIG. 39, an implantable vascular port apparatus or device 540 includes a main port body 541 having a frusto-conical outer surface 543 and an ovoidal or ellipsoidal internal chamber 548. Internal chamber 548 is formed with an outlet aperture 546 through which the internal chamber is in communications with a bent, double angled, or snaking outlet tube 542, such that it ultimately exits the port flush or nearly flush with the port floor. Outlet tube 542 has an upstream portion 544 contiguous or continuous with outlet aperture 546 and a downstream portion 550 preferably disposed at or near a lower wall 547 of port body 541.

Port body 541 (FIG. 39) has two penetrable septa, an upper or top septum 553 for perpendicular low-flow access and a lateral septum 554 for transverse straight-line access utilizable in high-flow applications. Septa 553 and 554 extend across and cover respective apertures 551 and 552. Septa 553 and 554 are formed from a resiliently deformable material such as silicone elastomer. The mounting of the septa 553 and 554 to the port body 541 may be as described above. The port body 541 is formed from a biocompatible material, such as titanium alloy or other biocompatible corrosion-resistant metal, or from a biocompatible plastic. A titanium liner may be used along a floor or bottom surface 548' of internal chamber 548 when plastic is utilized for the port body 541.

Port apparatus or device 540 (FIG. 39) facilitates straight-line needle deployment in that both the access aperture 552 and the outlet aperture 546 are located near the upper end of the port device. Upstream portion 544 of outlet tube 542 is co-linear with access aperture 552 and its associated septum 554. The disposition of the downstream portion 550 of outlet tube 542 at the bottom or lower wall 547 of the port device minimizes or eliminates tilting of the device by a catheter connected to outlet tube 542.

Figure 40:
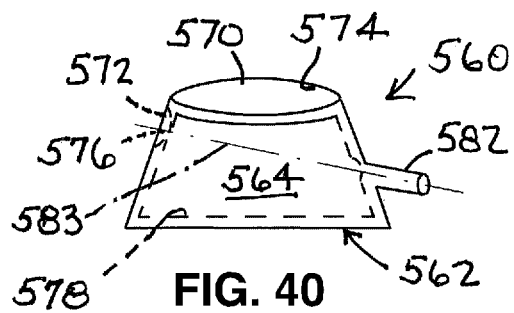
FIG. 40 is partially a schematic side-elevational view of yet another implantable vascular access port in accordance with the present invention, showing a frusto-conical port body and frusto-conical (shown) or cylindrical chamber and an inferiorly angled outlet stem.

FIG. 40 depicts an implantable vascular port apparatus or device 560, which includes a frusto-conical main port body 562 having a frusto-conical internal chamber 564 formed therein. The main port body 562 has a sidewall 566 with a conical outer surface 568. The main port body 562 has two penetrable septa 570 and 572 extending across and closing respective apertures 574 and 576. Aperture 574 is a perpendicular-access aperture similar to that of conventional ports, while aperture 576 constitutes a straight-line-access aperture primarily for high-flow applications and the performance of various interventions to facilitate initial port placement, port catheter repositioning, maintenance of secondary port patency, port removal, and port exchange. The septa 570 and 572 are formed from a resiliently deformable material such as silicone elastomer. The mounting of the septa 570 and 572 to the port body 562 may be as described above. The port body 562 is formed from a biocompatible material, such as titanium alloy or other biocompatible corrosion-resistant metal, or from a biocompatible plastic. A titanium liner may be used along a floor or bottom surface 578 of port chamber 564 when plastic is utilized for the port body 562. Access aperture 576 is located at an upper end of sidewall 566, while an outlet aperture 580 is disposed lower down along sidewall 566. An outlet tube 582 communicating with internal chamber 564 via outlet aperture 580 is inclined downwardly, co-linear with a straight-line insertion path 583 for a needle extending from access aperture 576 to outlet aperture 580. The design facilitates entrance into the straight-line access aperture 576 relative to the skin surface while at the same time minimizing tilting of the port by the weight of the exiting catheter.

Figure 41:
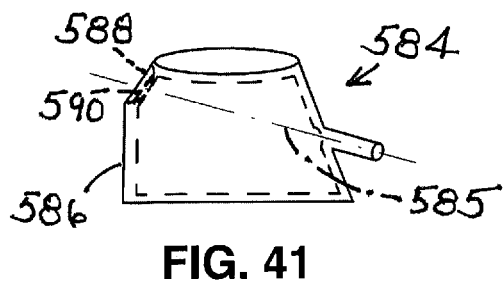
FIG. 41 is a schematic side elevational view of an implantable vascular access port similar to that of FIG. 40, showing a modified frusto-conical port body shape and lateral access aperture with an inferiorly angled outlet stem.

FIG. 41 depicts an implantable modified frusto-conical vascular access port 584 with a downwardly inclined needle insertion path 585 similar to that of the frusto-conical port 560. Port 584 has a different external geometry with a skewed conical sidewall 586 having a straight-line access aperture 588 and associated septum 590 directed at an angle for facilitating access. The skewed conical sidewall 586 may further facilitate entrance into the straight-line access aperture 588 relative to the skin surface while at the same time minimizing tilting of the port by the weight of the exiting catheter. Otherwise, port 584 exhibits the same structural feature as port 560, including the geometry of the internal chamber 564.

Figure 42:
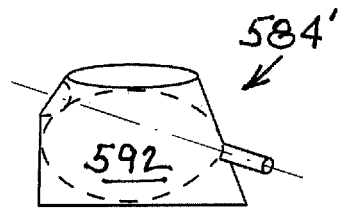
FIG. 42 is a schematic side elevational view of an implantable vascular access port similar to that of FIG. 41, showing an ellipsoidal internal chamber with an inferiorly angled outlet stem.
Figure 43:
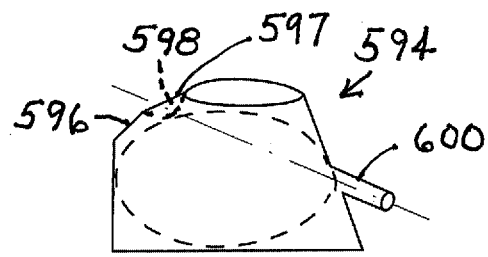
FIG. 43 is a schematic side elevational view of an implantable vascular access port body similar to that of FIG. 42, showing a tangential outlet stem and access aperture relative to an ellipsoidal port chamber with an inferiorly angled outlet stem.

FIG. 42 depicts a modified frusto-conical vascular access port 584' similar to port 584 of FIG. 41 but with an ovoid or ellipsoidal internal chamber 592, while FIG. 43 shows a modified frusto-conical vascular port 594, similar to port 584' of FIG. 42, with an upper sidewall portion having two mutually inclined facets 596 and 597 at an upper end and a steep angle access aperture 598, relative to the port floor, located in that curved sidewall portion. Port 594 also has a slanted and tangentially oriented outlet tube 600 relative to the ovoid or ellipsoidal inner chamber 592, optimizing flow dynamics within the chamber.

FIG. 44 illustrates a double lumen implantable vascular access port 602 with two internal port chambers 604, 605 separated by a midline divider or partition 606 with two perpendicular-access apertures (not shown) and two straight-line-access apertures 616 and 618. The port 602 includes a main port body 610 that is elliptic frusto-conical or oblate spherical in configuration and that has four penetrable septa, namely two perpendicular-access septa (not shown) covering respective apertures (not shown), similar to conventional double ports and the other double lumen port pursuant to the invention described herein (FIG. 12), as well as two straight-line-access septa 612 and 614 over apertures 616 and 618, primarily for high-flow applications and for the performance of various interventions to facilitate port placement, port repositioning, maintenance of secondary port patency, port removal, and port exchange. The septa 612, 614 are formed from a resiliently deformable material such as silicone elastomer and may include a thickened central portion (not illustrated), anchored or mounted as described above.

Needle insertion paths 620 and 622 from apertures 616, 618 and septa 612, 614 to round outlet apertures 624 and 626 at the upstream sides of semi-cylindrical outlet tubes 628 and 630 are straight lines preferably angled in towards one another, so as to provide space outside septa 612, 614 for manipulating two needles simultaneously, if necessary. Also straight-line insertion paths 620 and 622 may be angled downwardly (as illustrated in FIGS. 40-43) to place the access apertures 616, 618 closer to the skin surface to thereby facilitate aperture locating and needle deployment. Such a double lumen vascular access port may be used in carrying out an apheresis or dialysis procedure. Each round outlet aperture may transition into respective semicircular outlet tube lumens. In another version each round outlet aperture may transition into two separate round parallel or near parallel outlet tubes and outlet tube lumens, perhaps necessitating less inward angling of the needle insertion pathways. The separate outlet stems may be attached to separate intravascular catheters in this alternative device version.

Figure 45:
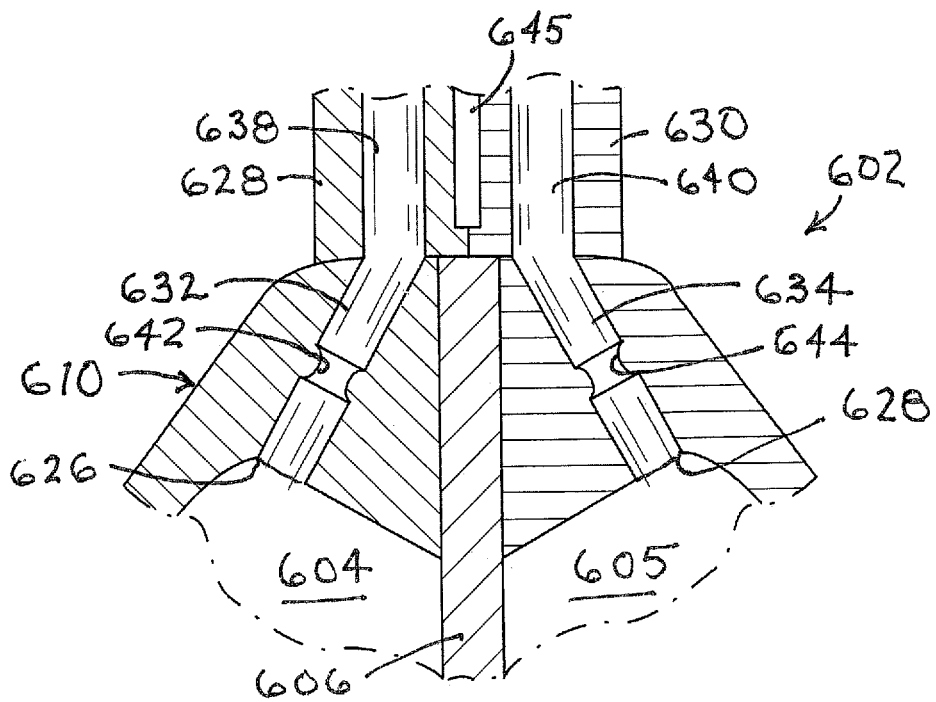
FIG. 45 is a detail of FIG. 44, on a larger scale, showing annular beads inside respective passageways in a port body wall, for reversibly locking a stylet needle cannula to the port body to enable fluid communication between the passageways and respective channels in a dual-flow outlet tube.

As depicted in more detail in FIG. 45, port body 610 of the double lumen implantable vascular access port 602 of FIG. 44 has passageways or channels 632 and 634 that extend in a sidewall 636 of the port body from respective outlet apertures 624 and 626 to respective lumens 638 and 640 of outlet tubes 628 and 630. Passageways 632 and 634 are provided with inwardly projecting annular beads 642 and 644 that cooperate with annular grooves on a round stylet needle cannula (see FIG. 34 and associated description) to reversibly lock the needle cannulas to the port body 610 for high flow applications. The double lumen composite outlet tube 628, 630 contains a midline groove or slit 645 (not visible in FIG. 44), which accepts a midline divider (253, see FIGS. 15 and 16) of a double lumen catheter (28, FIGS. 15 and 16).

Figure 46:
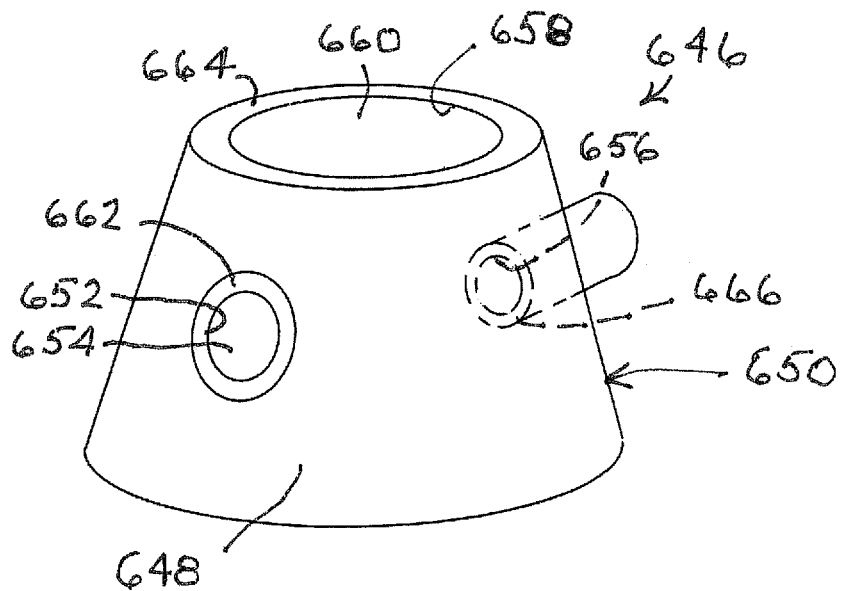
FIG. 46 is a schematic perspective view of a generic vascular access port in accordance with the present invention, showing areas of different degrees of radio-opacity or -translucence to facilitate use under fluoroscopic guidance.

As illustrated in FIG. 46, an implantable vascular access port 646 representative of any port described herein may be provided with varying degrees of radio-opacity or radio-translucency to facilitate access under fluoroscopic guidance. A major portion 648 of a port body 650 has a first predetermined degree of radio-opacity. A lateral access aperture 652 and its associated septum 654, as well as an outlet aperture 656 and optionally a top access aperture 658 and its associated septum 660, exhibit a second predetermined degree of radio-opacity. The port body may be provided with edge regions 662, 664 and optionally 666 that extend about and define lateral-access aperture 652, outlet aperture 656 and top access aperture 658, respectively, the edge regions 662, 664, 666 having a third predetermined degree of radio-opacity. At least one of the second and the third predetermined degrees of radio-opacity differs substantially from the first predetermined degree of radio-opacity. In other words, the radio-opacity (concomitantly radio-translucence) of the different apertures 652, 656 and 658 vary so as to enable fluoroscopic visualization. Thus lateral access aperture 652 and outlet aperture 656 may be readily localized visually during a needle insertion procedure particularly for high-flow applications such as apheresis and dialysis. Radio-opacity may vary between essentially zero (radio-translucence) and essentially 100% (completely radio-opaque). The degrees of radio-opacity are understood as qualitative in that each degree of radio-opacity can lie within a numerical or percentage range but where the degrees differ for enhancing visualization, the respective ranges of radio-opacity do not overlap. Thus the various physical features are fluoroscopically distinguishable. It is to be understood that the radio-opacity of lateral access aperture 652 and top (vertical) access aperture 658 is the same as, and determined by, the radio-opacity of the associated septum 654 and 660.

Figure 47:
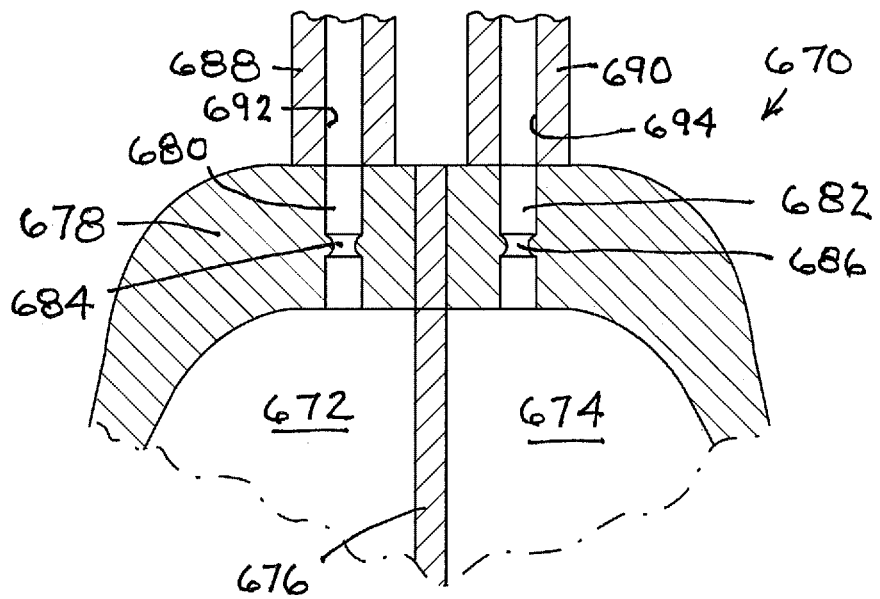
FIG. 47 is a schematic partial cross-sectional view of a dual chamber vascular access port with dual outlet tubes, pursuant to the present invention.

As illustrated in FIG. 47, a double lumen vascular access port 670 has two internal chambers 672, 674 separated by a divider or partition 676 as discussed herein above with reference to FIG. 44. A port body wall 678 has two cylindrical channels 680, 682 defining respective outlet apertures (not separately designated) and provided with respective annular resilient beads 684, 686 for insertion in snap-lock fits into grooves on outer surfaces of stylet-needle assembly cannulas (not shown). Two separate outlet tubes 688 and 690 are attached to or integral with port body wall 678 with lumens 692 and 694 coaxial and communicating with respective channels 680, 682. In a modification of the embodiment of FIG. 47, the snap-lock beads 684, 686 may be provided in the outlet tube lumens 692 and 694 rather than in channels 680, 682.

Figure 48:
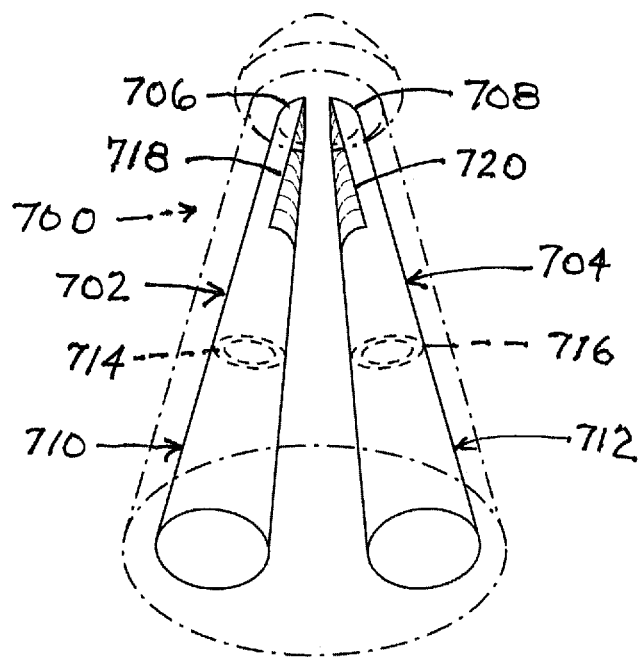
FIG. 48 is a diagram of an outlet tube for a dual chamber vascular access port, showing two lumens each with a distal end having a D-shaped cross-section (semi-cylindrical) and a proximal end with a circular cross-section.

As depicted in FIG. 48, an outlet tube 700 for use with dual lumen vascular access port 252 in place of double lumen hollow outlet tube 264 (FIGS. 12-16) includes two lumens 702, 704 each with a distal end 706, 708 having a D-shaped cross-section and a proximal end portion 710, 712 with a circular cross-section. Proximal end portions 710, 712 are formed internal with inwardly projecting annular beads 714, 716 for removable insertion in annular grooves in cannulas (not shown) of respective stylet needle assemblies (not shown). Between each distal end 706, 708 and the respective proximal end portion 710, 712, the respective lumen, 702, 704 is formed with a transition section (not separately designated) including a half surface 718, 720 that gradually morphs from a linear configuration at distal end 706, 708 to a semi-circular profile at proximal end portion 710, 712. Thus outlet tube 700 accommodates cylindrical needle cannulas at an inner or proximal end and a conventional bifurcated catheter (see 284 in FIG. 15) at an outer or distal end. Outlet tube 700 may taper from a wider proximal end at the port body to a smaller diameter at the distal end where the intravascular catheter is joined to the outlet tube.

What is claimed is:

1. An implantable vascular access port, comprising:
a port body having a lower or floor wall, an upper wall opposed thereto and at least one sidewall extending between said upper wall and said lower or floor wall, said port body having at least one internal chamber, said port body having at least one outlet aperture formed in said at least one sidewall in communication with said at least one internal chamber, said port body having at least one first access point or location defining an at least partially horizontal-access path or direction to said at least one outlet aperture through said at least one internal chamber, said port body being formed in said upper wall with at least one second access point or location defining a perpendicular- or vertical-access path or direction substantially perpendicular to said lower or floor wall; and
at least one hollow outlet tube attached to the port body and in fluid communication with said at least one internal chamber and said at least one outlet aperture, wherein at least one of said at least one hollow outlet tube and said port body proximate said at least one outlet aperture is configured internally for cooperating with an outer surface of a distal end portion of a needle cannula inserted through said first access point or location to removably or reversibly lock the cannula, upon an insertion of said distal end portion thereof into said at least one internal chamber, to said at least one hollow outlet tube or said port body proximate said at least one outlet aperture so that the cannula communicates with said lumen of said at least one hollow outlet tube.

2. The implantable vascular access port of claim 1 wherein said at least one of said at least one hollow outlet tube and said port body proximate said at least one outlet aperture is formed with a male or female locking element and said outer surface of said needle cannula is provided with a female or male locking element, respectively.

3. The implantable vascular access port of claim 1 wherein said at least one internal chamber is provided in said at least one sidewall with at least one outwardly tapering chamber extension having a first transverse dimension at said at least one internal chamber and a second transverse dimension at said at least one outlet aperture, said first transverse dimension being larger than said second transverse dimension, said at least one outlet aperture being spaced from said at least one internal chamber by a length or height dimension of said at least one outwardly tapering chamber extension.

4. The implantable vascular access port of claim 3, wherein said at least one outwardly tapering chamber extension is aligned with said at least one first access point or location such that during a medical procedure when a tip portion of a hollow needle cannula is inserted into said at least one internal chamber, a surface of said at least one outwardly tapering chamber extension passively guides the hollow needle cannula or wire toward said at least one outlet aperture, into said at least one hollow outlet tube, enabling wire advancement into a catheter attached to said at least one hollow outlet tube.

5. The implantable vascular access port of claim 1, wherein said at least one first access point or location comprises a palpable inwardly tapering recess.

6. The implantable vascular access port of claim 1, wherein said at least one sidewall has, on a side opposite said at least one outlet aperture, an outer surface having a lower portion and an upper portion bearing different angles relative to said upper wall and said lower or floor wall, said upper portion being slanted from said lower portion towards said upper wall.

7. The implantable vascular access port of claim 6, wherein said at least one hollow outlet tube has, at an inlet end proximal said at least one internal chamber, an axis co-linear with said at least partially horizontal-access path or direction.

8. The implantable vascular access port of claim 1, wherein said at least one sidewall has an outer surface with at least a portion with a profile taken from the group consisting of straight, sloped, and curved.

9. The implantable vascular access port of claim 1, wherein:
a major portion of said port body has a first predetermined degree of radio-opacity;
said at least one first access point or location and said at least one outlet aperture exhibit a second predetermined degree of radio-opacity;
said port body has edge regions extending about and defining said at least one first access point or location and said at least one outlet aperture, said edge regions having a third predetermined degree of radio-opacity; and
at least one of said second predetermined degree of radio-opacity and said third predetermined degree of radio-opacity differs substantially from said first predetermined degree of radio-opacity.

10. The implantable vascular outlet port of claim 1, further comprising a catheter attached to said at least one hollow outlet tube, and at least one medical instrument or tool taken from the group consisting of guide wires, needles, microbrush or microballoon devices, said at least one medical instrument or tool extending through said at least one first access point or location, said at least one internal chamber, said at least one outlet aperture, and said at least one hollow outlet tube, and said catheter for the performance of an intravascular procedure.

11. The implantable vascular access port of claim 1 wherein said at least one of said at least one hollow outlet tube and said port body proximate said at least one outlet aperture at least in part comprises an elastomeric material.

12. The implantable vascular access port of claim 1 wherein:
said at least one first access point or location has a position at an upper end of said port body;
said at least one outlet aperture is disposed lower down than said at least one access aperture along said sidewall; and
said at least partially horizontal-access path or direction to said at least one outlet aperture through said at least one internal chamber is inclined downwardly at an angle.

13. An implantable vascular access port, comprising:
a port body having a lower or floor wall, an upper wall and at least one sidewall extending between said upper wall and said lower or floor wall, said port body having at least one internal chamber, said port body having at least one outlet aperture formed in said at least one sidewall thereof in communication with said at least one internal chamber, said port body having, substantially opposite said at least one outlet aperture, at least one access point or location defining an at least partially horizontal-access path or direction to said at least one outlet aperture through said at least one internal chamber;
at least one septum attached to said port body and covering or closing said at least one internal chamber at said at least one access point or location; and
at least one hollow outlet tube attached to the main port body and in fluid communication with said at least one internal chamber and said at least one outlet aperture, wherein at least one of said at least one hollow outlet tube and said port body proximate said at least one outlet aperture is configured internally for cooperating with an outer surface of a distal end portion of a needle cannula inserted through said at least one access point or location, to removably or reversibly lock the cannula, upon an insertion of the distal end portion thereof into said at least one internal chamber, to said at least one hollow outlet tube or said port body proximate said at least one outlet aperture so that the cannula communicates with said lumen of said at least one hollow outlet tube.

14. The implantable vascular access port of claim 13 wherein (i) said at least one of said at least one hollow outlet tube and said port body proximate said at least one outlet aperture and (ii) said outer surface of said needle cannula are adapted to cooperate with one another in a lock mechanism that facilitates needle cannula stability, (i) said at least one of said at least one hollow outlet tube and said port body proximate said at least one outlet aperture and (ii) said outer surface of said needle cannula being configured to create a tight seal with one another to enable backflow and turbulence prevention in high-flow procedures.

15. The implantable vascular access port of claim 13 wherein at least one of (i) said at least one of said at least one hollow outlet tube and said port body proximate said at least one outlet aperture and (ii) said outer surface of said needle cannula at least in part comprises an elastomeric material.

16. The implantable vascular access port of claim 13 wherein (i) said at least one of said at least one hollow outlet tube and said port body proximate said at least one outlet aperture and (ii) said outer surface of said needle cannula are configured to cooperate with one another to reversibly fix said needle cannula to said port body, thereby facilitating wire navigation through said needle cannula, said at least one internal chamber and said at least one hollow outlet tube and into a catheter attached thereto and also facilitating longitudinal migration or movement of said port body and said catheter over a wire for port implantation, repositioning, removal, or exchange.

17. The implantable vascular access port of claim 13 wherein said at least one of said at least one hollow outlet tube and said port body proximate said at least one outlet aperture is provided internally with at least one first locking element configured for cooperating with at least one second locking element on said outer surface of said needle cannula, to removably or reversibly lock the cannula to said at least one hollow outlet tube or said port body so that the cannula communicates with a lumen of said at least one hollow outlet tube.

18. The implantable vascular access port of claim 13 wherein:
said at least one access point or location has a position at an upper end of said port body;
said at least one outlet aperture is disposed lower down than said at least one access aperture along said sidewall; and
said at least partially horizontal-access path or direction to said at least one outlet aperture through said at least one internal chamber is inclined downwardly at an angle.

19. An implantable vascular access port, comprising:
a port body having a lower or floor wall, an upper wall and at least one sidewall extending between said upper wall and said lower or floor wall, said port body having at least one internal chamber, said port body having at least one outlet aperture formed in said at least one sidewall thereof in communication with said at least one internal chamber, said port body having, substantially opposite said at least one outlet aperture, at least one access point or location defining an at least partially horizontal-access path or direction to said at least one outlet aperture through said at least one internal chamber;
at least one septum attached to said port body and covering or closing said at least one internal chamber at said at least one access point or location; and
at least one hollow outlet tube attached to the main port body and in fluid communication with said at least one internal chamber and said at least one outlet aperture, wherein:
said at least one access point or location has a position at an upper end of said port body;
said at least one outlet aperture is disposed lower down than said at least one access aperture along said sidewall; and
said at least partially horizontal-access path or direction to said at least one outlet aperture through said at least one internal chamber being inclined downwardly at an angle.

20. The implantable vascular access port of claim 19 wherein at least one of said port body and said at least one hollow outlet tube is configured internally for cooperating with an outer surface of a distal end portion of a needle cannula inserted through said at least one access point or location to removably or reversibly lock the cannula, upon an insertion of said distal end portion thereof into said at least one internal chamber, to said at least one hollow outlet tube or said port body so that the cannula communicates with said lumen of said at least one hollow outlet tube.

* * * * *